(12) United States Patent
Mikhail et al.

(10) Patent No.: US 11,890,405 B2
(45) Date of Patent: Feb. 6, 2024

(54) MULTI-PORT SYRINGE SYSTEM AND METHOD FOR USE WITH A URINARY CATHETER

(71) Applicants: Albert A. Mikhail, Sherman Oaks, CA (US); Corollos Samir Abdelshehid, Los Angeles, CA (US)

(72) Inventors: Albert A. Mikhail, Sherman Oaks, CA (US); Corollos Samir Abdelshehid, Los Angeles, CA (US)

( * ) Notice: Subject to any disclaimer, the term of this patent is extended or adjusted under 35 U.S.C. 154(b) by 883 days.

(21) Appl. No.: 16/921,867

(22) Filed: Jul. 6, 2020

(65) Prior Publication Data
US 2020/0330724 A1    Oct. 22, 2020

Related U.S. Application Data

(63) Continuation-in-part of application No. 15/822,103, filed on Nov. 24, 2017, now Pat. No. 10,737,057.
(Continued)

(51) Int. Cl.
*A61M 25/00*    (2006.01)
*A61M 5/315*    (2006.01)
(Continued)

(52) U.S. Cl.
CPC .............. *A61M 1/772* (2021.05); *A61M 1/81* (2021.05); *A61M 3/0262* (2013.01);
(Continued)

(58) Field of Classification Search
CPC ........ A61M 1/772; A61M 1/774; A61M 1/81; A61M 2039/1077; A61M 2039/229;
(Continued)

(56) References Cited

U.S. PATENT DOCUMENTS 2,854,027 A    9/1958 Kaiser et al.
3,344,785 A *  10/1967 Hamilton .............. A61M 39/04
                                                    285/391
(Continued)

*Primary Examiner* — Quynh-Nhu H. Vu

(57) ABSTRACT

A multi-port medical syringe comprises a port body, a syringe barrel, and a plunger. The port body comprises a cylindrical cavity with at least three ports. The three port are configured to connect the cylindrical cavity of the port body with three medical devices: a first port configured for attachment to a medical device such as an input fluid source; a second port configured for fluid transmission through a urinary catheter to a bladder of a human or animal; and a third port configured for attachment to a medical device such as a drainage fluid storage vessel. The syringe barrel comprises a cylindrical tube, at least a portion of which fits snugly inside the cylindrical cavity of the port body. The syringe barrel further comprises a syringe barrel port located proximate to, or in, an otherwise closed end of the syringe barrel. Selection of the first, second or third port comprises a rotation of the syringe barrel relative to the port body, about the barrel cylindrical tube central axis, to align the syringe barrel port with the selected port body port. The plunger fits inside the cylindrical tube of the syringe barrel. The plunger can be manually grasped and moved longitudinally along the barrel cylindrical tube central axis to transmit fluid through the port of the port body that was selected by rotating the syringe barrel inside the port body.

20 Claims, 27 Drawing Sheets

Related U.S. Application Data

(60) Provisional application No. 62/426,583, filed on Nov. 27, 2016.

(51) Int. Cl.
*A61M 5/31* (2006.01)
*A61M 3/02* (2006.01)
*A61M 39/10* (2006.01)
*A61M 25/04* (2006.01)
*A61M 5/00* (2006.01)
*A61M 5/14* (2006.01)
*A61M 1/00* (2006.01)

(52) U.S. Cl.
CPC .......... *A61M 3/0283* (2013.01); *A61M 5/002* (2013.01); *A61M 5/1411* (2013.01); *A61M 5/3129* (2013.01); *A61M 5/31513* (2013.01); *A61M 25/0017* (2013.01); *A61M 25/04* (2013.01); *A61M 39/10* (2013.01); *A61M 1/774* (2021.05); *A61M 2005/3125* (2013.01); *A61M 2005/3128* (2013.01); *A61M 2039/1077* (2013.01); *A61M 2210/1085* (2013.01); *A61M 2250/00* (2013.01)

(58) Field of Classification Search
CPC ...... A61M 2210/1085; A61M 2250/00; A61M 25/0017; A61M 3/0229; A61M 3/0262; A61M 3/0283; A61M 39/10; A61M 39/223; A61M 5/3129; A61M 2005/3131; A61M 5/31513
See application file for complete search history.

(56) References Cited

U.S. PATENT DOCUMENTS

| | | |
|---|---|---|
| 3,780,736 A | 12/1973 | Chen |
| 3,990,447 A | 11/1976 | Vega |
| 4,082,095 A | 4/1978 | Mendelson et al. |
| 4,525,156 A | 6/1985 | Benusa et al. |
| 4,662,868 A | 5/1987 | Cambio |
| 4,784,637 A * | 11/1988 | Ryder .................. A61M 1/772 604/38 |
| 4,895,562 A | 1/1990 | Lopez |
| 4,904,245 A * | 2/1990 | Chen .................. A61M 3/0233 604/248 |
| 5,047,102 A | 9/1991 | Leuschner et al. |
| 5,049,135 A | 9/1991 | Davis |
| 5,074,334 A | 12/1991 | Onodera |
| 5,254,086 A | 10/1993 | Palmer et al. |
| 5,443,447 A * | 8/1995 | Kassis .................. A61M 29/00 604/24 |
| 5,466,228 A * | 11/1995 | Evans ................. F16K 11/0853 604/32 |
| 5,603,700 A | 2/1997 | Daneshvar |
| 6,457,488 B2 * | 10/2002 | Loo .................... A61M 39/223 222/387 |
| 6,953,450 B2 * | 10/2005 | Baldwin ............. A61M 39/223 137/625.46 |
| 6,976,974 B2 | 12/2005 | Houde et al. |
| 9,320,846 B2 * | 4/2016 | Burns .................. A61M 5/484 |
| 2002/0151854 A1* | 10/2002 | Duchon ............. A61M 31/005 604/152 |
| 2003/0195478 A1 | 10/2003 | Russo |
| 2007/0156104 A1* | 7/2007 | Lockwood ............ A61M 1/90 604/174 |
| 2009/0099552 A1* | 4/2009 | Levy .................... A61M 39/10 604/533 |
| 2009/0182309 A1* | 7/2009 | Muffly ................ A61M 39/165 604/535 |
| 2009/0221989 A1 | 9/2009 | Najafi et al. |
| 2010/0185040 A1* | 7/2010 | Uber, III ................ A61M 5/44 604/131 |
| 2010/0268118 A1* | 10/2010 | Schweiger ............ A61B 5/153 600/573 |
| 2018/0117297 A1* | 5/2018 | Allard .................. A61M 39/223 |

\* cited by examiner

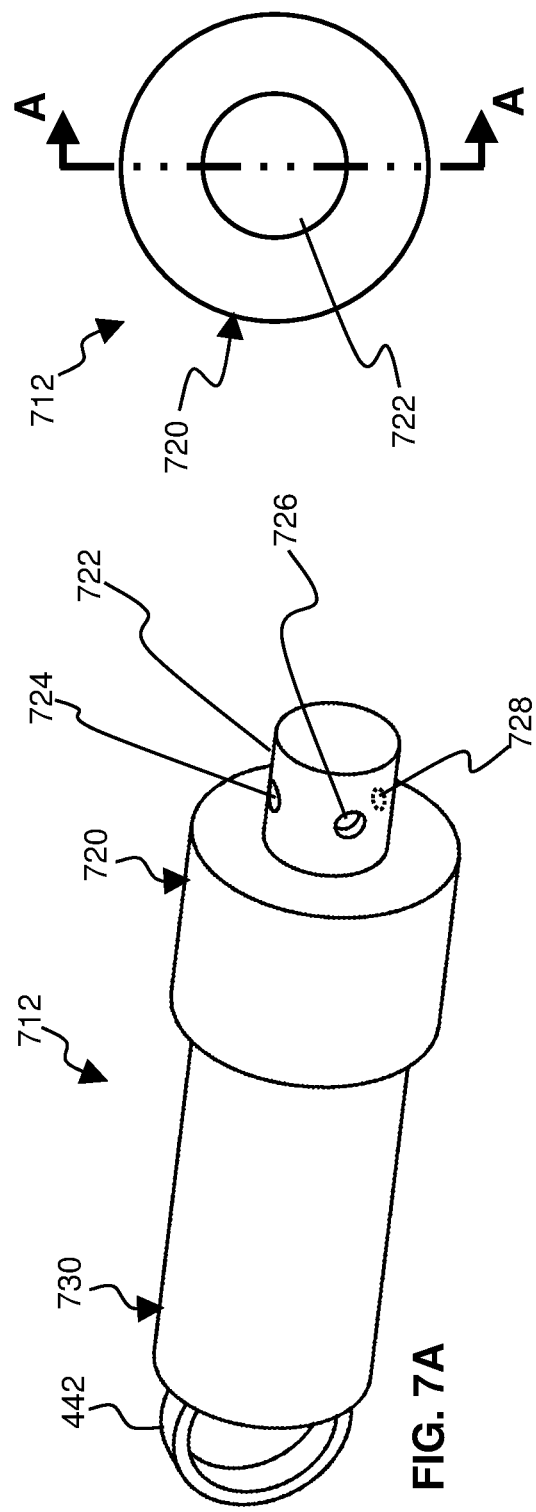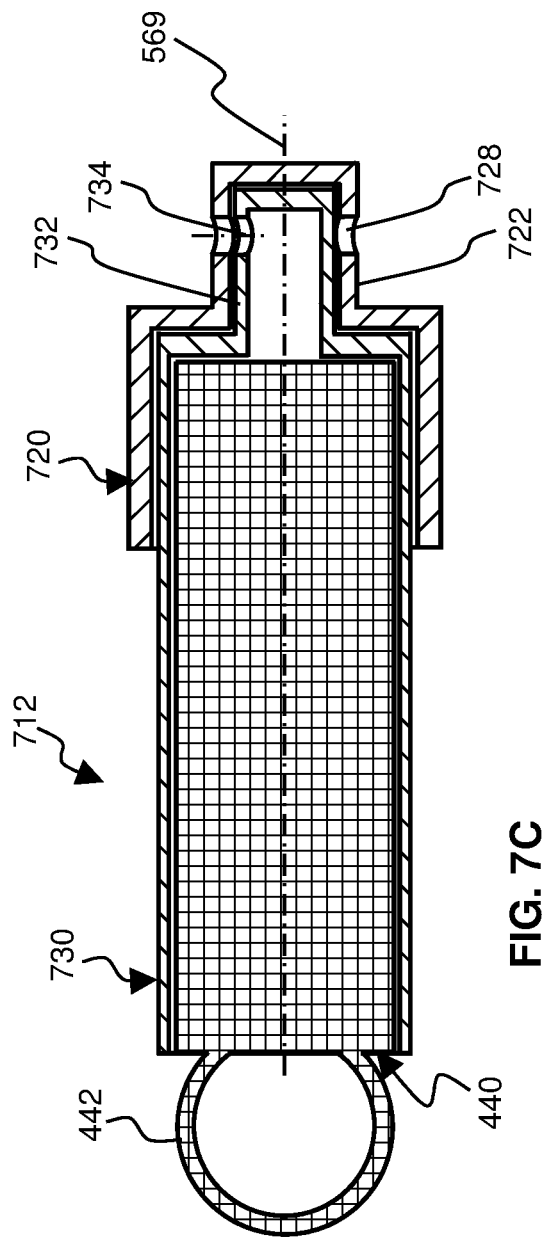

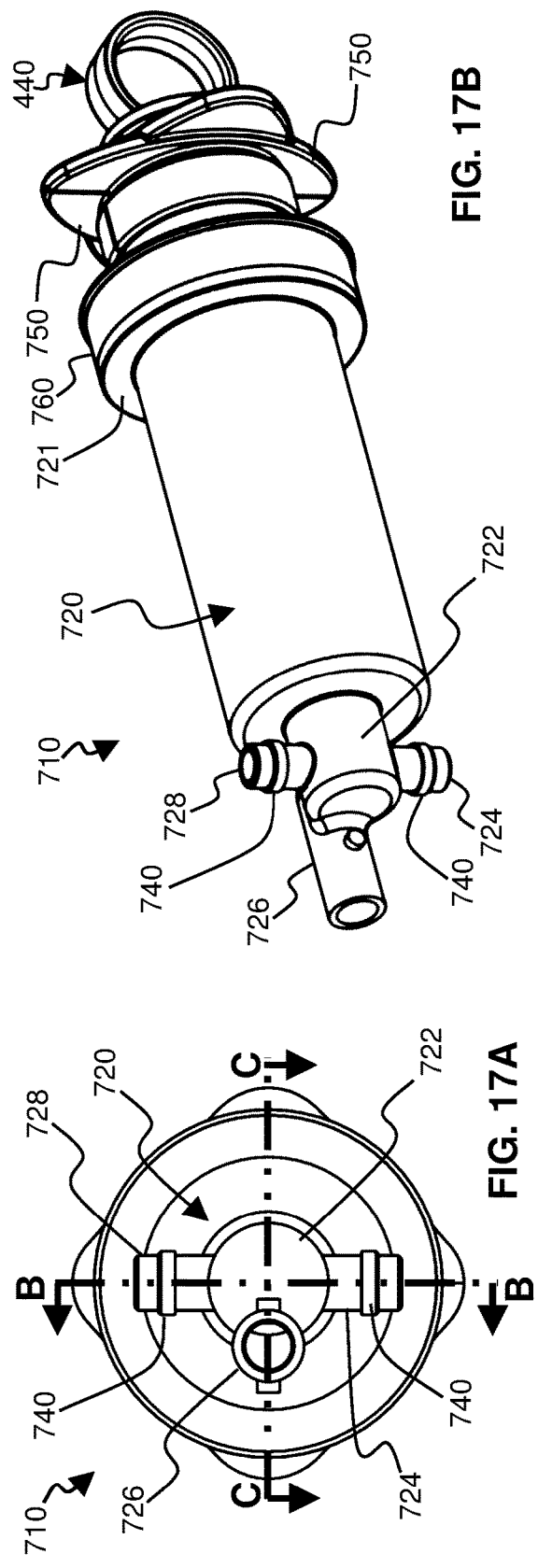
FIG. 17B
FIG. 17A
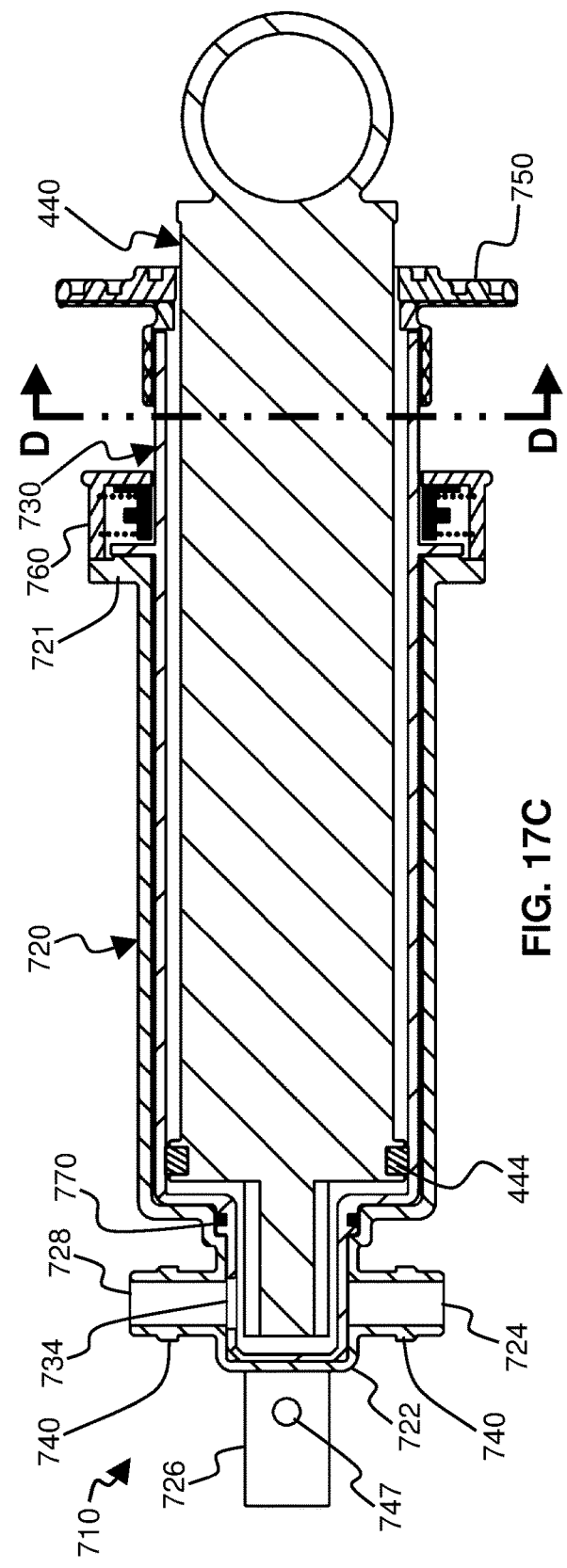
FIG. 17C

MULTI-PORT SYRINGE SYSTEM AND METHOD FOR USE WITH A URINARY CATHETER

This application is a continuation-in-part of U.S. patent application Ser. No. 15/822,103 filed 24 Nov. 2017, which claims benefit of U.S. Provisional Patent Application Ser. No. 62/426,583 filed 27 Nov. 2016, the entire disclosure of which is incorporated by reference herein.

BACKGROUND

The present invention relates to systems and methods for irrigation and/or drainage of an open or closed body cavity in human or veterinary medicine using a syringe having at least three selectable ports to allow multiple phases of an irrigation process to be performed in a closed system. Such a multiphase syringe system and method can be used in conjunction with an indwelling urinary catheter that is passed through the urethra or the abdomen into the bladder. It could be used for gastrointestinal purposes for nasogastric tube irrigation, medical feeding and rectal tube applications. It could also be used in other medical applications that require irrigations, infusions, instillation, or drainage of various materials or medications.

In the medical field, irrigation of various body cavities is used to introduce medical therapy or remove/drain various matter such as blood products, mucous, gastrointestinal material, abscess fluid, ear wax, and genitourinary material. Urinary tract surgeries, such as prostate surgery or transurethral resection, typically require the insertion of an indwelling urinary catheter to irrigate and drain the bladder. One example of a device that can be used in such surgical procedures is a urinary catheter. A suprapubic catheter that is inserted through the abdomen into the bladder is another example. Cavities other than the bladder can be irrigated, drained, and/or instilled with other medical therapies in a similar fashion. One example would be nasogastric intubation into the stomach.

Catheters can have multiple lumens (i.e. channels) connecting a body cavity with the outside world. For example, when using a two-lumen urinary catheter for irrigation, one lumen is used for inflating an internal retention balloon and a second lumen is for irrigation and drainage. In this configuration, one end of the second lumen would be located in the body cavity and the other end would typically be detachably connected to a manually operated piston syringe for filling, instilling, irrigation, and drainage—a process known as manual (or hand) irrigation. The manual irrigation process typically involves the following steps:

(a) filling the syringe with an irrigating (clean or sterile) solution by placing the tip of the syringe into a container of the solution while manually retracting the piston;

(b) placing the tip of the syringe onto the end of the second lumen of the catheter;

(c) filling the bladder with the irrigating solution by emptying the contents of the syringe into the cavity;

(d) using the syringe to withdraw the material to be flushed (irrigating solution plus blood clots, debris, purulent material, and/or accumulated body tissue) from the bladder;

(e) removing the syringe from the second lumen of the catheter;

(f) emptying the bladder contents from the syringe into a waste container; and (g) repeating the process as often as necessary, which means the system is opened repeatedly, exposing the catheter lumen and the clean or sterile input fluid to environmental contaminants.

A three-lumen urinary catheter has three channels that can connect to the body cavity. In one configuration, the first lumen is used for the internal retention balloon and the second lumen can be used for performing the same manual irrigation steps that were described for the two-lumen catheter. The third lumen in this configuration can be used for continuous gravity filling of the cavity with an irrigating solution. In another configuration of a three-lumen urinary catheter, the first lumen is for the internal retention balloon, the second is for continuous gravity filling of the cavity with an irrigating solution, and the third is for continuous gravity drainage of the cavity, a configuration called continuous bladder irrigation. The three-lumen urinary catheter system could be converted from the first configuration (manual irrigation) to the second configuration (continuous irrigation) by removing the syringe and replacing it with a line for providing continuous gravity drainage.

The most common systems and methods currently used for bladder irrigation require that the system must be opened, or broken repeatedly while irrigating, or when medicine or materials need to be instilled or infused, or when a three-lumen urinary catheter must be changed from manual irrigation to continuous irrigation. Opening an irrigation circuit creates a risk of infection or contamination of the body cavity being irrigated. It can contaminate the clean input fluid source. It can also cause spillage of the input fluid source or drained material, which poses a risk of infecting or contaminating the patient, the operator performing the irrigation, and/or the surrounding equipment and facility.

It is desired to have a simple, cost-effective, and easy to-use-closed system that reduces the risk of spillage and contamination. Such a system should also maintain sterility, especially when intermittent irrigation is needed or when manual irrigation is needed during continuous irrigation. Ideally, the system would reduce (a) the risk of catheter or drain associated infections, (b) time needed to irrigate, (c) staffing time needed to clean the spillage from manual irrigation, and (d) the risk of contamination of the cavity, the tubing system, the input fluid source, the patient, any staff member, other patients, and any surrounding equipment and the facility where the system is located. A well-designed system could be left in place for an entire duration/hospitalization for intermittent manual irrigation, whether continuous irrigation is needed or not. Such a system could be used for on-demand manual irrigation with either a two-lumen or a three-lumen urinary catheter.

Vega (U.S. Pat. No. 3,990,447), Cambio (U.S. Pat. No. 4,662,868), Ryder (U.S. Pat. No. 4,784,637), and Evans (U.S. Pat. No. 5,466,228) are examples of prior art closed systems for urinary bladder irrigation. However, the configurations disclosed in these patents appear to have too many parts, which require too many seals, and too much cost to be usable as a simple cost-effective sterile disposable assembly for bladder irrigation. This is why it appears that bladder irrigation is still primarily performed using open systems.

What is needed is a simple system that uses as few parts and seals as possible, and where all key parts can be made using cost effecting manufacturing processes, such as injection molding. The system could have a manually operable plunger with a limiter and a locking mechanism that sets the plunger into a partially open position in the barrel. This locking mechanism could prevent inadvertent insertion or retraction of the plunger in the barrel. The partially open position allows for continuous drainage through the barrel. A simple, cost-effective, and easy-to-use system that doesn't need to be opened, could also be fastened to the patient or in the vicinity of the cavity to prevent tension or dislodging of the syringe from the circuit. The system could be latex free. The system could have universal application. The system could include other features such as the use of bacteriostatic or antibacterial coating on part or all of the system. The system could include a splashguard to minimize spillage if the system is accidentally opened. The system could include a catheter tip fastener that locks the catheter lumen to a catheter port or line on an irrigating device to prevent accidental dislodging of the catheter tip and urinary catheter connection.

BRIEF DESCRIPTION OF THE DRAWINGS

This disclosure is described in conjunction with the appended figures in which:

FIG. 7A is an isometric view of a syringe with radial ports on a cylindrical boss that can be used as part of the system of FIG. 4 and FIG. 9;

FIG. 7B is an end view of the syringe of FIG. 7A;

FIG. 7C shows section A-A of FIG. 7B;

FIG. 17A shows an end view of a three-radial-port on a cylindrical boss syringe that is based on the configuration illustrated in FIG. 7A, FIG. 7B, and FIG. 7C;

FIG. 17B is an isometric view of the syringe of FIG. 17A;

FIG. 17C shows section B-B of FIG. 17A;

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details. For example, those skilled in the art will know that different materials, manufacturing processes, fastening systems, configurational arrangements, and components may be substituted.

1. Definitions

For purposes of describing embodiments of the present invention and claims, a syringe is defined as a vessel with a nozzle and a piston (i.e. a plunger), bulb, bellows, or other volume-changing element for drawing in and ejecting a fluid for the purpose of cleaning or clearing a body cavity, or for introducing material into the body cavity.

For purposes of describing embodiments of the present invention and claims, a catheter is defined as a tube made of medical grade materials configured for insertion into a body cavity, duct, or vessel to provide drainage, administration of fluids or gases, irrigation and/or access by surgical instruments.

For purposes of describing embodiments of the present invention and claims, a lumen is a fluid channel within a hollow tubular structure (such as a catheter).

2. Typical Prior Art Irrigation Systems and Methods

Figure 1A:
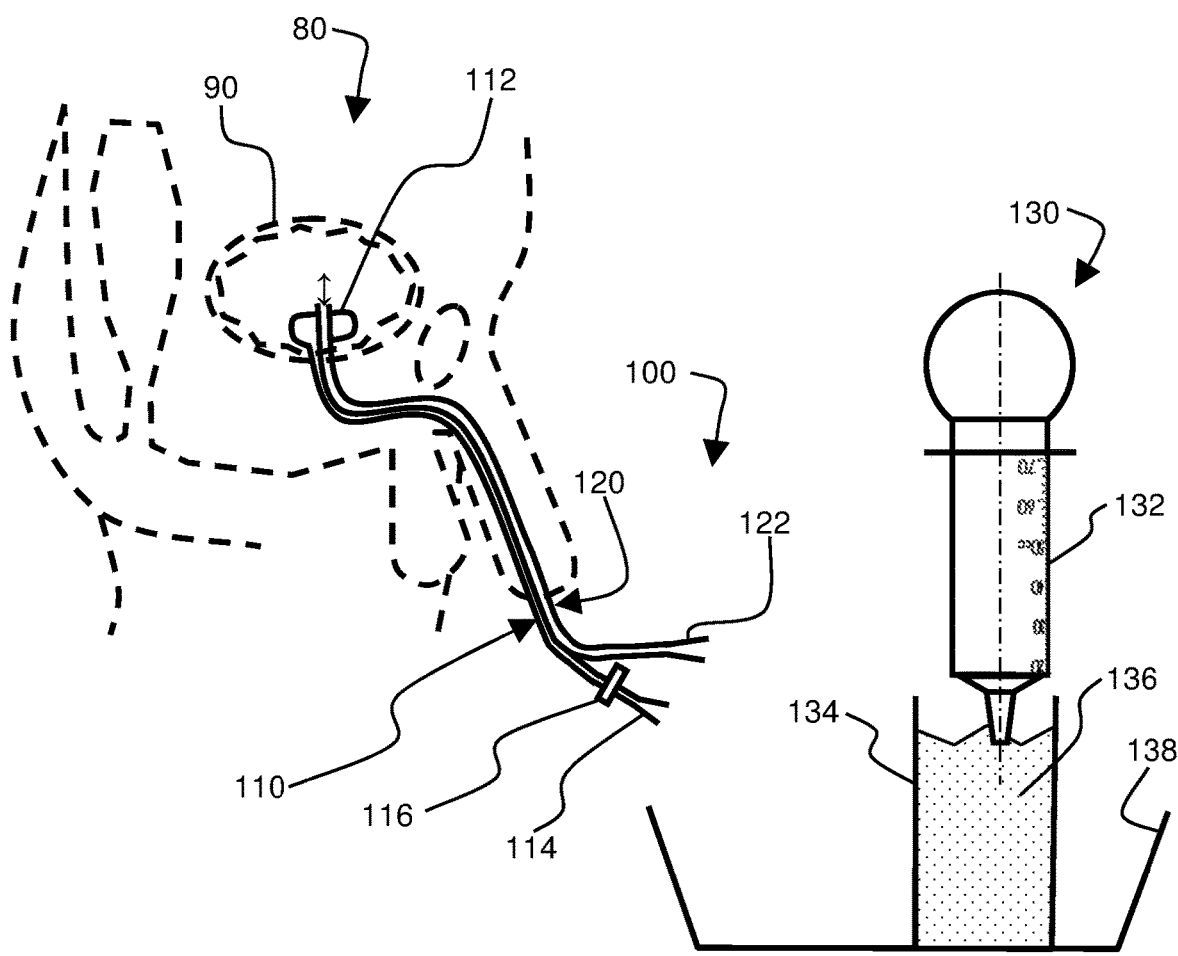
FIG. 1A shows a prior art open system for manual bladder irrigation and drainage.
Figure 1B:
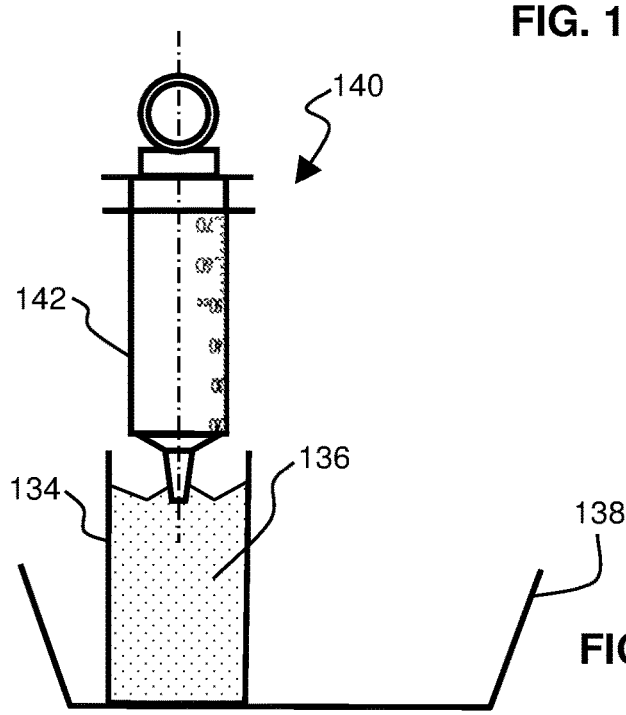
FIG. 1B shows a plunger syringe substituted for the bulb syringe of FIG. 1A.

FIG. 1A and FIG. 1B show two variations of a typical system used for manual irrigation and drainage of a bladder. These prior art systems are simple, inexpensive, and open. These systems are simple and inexpensive enough that they can be sterilized, packaged, used once, and disposed. However, these simple open systems are susceptible to spills, mixing/contaminating of the clean/sterile input fluid with bladder drainage material, and the exposure of a urinary catheter lumen 120 to the outside environment. Referring to FIG. 1A, a patient is shown in dotted lines at 80. The patient has a bladder shown at 90. In this case, the patient is a male. Embodiments of the systems and methods shown here and in other figures could also be used on female patients or in animals and they could be used for other body cavities, in configurations capable of being understood by anyone skilled in the art.

FIG. 1A shows a two-lumen urinary catheter 100 and a manual irrigation kit that uses a bulb syringe 130. FIG. 1B shows a manual irrigation kit that uses a plunger-type syringe 140. The two-lumen catheter 100 of FIG. 1A comprises a balloon inflation lumen 110 and an irrigation lumen 120. The balloon inflation lumen 110 comprises a urinary catheter balloon 112, a balloon inflation port 114, and a balloon inflation clamp 116. The irrigation lumen 120 comprises an irrigation port 122. The two-lumen urinary catheter 100 is inserted into the bladder 90 of the patient 80 and held in place by inflating a urinary catheter balloon 112 through the balloon inflation lumen 110, by inserting a fluid through the balloon inflation port 114, and then holding the fluid in the balloon 112 by the balloon inflation valve 116. The urinary catheter balloon 112 helps to hold the two-lumen urinary catheter 100 in place in the bladder 90. The second lumen of the two-lumen urinary catheter 100 is an irrigation lumen 120 that serves as a hand (or manual) irrigation and drainage channel between the bladder 90 and anything in the outside world that may be attached to it.

Further referring to FIG. 1A and FIG. 1B, the manual irrigation kit 130 or 140 comprises a bulb syringe 132 or a plunger syringe 142, an input fluid reservoir 134 with a clean or sterile input fluid 136, and a drainage tray 138. The syringe could be any manually operated vessel for drawing in and pumping out fluid such as the bulb syringe shown at 132 in FIG. 1A, a plunger-type syringe, shown at 142 in FIG. 1B, a syringe that uses bellows, or any other vessel for pumping a fluid capable of being understood by anyone skilled in the art. It should be noted that the syringes 132 and 142 used in the prior art shown in FIG. 1A and FIG. 1B have only one port for receiving and ejecting a fluid. The two-lumen catheter 100 of FIG. 1A and the manual irrigation kits (130 of FIG. 1A or 140 of FIG. 1B) are typically each purchased as sterile disposable items. The catheter 100 of FIG. 1A can be used in a patient for an extended period of time. Many irrigation kits (130 and 140) might be used as input fluid is consumed and as effluent from the bladder needs to be disposed. The input fluid reservoir 134 and the waste container 138 are open vessels that can easily be contaminated or spilled. The syringe (132 of FIG. 1A or 142 of FIG. 1B) must be attached and detached from the irrigation port 122 to manually irrigate and drain the bladder. This means that the irrigation system must be opened and closed frequently. It means that the bladder 90 can easily be exposed to the external environment. It also means that bladder contents can potentially contaminate the operator, patient, and surrounding equipment and facility.

Figure 2:
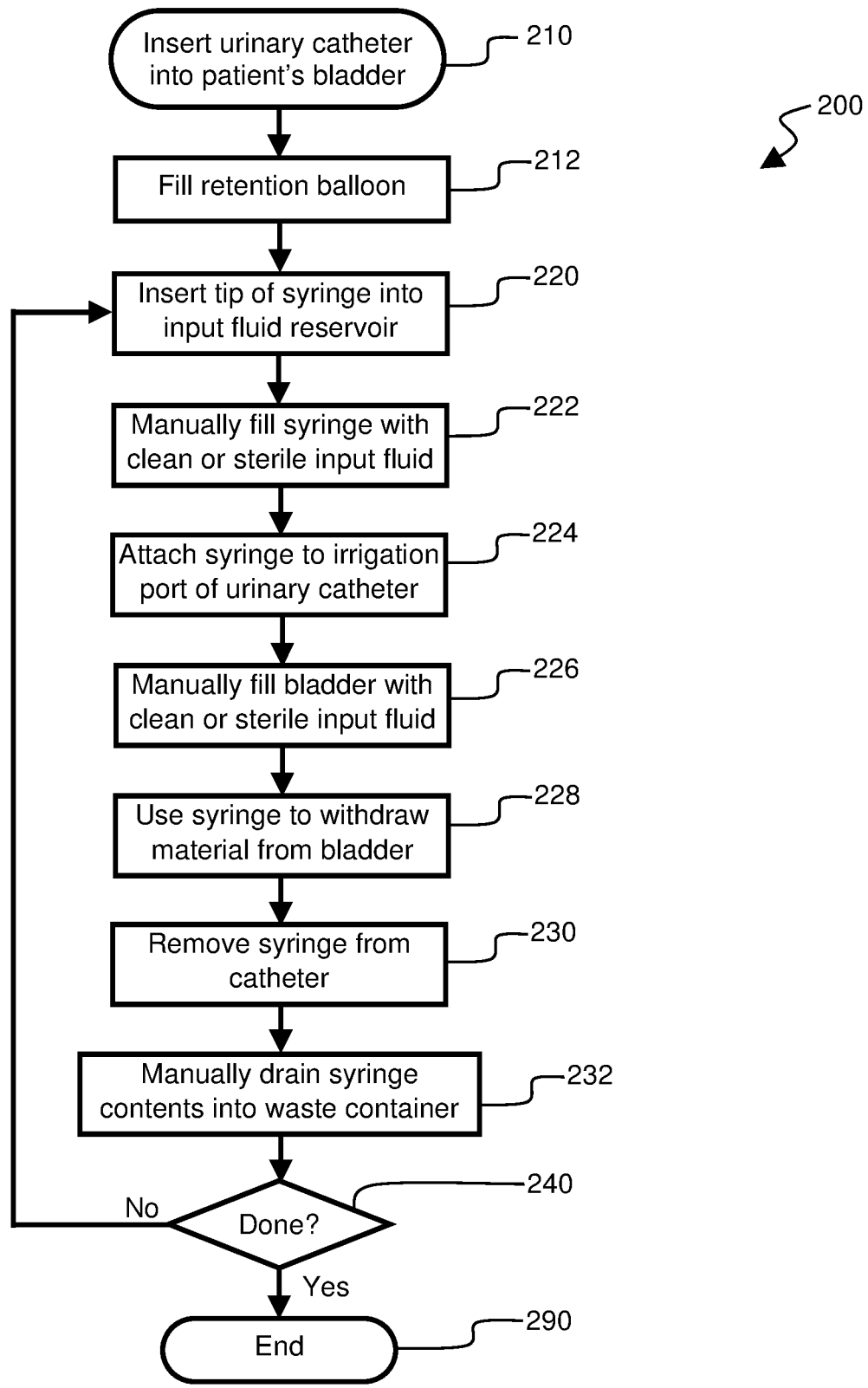
FIG. 2 provides a flowchart of a method for using the system of FIG. 1A or FIG. 1B.

The prior art shown in FIG. 1A and FIG. 1B, can be operated by using the prior art open system manual irrigation method shown at 200 in FIG. 2. This process begins by inserting a urinary catheter into the patient, a step shown at 210. Then the retention balloon is filled 212, which retains one end of the catheter in the bladder. The tip of the syringe (132 in FIG. 1A or 142 in FIG. 1B) is then inserted into an input fluid reservoir, a step shown at 220. The syringe (132 in FIG. 1A or 142 in FIG. 1B) is then manually filled with clean or sterile input fluid, a step shown at 222. This process of filling the syringe depends upon the type of syringe being used. The syringe is then attached to the irrigation port of the urinary catheter 224 and the bladder is then manually filled with the clean or sterile fluid that is in the syringe 226. At that point, the syringe could be removed from the irrigation port of the urinary catheter (a step not shown in FIG. 2) and more irrigation solution added to the bladder by repeating steps 220, 222, 224, and 226, or the syringe could be used to withdraw material from the bladder, as shown in step 228. The material removed from the bladder in step 228 can be a combination of irrigating solution and material to be removed from the bladder, such as blood clots, debris, accumulated body tissue, etc. This material fills the syringe. The syringe (132 in FIG. 1A or 142 in FIG. 1B) is then removed from the catheter, as shown at 230, and the contents of the syringe are then drained into the waste container, typically by reducing the volume of the syringe. The sequence from step 220 to step 232 is repeated as many times as necessary until the hand irrigation is done, as shown by the decision box 240. Once hand irrigation is done, the hand irrigation process ends, as shown in step 290.

Figure 3:
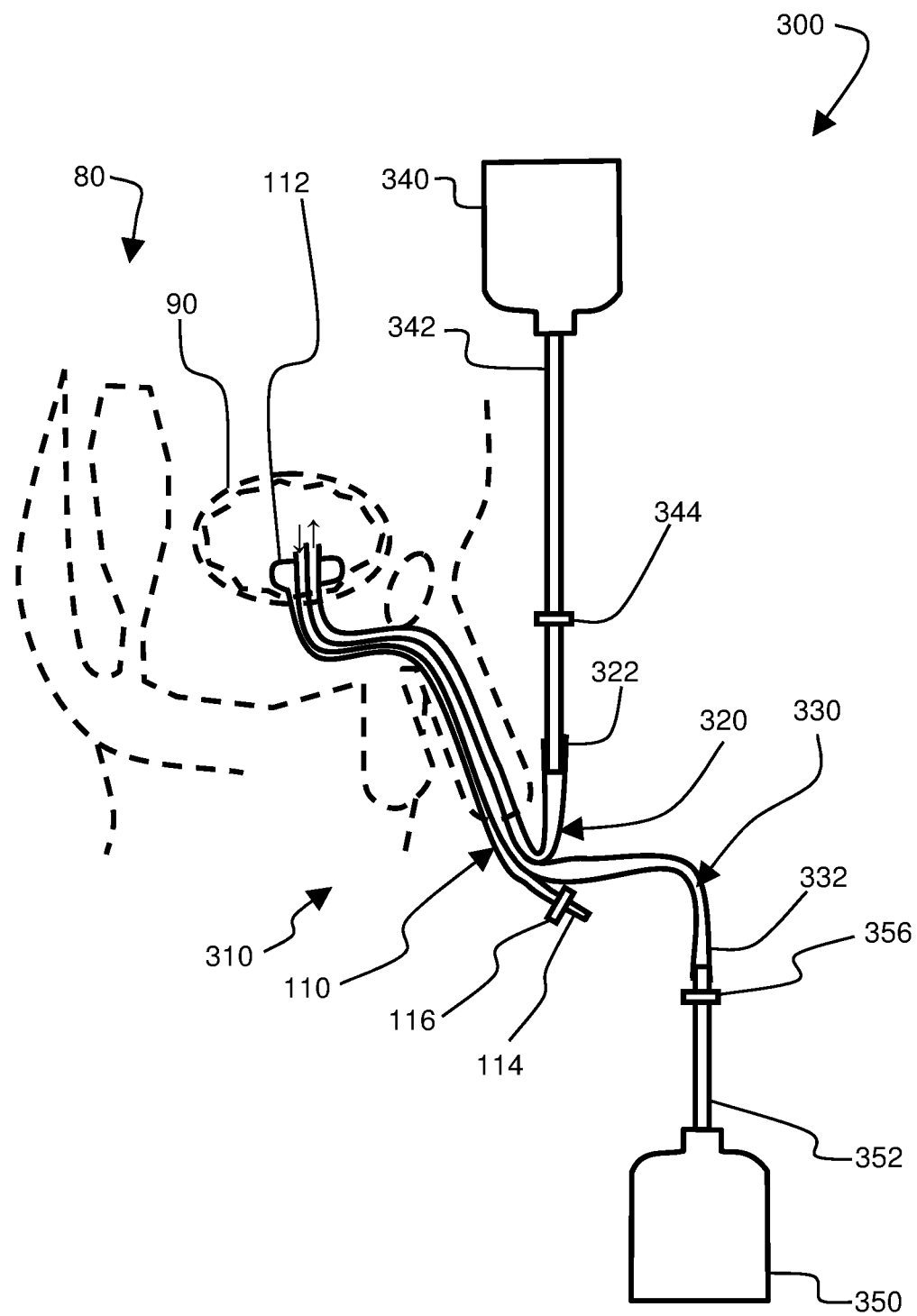
FIG. 3 shows a prior art system for continuous bladder irrigation (i.e. continuous gravity filling and drainage)

Once the hand irrigation process ends, continuous gravity irrigation can be used to continue the irrigation process. In the prior art, this required using a three-lumen urinary catheter and reconfiguring the connections to that shown in FIG. 3. Referring to FIG. 3, the same patient and bladder are shown at 80 and 90, respectively. A continuous gravity irrigation system is shown at 300. This system 300 uses a three-lumen urinary catheter, shown at 310. The three-lumen catheter 310 comprises a balloon inflation lumen 110, an input fluid lumen 320 and a drainage lumen 330. The balloon inflation lumen comprises the same urinary catheter balloon 112, balloon inflation port 114, and balloon inflation valve 116 that were illustrated in FIG. 1A and FIG. 1B. The input fluid lumen 320 comprises an input fluid port 322. The drainage lumen 330 comprises a drainage lumen port 332.

Further referring to FIG. 3, an input fluid source 340 is attached to the input fluid port 322 using an input line (or tube) 342. An input line clamp 344 on the input line 342 can be used when the input fluid source 340 must be replaced because it is empty or to turn off or regulate the input fluid supply. Similarly, there is a drainage vessel 350 attached to the drainage lumen port 332 using a drainage line (or tube) 352 and there is usually a drainage line clamp valve 356 on the drainage line 352 that can be used when the drainage vessel 350 must be replaced because it is full, or when drainage flow needs to be turned off or regulated.

3. Syringe for Closed Urinary Bladder Irrigation

Figure 4:
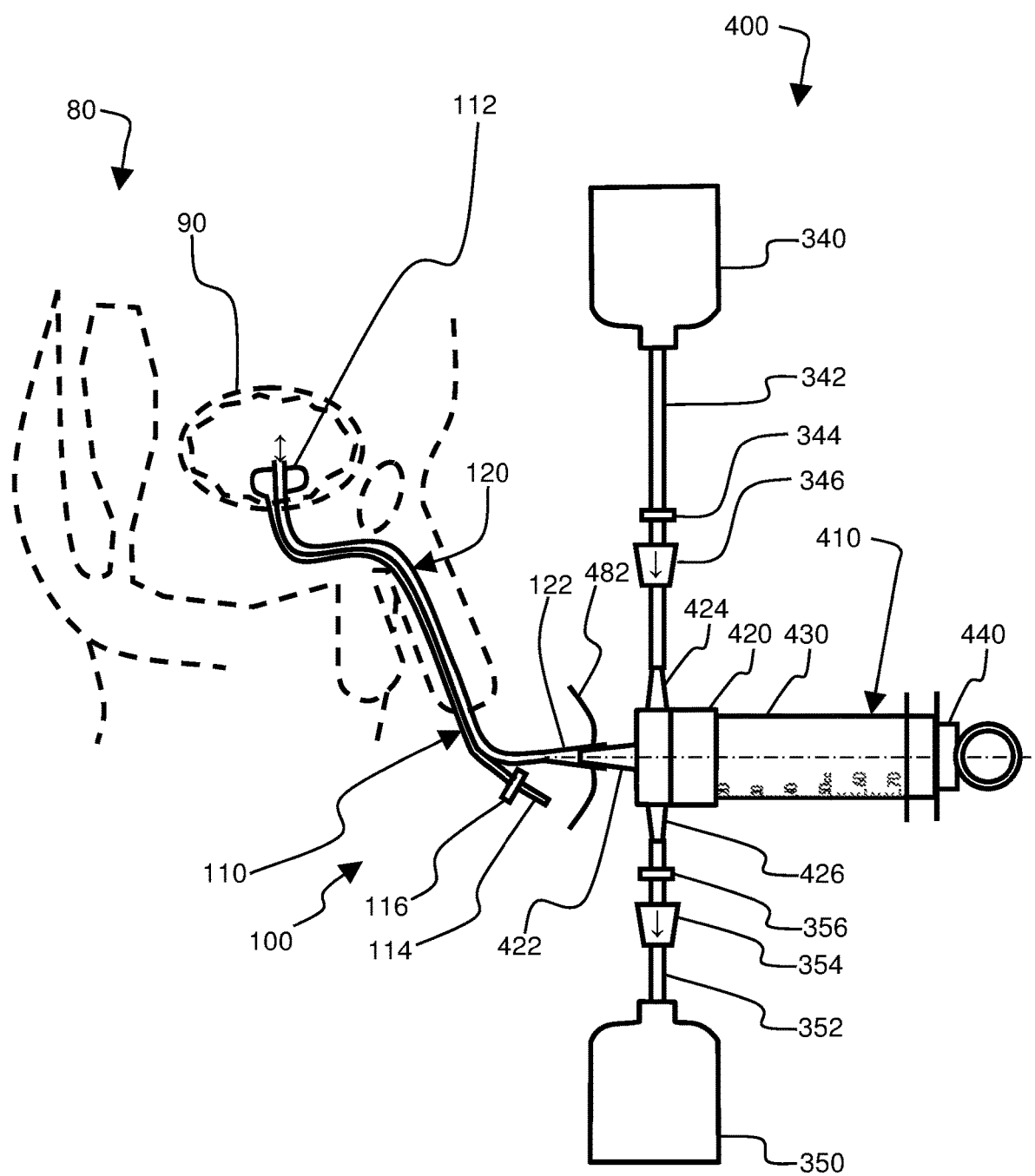
FIG. 4 shows a closed system for manual bladder irrigation and drainage.

FIG. 4 shows an embodiment of the present invention in the form of a closed system that can accomplish all of the functions that were shown and described with regard to the prior art open systems of FIG. 1A, FIG. 1B and FIG. 2. Referring to FIG. 4, a patient is shown at 80 and a closed manual irrigation system is shown at 400. As in the systems of FIG. 1A, FIG. 1B and FIG. 3, the patient is a male, but embodiments could also be used on female patients or in animals, in a configuration capable of being understood by anyone skilled in the art. The closed manual irrigation system 400 comprises the same two-lumen urinary catheter 100 and its various components (110, 112, 114, 116, 120, and 122) shown in FIG. 1A and FIG. 1B. Also shown in FIG. 4 are the same input fluid source 340, input fluid line 342, input line clamp valve 344, drainage vessel 350, drainage line 352, and drainage line clamp valve that were shown in FIG. 3. The system shown in FIG. 4 has an optional check valve 346 on the input line. The input line check valve 346 can prevent bladder fluids and material from contaminating the input fluid in the input fluid source 340 by preventing flow in the input fluid line 342 toward the input fluid source 340 (i.e. preventing reverse flow).

The closed system of FIG. 4 uses a three-port syringe shown at 410. The syringe 410 is simultaneously connected to an input fluid line 340, the irrigation port 122 of the catheter 100, and a drainage line 352. The three-port syringe 410 comprises a port body, shown at 420, a syringe barrel, shown at 430, and a syringe plunger, shown at 440. The syringe port body 420 comprises three ports: a catheter port 422 that connects to the irrigation port 122; an input port 424 that connects to the input fluid line 342; and a drainage port 426 that connects to the drainage line 352. The syringe barrel 430 can rotate inside the syringe port body 420 to select which of the three ports (422, 424, or 426) to connect to the hollow interior of the syringe barrel 430, as will be described and illustrated in more detail later. The syringe plunger 440 can slide inside the syringe barrel 430 to pump fluid in or out through the selected port (422, 424, or 426) as will be described and illustrated in more detail later.

Further referring to FIG. 4, the flow in the input fluid line 342 should be in only one direction, away from the input fluid source 340. This can be controlled by an optional input fluid check valve 346 placed in the input fluid line. The flow of fluid from the input fluid source 340 through the input fluid line 342 should occur when:
  (a) the syringe barrel 430 has been rotated inside the port body 420 to a position that provides a fluid path between the input port 424 and the interior of the barrel 430;
  (b) the input line clamp valve 344 is open; and
  (c) the plunger 440 is moved in a direction that increases the enclosed interior volume of the syringe barrel 430.

Fluid flow in the irrigation lumen 120 can be in two directions. This flow will occur when the syringe barrel 430 has been rotated inside the port body 430 to a position that provides a fluid path between the catheter port 422 and the interior of the barrel 430. Fluid will irrigate the bladder 90 when the plunger 440 is moved in a direction that decreases the enclosed interior volume of the syringe barrel 430. Fluid and/or material can be extracted from the bladder 90 when the plunger 440 is moved in a direction that increases the interior volume of the syringe barrel 430.

The flow in the drainage line 352 should only be in one direction, away from the multi-port syringe 410. This can be controlled by an optional drainage check valve, shown at 354. The drainage check valve 354 prevents reverse fluid flow in the drainage line 352 from the waste vessel 350 to the syringe 410. Normal fluid flow in the drainage line 352 should occur when the syringe barrel 430 has been rotated inside the port body 420 to a position that provides a fluid path between the drainage port 426 and the interior of the barrel 430 as the plunger 440 is moved in a direction that decreases the interior volume of the syringe barrel.

FIG. 4 also shows an optional splash shield (splashguard) at 482. The splash shield 482 can be mounted over the catheter port 422 and/or the irrigation port 122. The splash shield 482 can reduce the possibility that user and patient would be splashed with bodily fluids if the catheter port 422 becomes disconnected from the irrigation port 122. The splash shield 482 could be attached to a part of the urinary catheter 100 or the splash shield could be attached to a part of the syringe 410. The splash shield 482 could be permanently attached or the splash shield 482 could be user detachable.

Figure 5A:
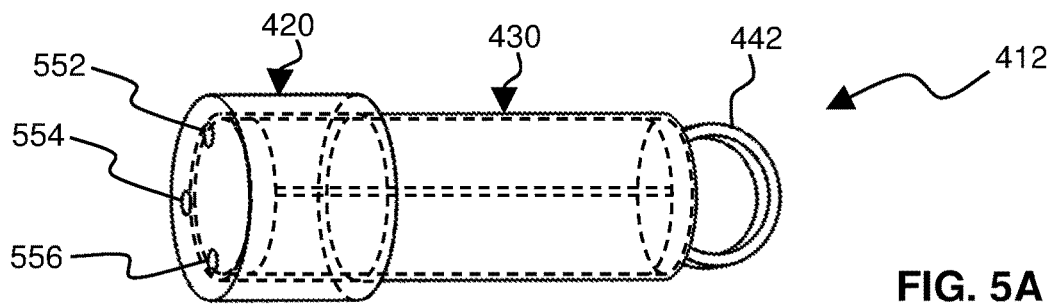
FIG. 5A is an isometric view of one configuration for an improved multi-port syringe with axial ports that can be used as part of the system of FIG. 4 and FIG. 9.
Figure 5B:
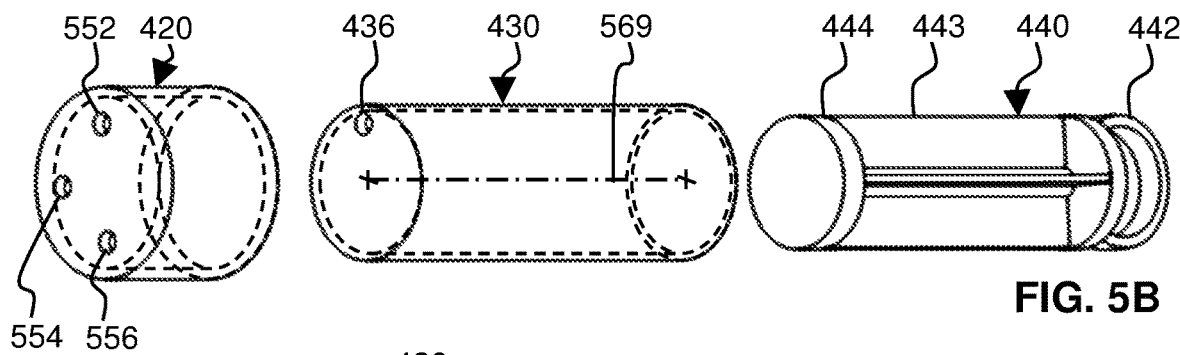
FIG. 5B is an exploded view of the syringe of FIG. 5A, with the syringe barrel in a first rotational position.
Figure 21A:
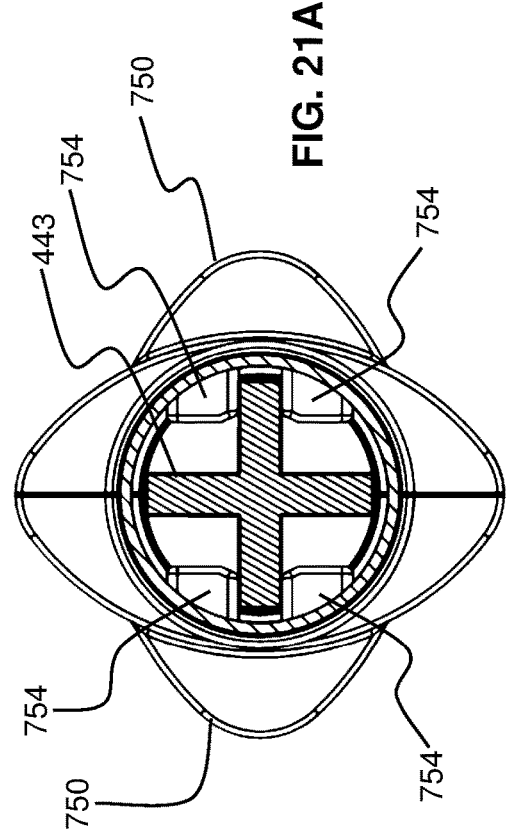
FIG. 21A and FIG. 21B show section D-D of FIG. 17C.
Figure 21B:
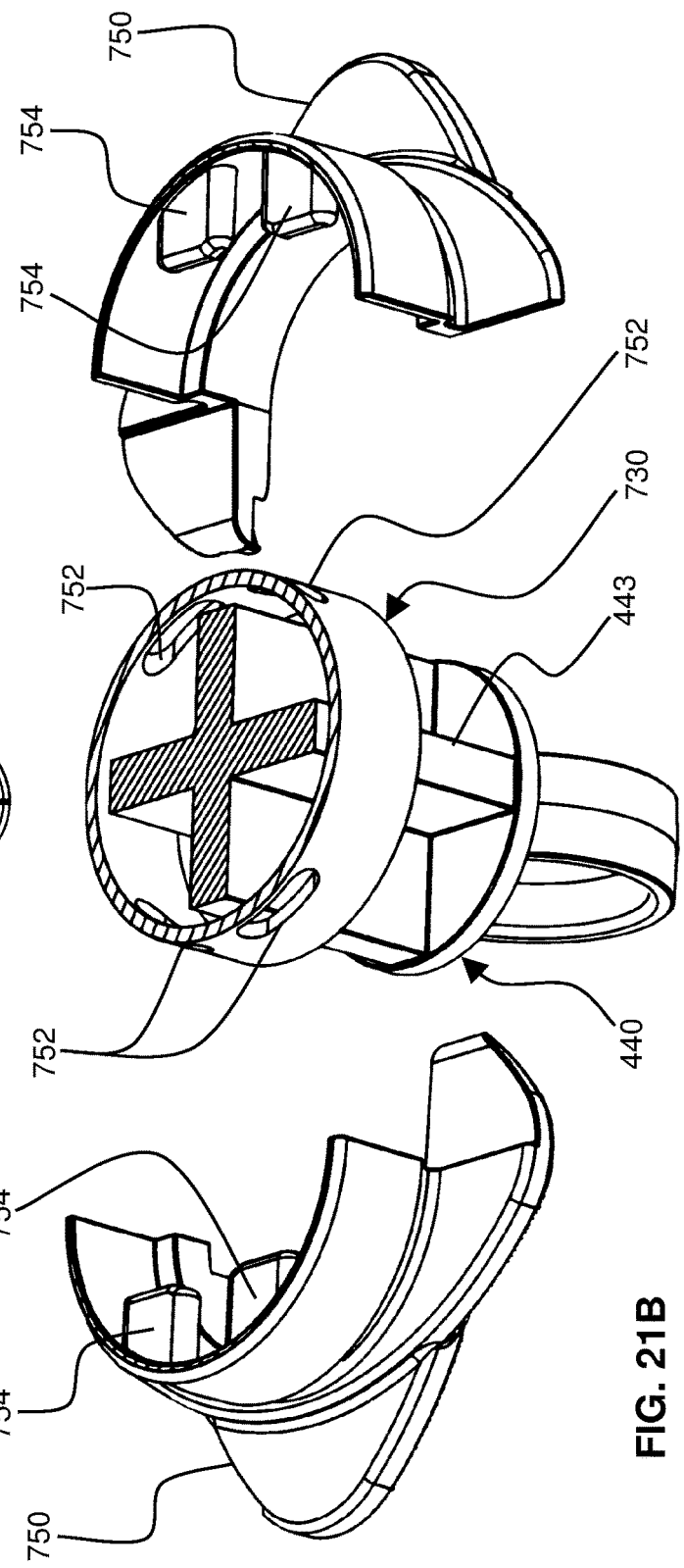

FIG. 5A shows an isometric view and FIG. 5B shows an exploded view of the key components of a simple three-axial-port syringe at 412. These key components could be used in the syringe 410, that was shown as part of the system 400 in FIG. 4. These key axial syringe components 412 are being illustrated to clarify features and configuration details of one embodiment of the invention. The three-axial-port syringe 412 comprises three main parts, each of which can be produced in high quantities using high-volume low-cost processes such as plastic injection molding, that allow these parts to be made as disposables. These key components are a port body 420, a syringe barrel 430, and a plunger 440, that were also shown in FIG. 4. The plunger 440 comprises a cylindrical (or circular) seal, shown at 444, that is configured for insertion into an open end of the syringe barrel 430 and for engagement with the cylindrical interior surface of the syringe barrel 430 to ensure that fluid in the interior of the barrel does not leak out. The plunger also comprises a grasping feature, shown at 442 that is designed for ease of manual movement of the plunger 440 inside the barrel 430 in a direction along the central axis of rotation of the barrel 569. In the embodiment shown in FIG. 5A and FIG. 5B, the plunger grasping feature 442 is a ring. There is a plunger shaft 443 that connects the plunger grasping feature to the circular plunger seal 444. In the embodiment shown in FIG. 5B, the plunger shaft 443 has a cross-shaped cross section, which will be further illustrated and described with reference to FIG. 21A and FIG. 21B. In one embodiment, the plunger seal 444 comprises an X-ring in a groove of the plunger 440.

Figure 5C:
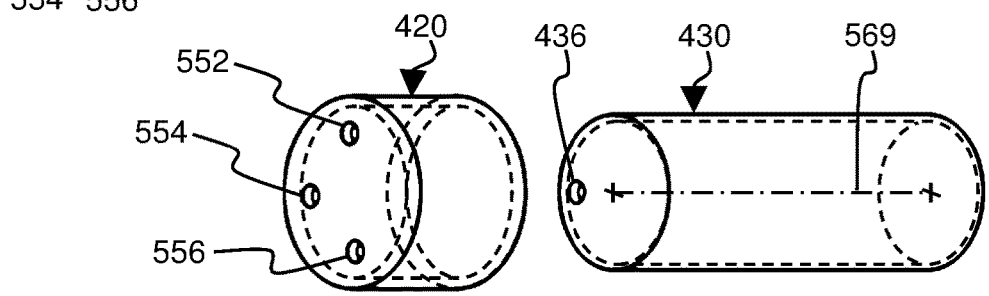
FIG. 5C is the port body and syringe barrel of FIG. 5B with the syringe barrel in a second rotational position.
Figure 5D:
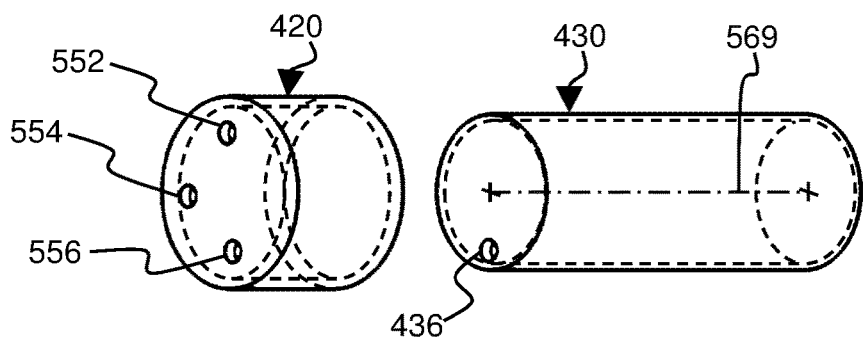
FIG. 5D is an exploded view of FIG. 5C, with the syringe barrel rotated to a third rotational position.
Figure 5E:
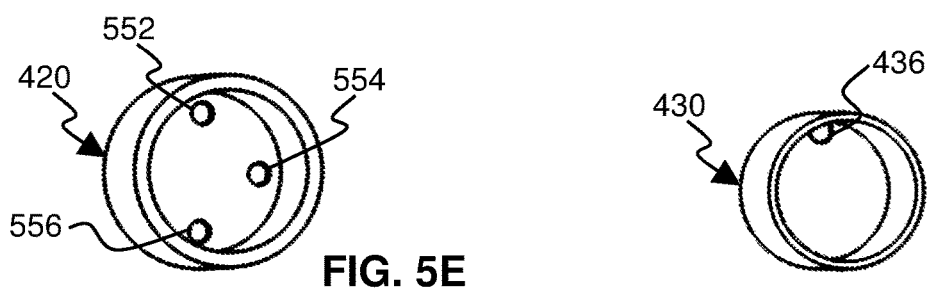
FIG. 5E shows an end view of the port body of FIG. 5A to FIG. 5D.
Figure 5F:
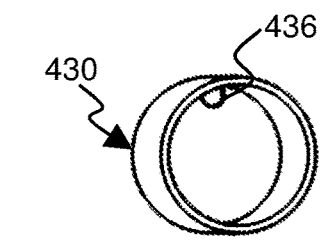
FIG. 5F shows an end view of the syringe barrel of FIG. 5A to FIG. 5D.

The syringe barrel 430, which is also shown in FIG. 5C, FIG. 5D, and FIG. 5F, comprises a thin wall cylindrical tube with an open end for insertion of the plunger seal 444 and a closed end (opposite the open end), that has a syringe barrel port 436. The syringe barrel 430 has a cylindrical interior volume between the barrel open end and the closed end. The plunger 440 can travel axially in this syringe barrel interior volume, along a barrel central axis of rotation 569, to increase or decrease the quantity of fluid stored in the interior of the syringe 412.

In the embodiment shown in FIG. 5B, FIG. 5C, FIG. 5D, and in a view looking into the syringe barrel from the open end in FIG. 5F, it can be seen that the syringe barrel port 436 is a circular aperture in the closed end of the syringe barrel 430. The syringe barrel port 436 in this embodiment is axially aligned with (i.e. a cylindrical opening with a central axis parallel to) and offset from the barrel central axis of rotation 569. This syringe barrel port 436 could also be called an axial port or an end port.

Referring to FIG. 5A to FIG. 5F, it can be understood that the barrel closed end is inserted into a cylindrical cavity of the port body 420 when the system is assembled. FIG. 5E, which is an end view of the port body 420, shows the cylindrical cavity of the port body 420. The port body shown in FIG. 5A to FIG. 5E can also be described as being shaped like a cup, or as a cylinder with a closed end and a cylindrical cavity. Thus, in the embodiment shown in FIG. 5A to FIG. 5F, both the port body 420 and the syringe barrel 430 comprise hollow cylinders with cylindrical side walls, an open end and a closed end. At least a portion of the syringe barrel 430, including the closed end, nests inside the cylindrical cavity of the port body 420. The central axis of the port body cylindrical cavity is aligned with the syringe barrel central axis of rotation 569

The end wall of the port body 420 shown in FIG. 5A to FIG. 5E has three end ports (or apertures): a first end port shown at 552; a second end port shown at 554; and a third end port shown at 556. These ports (552, 554, and 556) could also be called apertures or axial ports. In the exploded view shown in FIG. 5B, the barrel 430 is rotated to a position where the barrel end port 436 allows transmission of fluid through a first end port 552 of the port body 420, if the system were assembled. In the exploded view in FIG. 5C, the barrel 430 is rotated to a position where the barrel end port 436 allows transmission of fluid through a second end port 554 of the port body 420, if the system were assembled. In the exploded view in FIG. 5D, the barrel 430 is rotated to a position where the barrel end port 436 allows transmission of fluid through a third end port 556 of the port body, if the system were assembled. From FIGS. 5B to 5D, it should be clear that the barrel 430 is rotated about its barrel central axis, shown at 569 in order to select the first end port 552, the second end port 554, or the third end port 556 of the port body 420 for fluid transmission. Referring to FIG. 5A to FIG. 5E in conjunction with FIG. 4, the catheter port 422, input port 424, and drainage port 426 can be the same as the first axial port 552, second axial port 554, and third axial port 556 in FIG. 5A to FIG. 5E. These ports have been labeled more generically in FIG. 5A to FIG. 5E to clarify that any of the port locations shown in FIG. 5A to FIG. 5E can be assigned to any of the port functions (catheter, input, and drainage) that were identified in FIG. 4.

When viewing the illustrations shown in FIGS. 5A to 5F in combination, it should be clear that the port body 420 comprises a cylindrical cavity having an open end configured for engaging the part of the cylindrical exterior of the barrel 430 closest to the barrel closed end in a configuration wherein the barrel 430 is configured to rotate about the barrel central axis 569, inside the cavity of the port body 420 to selectively transmit fluid through one of the port body end ports (552, 554, and 556). This selective fluid transmission axial fluid flow to and/or from the interior of the syringe barrel 430 when the plunger 440 is manually moved longitudinally along the barrel central axis 569 to change the volume of fluid that is stored in the interior of the barrel 430. It should also be noted that the exterior surface of the part of the barrel cylindrical tube that is inserted into the port body cylindrical cavity should fit snugly inside the port body cylindrical cavity to facilitate rotation of the barrel in the port body and to minimize fluid leakage.

Figure 6A:
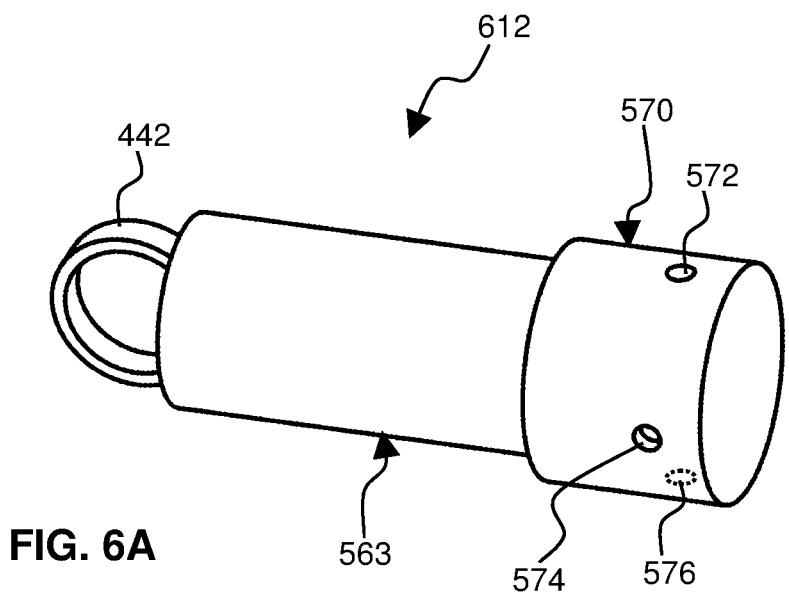
FIG. 6A is an isometric view of a multi-port syringe with radial ports that can be used as part of the system of FIG. 4 and FIG. 9.
Figure 6B:
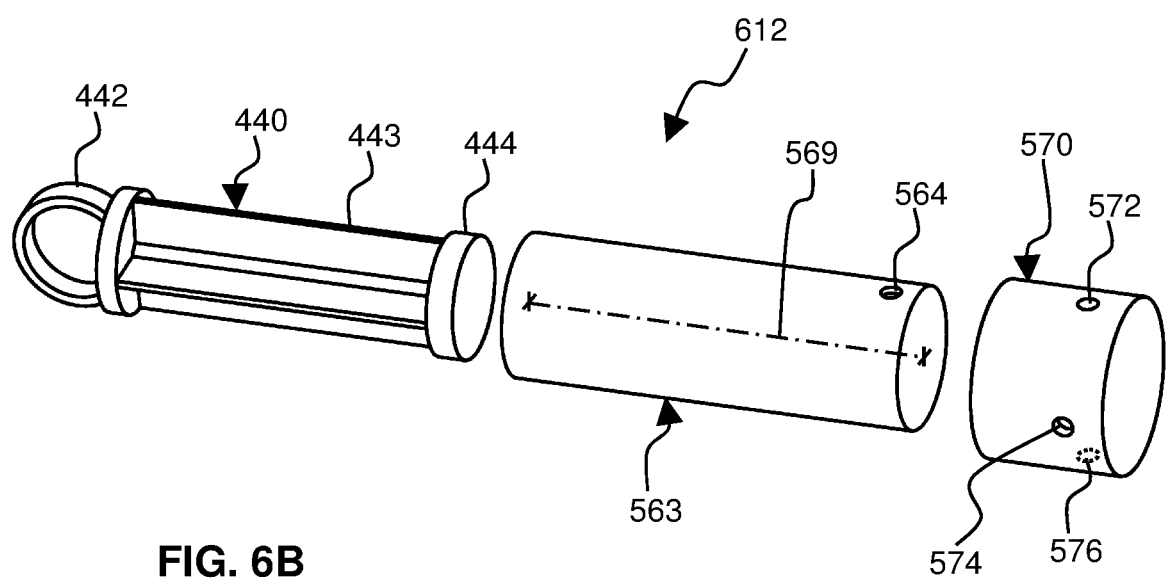
FIG. 6B shows an exploded view of the radial port syringe of FIG. 6A.

FIG. 6A shows an isometric view and FIG. 6B shows an exploded view of the key components of a simple three-radial-port syringe at 612. The radial port syringe shown at 612 is an alternate embodiment of the axial port syringe shown at 412 in FIG. 5A and FIG. 5B, and the radial port syringe 612 can be used in systems of the type shown at 400 in FIG. 4. The plunger 440, plunger grasping feature 442, plunger seal, and plunger shaft 443 are the same for both the radial port syringe 612 and the axial port syringe 412. The following is a comparison of the elements and features of the three-radial-port syringe 612 and the three-axial-port syringe:

(a) The radial port syringe 612 substitutes a radial port syringe barrel 563 that has a radial port 564, for the axial port syringe barrel 430 with its axial port 436. The radial port syringe barrel radial port 564 is a circular aperture in the cylindrical side wall of the radial port syringe barrel 563, and is located proximate to the closed end of this syringe barrel.

(b) The radial port syringe 612 substitutes a radially-ported port body 570 that comprises radially-ported port body radial ports (572, 574, and 576) for the port body end ports (552, 554, and 556) in the axial port syringe 412. These radial ports (572, 574, and 576) function the same way as the axial ports (552, 554, and 556) for the axial port syringe 412.

(c) For the embodiment shown at 612, the radial port syringe barrel radial port 564 and radially-ported port body radial ports (572, 574, and 576) comprise apertures configured for radial fluid flow, which is fluid flow in a direction perpendicular to the syringe barrel central axis 569. For the embodiment shown at 412, the axial flow syringe barrel axial port 436 and axially-ported port body axial ports (552, 554, and 556) comprise apertures configured for axial fluid flow, which is fluid flow in a direction parallel to the syringe barrel central axis 569.

FIG. 7A shows an isometric view, FIG. 7B shows an end view, and FIG. 7C shows a section view of an alternate simple three-radial-port syringe at 712. This alternate three-radial-port syringe configuration 712 can also be used in systems of the type shown at 400 in FIG. 4, instead of the multi-port configurations that were shown at 412 in FIG. 5A, or 612 in FIG. 6A. More specifically, FIG. 7C shows section A-A of FIG. 7B. The syringe system shown at 712 differs from the syringe system shown at 612 in FIG. 6A and FIG. 6B because the system shown at 712 comprises a cylindrical boss syringe barrel 730 that comprises a cylindrical boss 732 (or neck) and this cylindrical boss 732 comprises a radial port 734 (or radial aperture). The cylindrical boss 732 is centered on the syringe barrel central axis 569. The cylindrical boss 732 is configured to fit into a cylindrical receptacle in the port body cylindrical cavity. The syringe barrel cylindrical boss radial port 734 is configured to align with radial ports (724, 726, and 728) in the cylindrical boss 722 of the cylindrical boss port body, shown at 720, in a similar manner to what was shown for the radial ports in FIG. 6A and FIG. 6B. Thus, the configuration shown at 712 is also has a port body that can be described as a radially-ported (or side-ported) port body and has a syringe barrel that can also be described as a radially-ported (or side-ported) syringe barrel. It should be noted that the plunger 440 and its handle 442 can be the same in the configuration shown in FIG. 7A and FIG. 7B as for the configurations shown earlier, or the plunger 440 could also have a feature on its tip that fits into the open interior of the cylindrical boss of the syringe barrel 732 to reduce the volume of fluid in the barrel when the plunger 440 is fully inserted into the syringe barrel 732. One configuration for this plunger tip can be seen at 745 in FIG. 18 and will further described later in this document.

Figure 8:
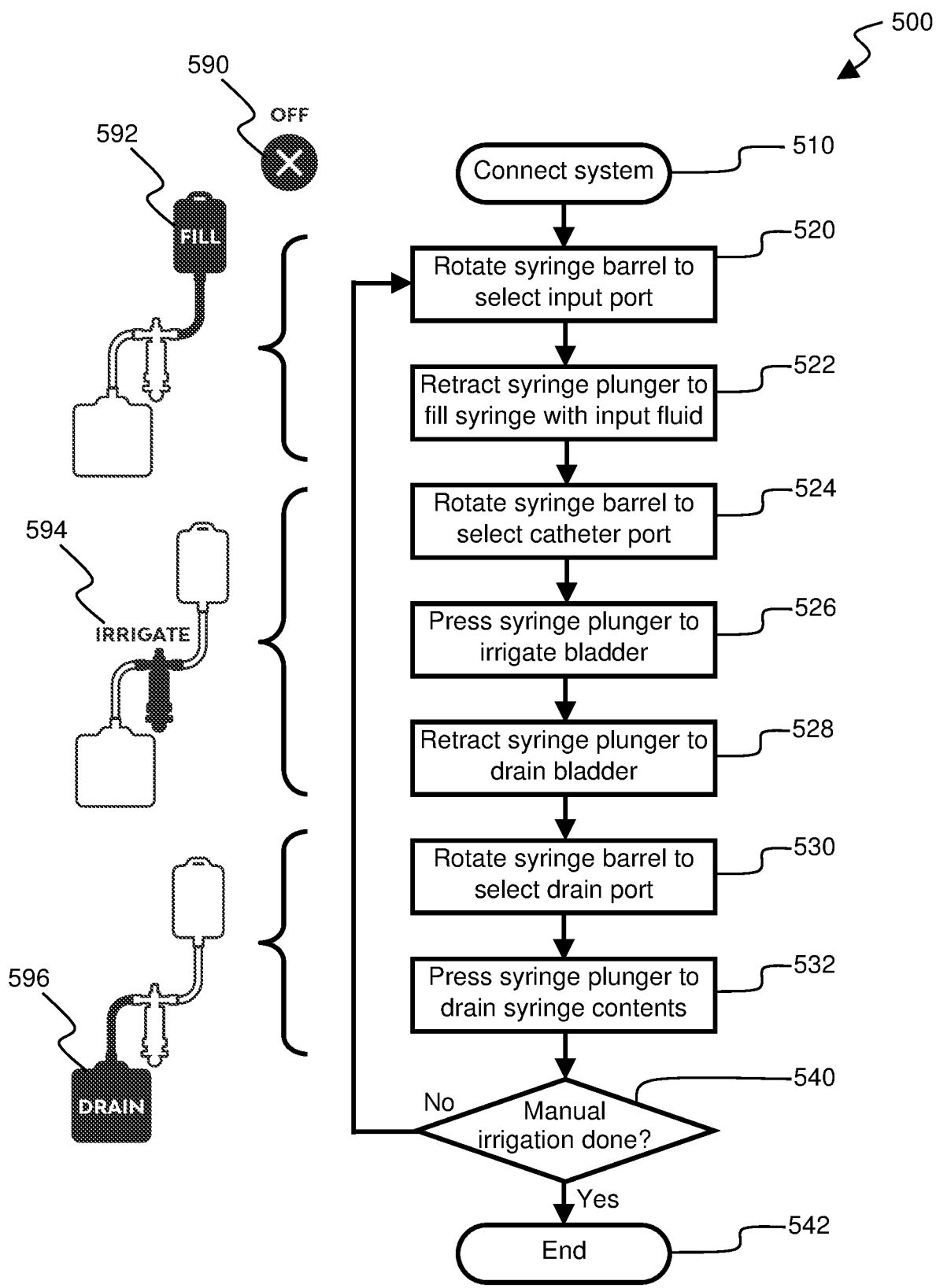
FIG. 8 shows a method for using the system illustrated in FIG. 4.

The system shown in FIG. 4 can be operated by using the manual irrigation process shown in FIG. 8. This process begins by connecting the system to the patient, shown in step 510. The syringe barrel is then rotated to select the input (or fill) port, as shown at step 520. Once the input (or fill) port has been selected 520, the syringe plunger is retracted to fill the syringe with input fluid, as shown at step 522. Then the syringe barrel is rotated to select the catheter port, a step shown at 524. With the catheter port selected 524, the syringe plunger is pressed into the syringe body to irrigate the bladder in the step shown at 526. This is followed by a retraction of the syringe plunger to drain the bladder, as shown at the step labeled 528. Next, the syringe barrel is rotated to select the drain (or drainage) port, a step shown at 530. With the drain (or drainage) port selected 530, the syringe plunger is pressed into the syringe barrel to drain the syringe contents, as shown at 532. The sequence from step 520 to step 532 is repeated as many times as necessary until the hand irrigation is done, as shown by the decision box 540. Once hand irrigation is done, the hand irrigation process ends, as shown in step 542. Once the hand irrigation process ends, continuous gravity drainage could continue if the catheter lumen 122 is directly connected to the drainage line 352.

The left side of FIG. 8 shows rotational position information that can be used to indicate which rotational position the syringe barrel is in relative to the port body. The application of this rotational position information will be further described with reference to FIG. 23. There can be four rotational positions shown by these rotational position indicators:

(a) An, off position indicator, shown at 590;
(b) A fill position indicator, for performing step 522, shown at 592;
(c) An irrigate position indicator, for performing steps 526 and 528, shown at 594; and
(d) A drain position indicator, for performing step 532, shown at 596.

Figure 9:
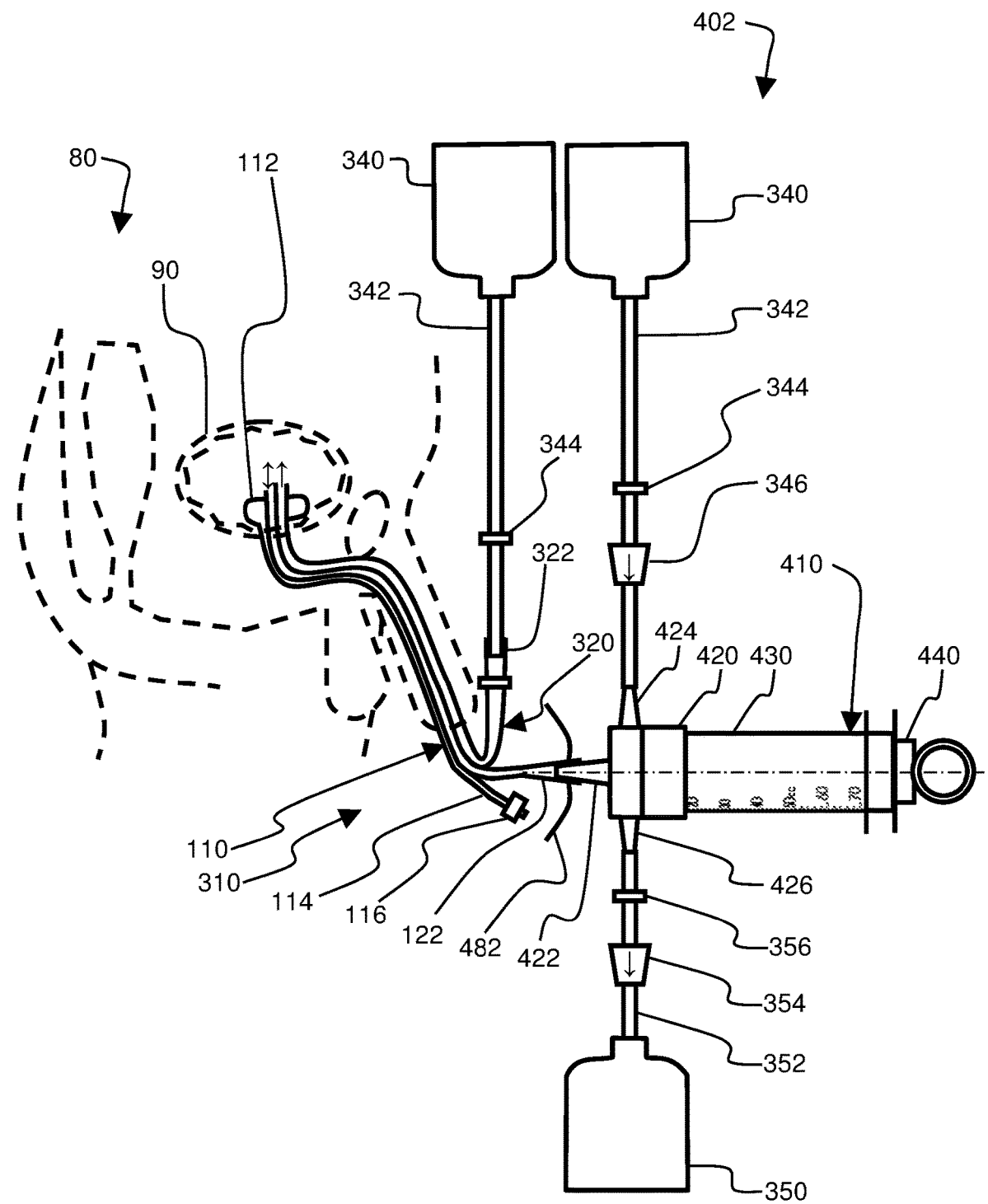
FIG. 9 shows the syringe of FIG. 4 in a system comprising a three-lumen urinary catheter wherein the third lumen is used for continuous gravity irrigation.

FIG. 9 shows an embodiment of the present invention in which components for continuous filling of the bladder with irrigation fluid that was illustrated in FIG. 3 are combined with the hand irrigation system using the 3-port syringe that was illustrated in FIG. 4. This allows the embodiment shown in FIG. 9 to be used for gravity irrigation in the same way as the system shown in FIG. 3, and for manual irrigation, manual and manual drainage in the same way as the system shown in FIG. 4, without disconnecting any line. The system shown in FIG. 9 cannot be used for continuous gravity drainage, which is one of the functions available for the system shown in FIG. 3.

Referring to FIG. 9, the components used for continuous filling of the bladder that were illustrated at 340, 342, and 344 in FIG. 3 serve the same functions in the configuration shown in FIG. 9. The system 402 in FIG. 9 can fit the same bladder 90 in the same patient 80 as the systems shown previously. The system 402 in FIG. 9 uses a three-lumen urinary catheter 310 instead of the two-lumen urinary catheter (110 in FIG. 4). In the configuration shown at 402, the input fluid lumen 320 can be used to continuously fill the bladder with irrigation fluid, just like was done in FIG. 3. An input clamp valve 344 can be used to clamp the input fluid line 342 when the input (or irrigation) fluid source 340 needs to be changed or the bladder is too full. The system shown in FIG. 9 uses the same type of balloon inflation lumen 110, urinary catheter balloon 112, balloon inflation port 114, and balloon inflation valve 116 that were shown previously. The other components in the system shown in FIG. 9 are the same as the like numbered components in the system shown in FIG. 4. It should be noted that the embodiment shown at 402 in FIG. 9 comprises two input fluid sources 340, two input fluid lines 342, and two input line clamps 344, with one set connected directly to the catheter 310 and the second set connected to the input port of the three-port syringe 400. The set connected to the input port of the three-port syringe can also comprise the optional check valve 346 that was previously shown with reference to FIG. 4.

Figure 10:
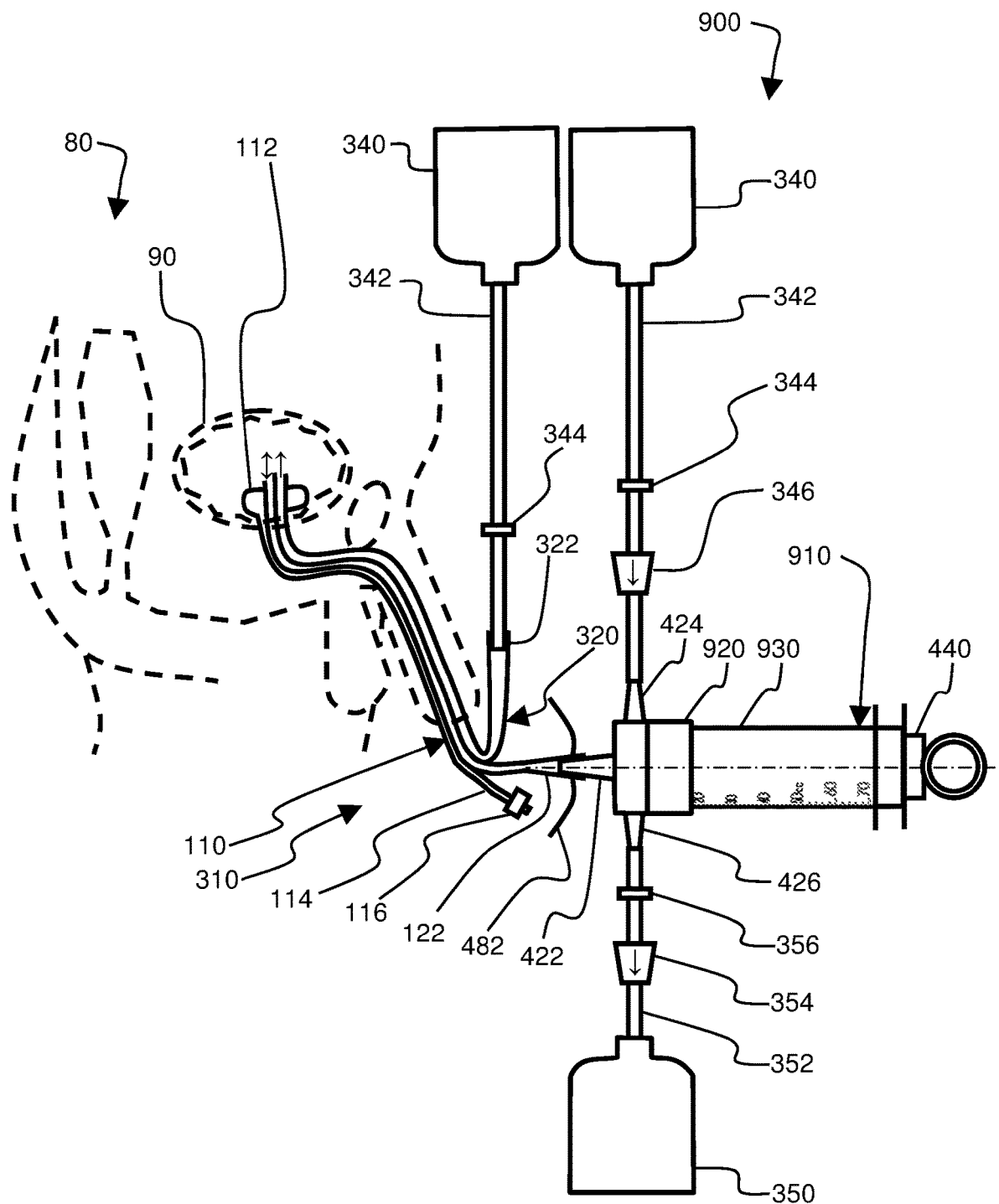
FIG. 10 shows an alternate three-port syringe, a three-lumen catheter, and two input fluid sources to combine FIG. 3 and FIG. 4 into a system with four operational phases.

FIG. 10 shows another embodiment of the invention at 900. In the embodiment shown at 900 in FIG. 10, the functions of the embodiment that was illustrated in FIG. 4 are combined with all of the functions of the continuous gravity irrigation and drainage system shown in FIG. 3 to create a single system that can perform all of the functions of these two systems without the need to connect or disconnect any ports or lines. In the embodiment shown at 900 in FIG. 10, this combination of all functions is accomplished by replacing the three-port syringe 400 of FIG. 9 with a three-port-continuous-gravity-drainage syringe that is shown at 910 in FIG. 10. This three-port-continuous-gravity-drainage syringe 910 differs from the three-port syringe, 410 in FIG. 4 and FIG. 9, by having an alternate port body 920 and an alternate syringe barrel 930 that provide an additional selectable rotational position. This additional selectable rotational position for the three-port-continuous-gravity-drainage syringe 910 can be used to configure the system 900 so that the catheter port 422 is connected to the drainage port 426 and that fluid can continuously drain from the bladder 90 of the patient 80 into the drainage vessel 130 without any hand pumping. All other components and features of the system 900 shown in FIG. 10 are the same as the equivalently numbered components and features that were illustrated in previous figures. The illustrations and descriptions for FIG. 27 and FIG. 28 further describe how the ports can be configured for this alternate three-port syringe 910.

Figure 11:
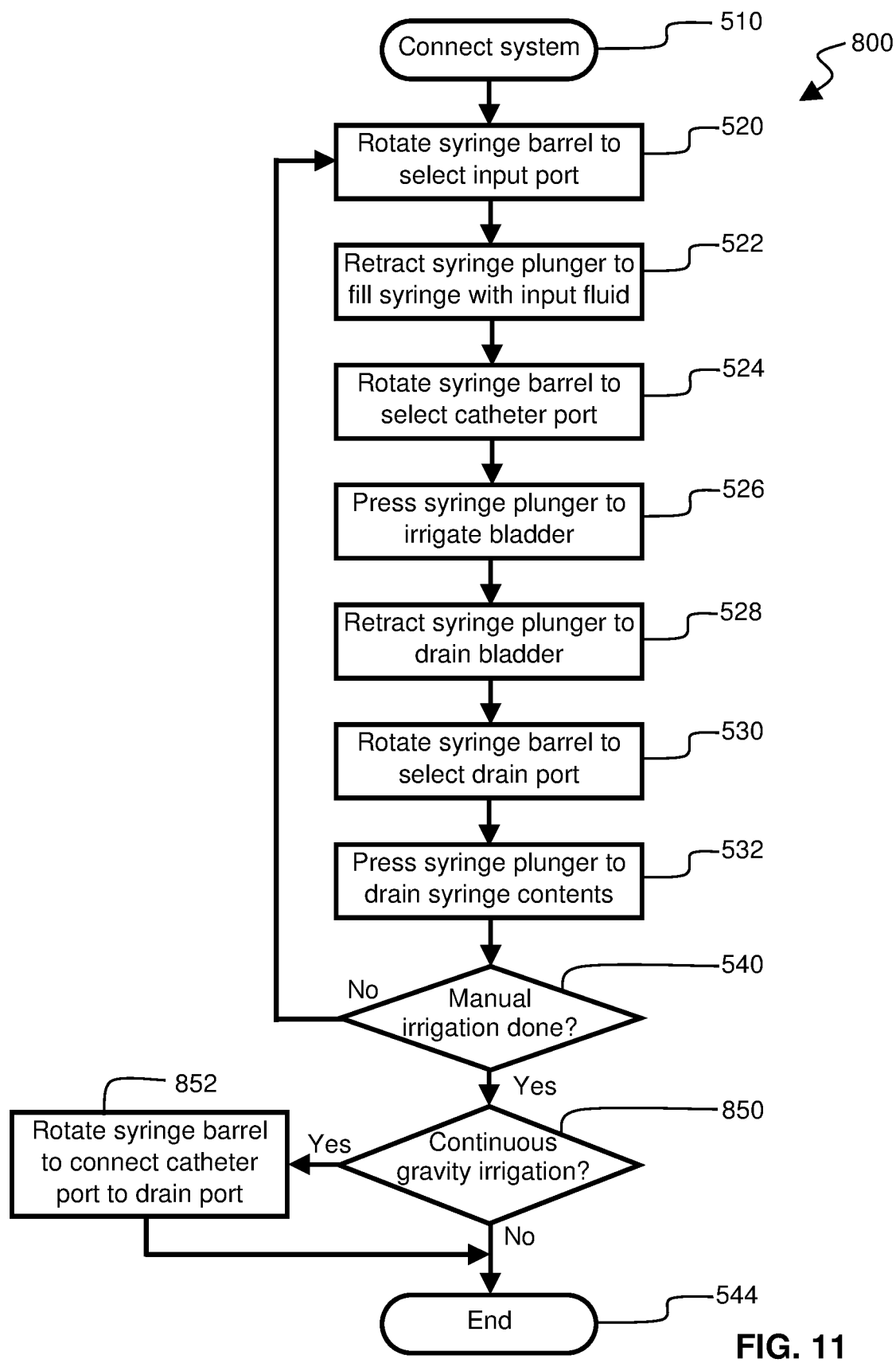
FIG. 11 provides a flowchart of a method for using the system illustrated in FIG. 10.

The system shown in FIG. 10 can be operated by using the manual irrigation process shown in FIG. 11. This process is similar to the process shown in FIG. 8 in that steps 510 to 540 are similar. Once hand irrigation is done, the operator of the system shown in FIG. 10 can choose, at step 850, to provide continuous gravity drainage, by rotating the syringe barrel to a position that connects the catheter port (422 in FIG. 10) to the drainage port (426 in FIG. 10), a step shown at 852. Connecting the catheter port (422 in FIG. 10) to the drainage port (426 in FIG. 10), in the alternate three-port syringe (910 in FIG. 10) allows continuous drainage to occur at the same time as continuous irrigation is occurring in the embodiment illustrated in FIG. 10. The process ends at 544 when continuous gravity irrigation is turned off.

Figure 12:
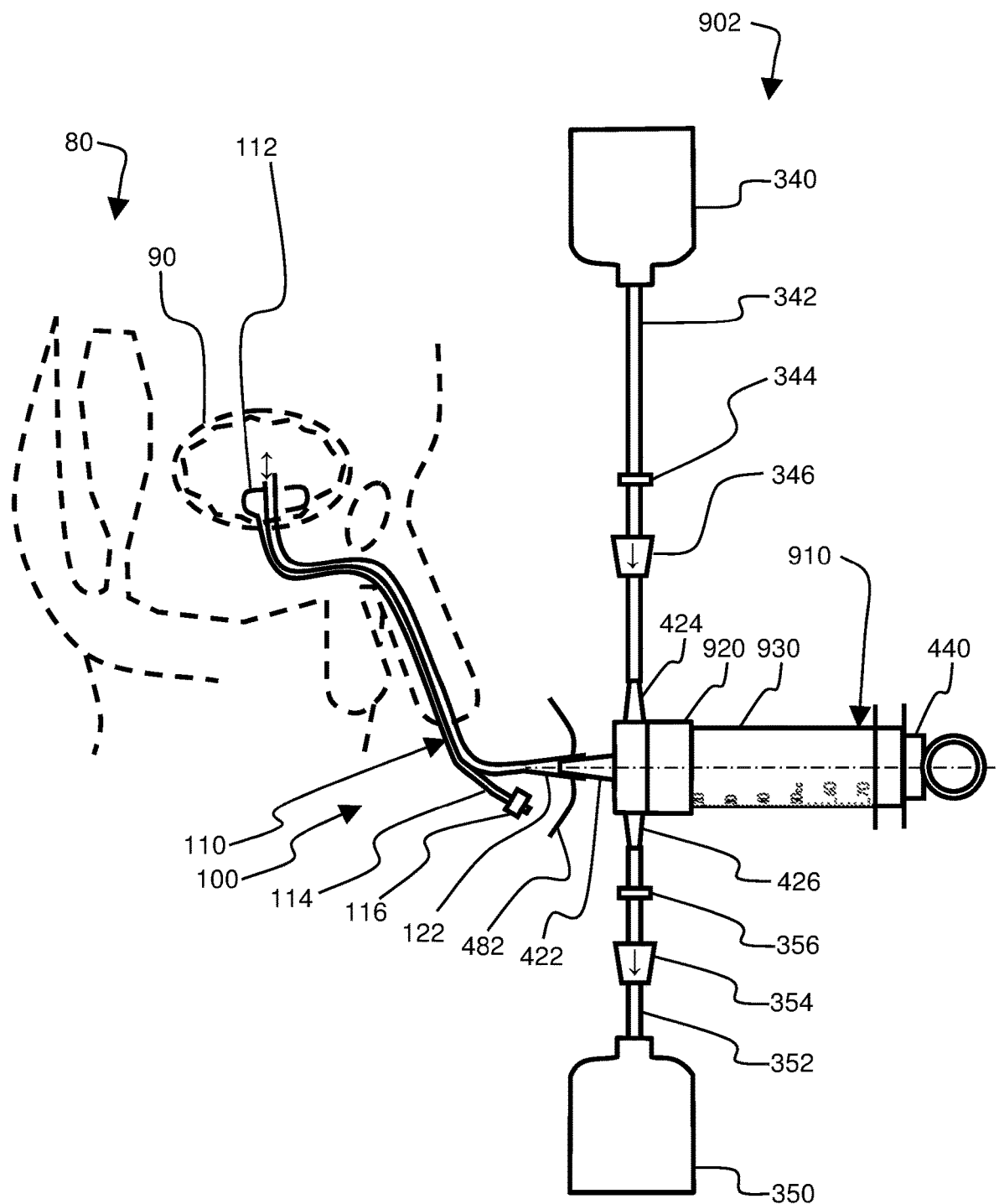
FIG. 12 shows a manual irrigation and drainage system that has four operational phases and uses the alternate 3-port syringe and a two-lumen urinary catheter.

FIG. 12 shows another embodiment of the present invention. The embodiment shown at 902 includes all of the functions of the embodiment shown in FIG. 10, except that:

(a) The three-lumen urinary catheter in FIG. 10 has been replaced with a two-lumen catheter, shown at 100; and
(b) The second input fluid source, 340 in FIG. 10, and related input fluid line 320 and input line clamp 344 are not part of the system shown at 902 in FIG. 12.

The system shown at 902 in FIG. 12 is a single system with a continuous gravity drainage function (or phase) along with the three other functions (or phases) of the system that was illustrated with reference to FIG. 4, by substituting the 3-port-continuous-gravity-drainage syringe, 910 in FIG. 10, for the 3-port syringe, 410 in FIG. 4. The system of FIG. 12 can change from a manual irrigation to continuous drainage without the need to connect or disconnect any ports or lines. All other components, features, and functionality of the system 902 shown in FIG. 12 are the same as the equivalently numbered components, features, and functionality that were described with reference to FIG. 4, FIG. 10 and FIG. 11.

The following table further clarifies the functionality differences between the embodiments shown in FIG. 3, FIG. 4, FIG. 9, FIG. 10, and FIG. 12:

|  | FIG. 3 (Prior Art) | FIG. 4 3 phases | FIG. 9 3 phases | FIG. 10 4 phases | FIG. 12 4 phases |
| --- | --- | --- | --- | --- | --- |
| Closed manual filling of syringe | No | Selectable first phase | Selectable first phase | Selectable first phase | Selectable first phase |
| Closed manual bladder filling and extraction | No | Selectable second phase | Selectable second phase | Selectable second phase | Selectable second phase |
| Closed manual drainage of syringe | No | Selectable third phase | Selectable third phase | Selectable third phase | Selectable third phase |
| Continuous gravity filling of bladder? | Yes | No | Yes | Yes | No |
| Continuous gravity drainage of bladder? | Yes | No | No | Selectable fourth phase | Selectable fourth phase |
| Syringe ports | No syringe | 3 | 3 | 3 | 3 |
| Syringe positions | No syringe | 3 | 3 | At least 4 | At least 4 |
| Catheter lumens | 3 | 2 | 3 | 3 | 2 |

Here is an additional description of some differences between the prior art (FIG. 1A, FIG. 1B, FIG. 2, and FIG. 3) and embodiments of the present invention (FIG. 4, FIG. 8, FIG. 9, FIG. 10, FIG. 11, and FIG. 12):
(a) The prior art is systems and methods for manual irrigation and/or gravity filling and drainage that require the system to be opened. Embodiments of the present invention are closed systems and methods for manual irrigation, that can also include a fourth phase for gravity drainage. This fourth phase could be implemented using a fourth selectable syringe position and this fourth syringe position could be selected without needing to open the system.
(b) The prior art illustrated in FIG. 3 does not include any manual irrigation or any syringe.
(c) The three syringe ports in the systems of FIG. 4, FIG. 9, FIG. 10, and FIG. 12 connect to an input fluid source (340 in FIG. 4, FIG. 9, and FIG. 10, which is also called the "Fill" port), a catheter (100 in FIG. 4 and FIG. 12, or 310 in FIG. 9 and FIG. 10), and a drainage vessel (350 in FIG. 4, FIG. 9, FIG. 10, and FIG. 12).

4. Detailed Description of a 3-Axial-Port 3-Position Syringe Embodiment

Figure 13:
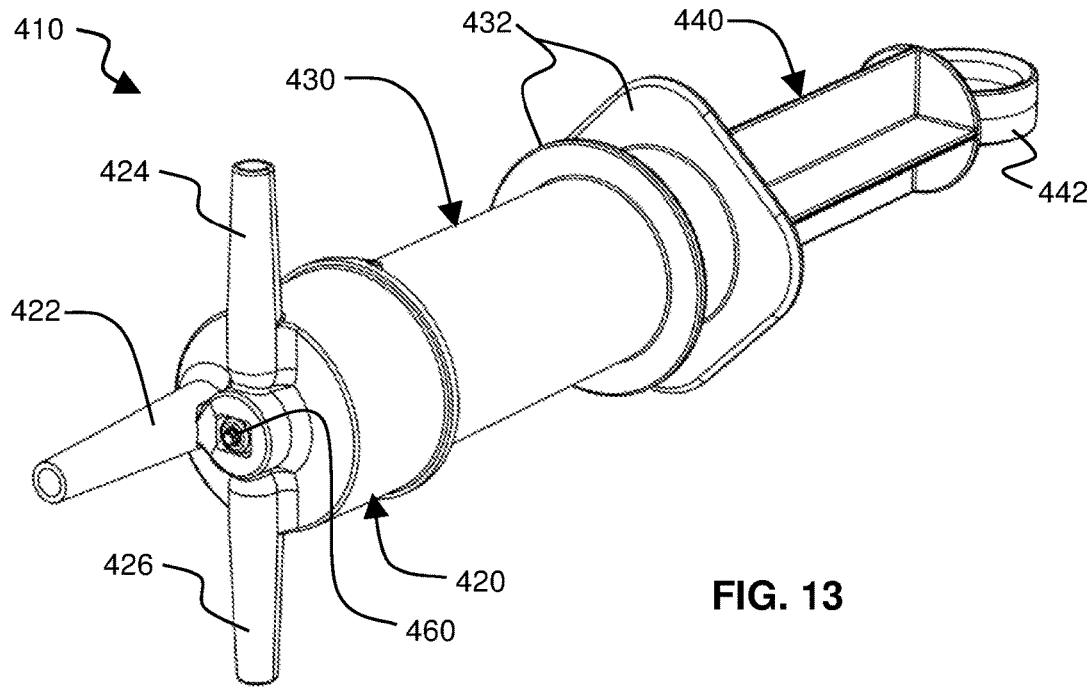
FIG. 13 is an isometric view of a three-axial-port syringe of FIG. 4 and FIG. 9.

FIG. 13 is an isometric view of the three-axial-port syringe that was also shown at 410 in FIG. 4 and FIG. 9. In FIG. 13, the syringe 410 has the plunger 440 extended out of the barrel 430 to maximize the volume of fluid in the barrel 430. The port body 420 comprises three ports: the input port 424; the catheter port 422; and the drainage port 426. Also shown is a port body fastener 460 which connects the port body 420 to the barrel 430 while allowing the barrel to rotate relative to the port body. Also shown in FIG. 13 is a barrel grasping feature (or features), shown at 432, and the plunger grasping feature 442, that can facilitate manual axial movement of the plunger 440 inside the barrel 430. In the embodiment shown, the barrel grasping feature 432 comprises two regions of the barrel that stick out from the outside of the barrel cylinder to provide a place configured for placement of one or more fingers. The plunger grasping feature 442 is a ring through which a user could place a finger. These features 432 and 442 could be any shapes capable of being understood by anyone skilled in the art.

Figure 14:
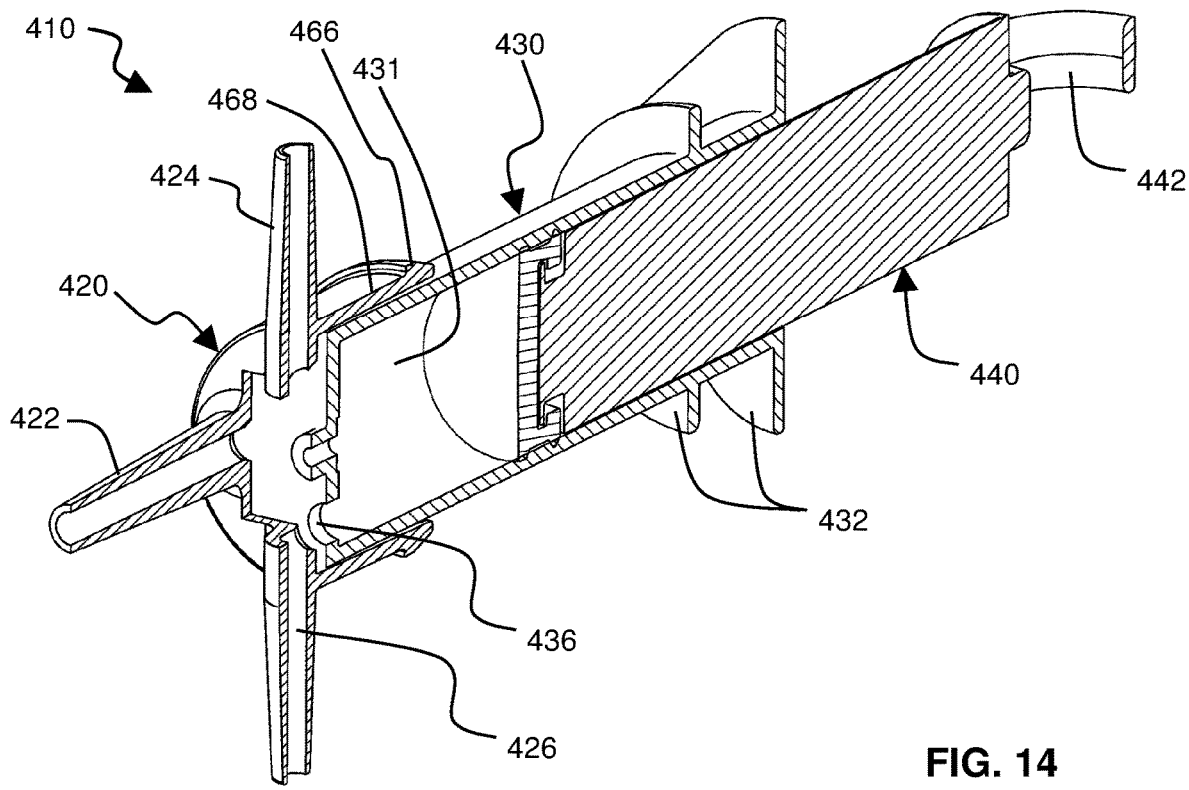
FIG. 14 shows a section view of the syringe of FIG. 13.

FIG. 14 shows a section view of the syringe of FIG. 13 to illustrate the syringe barrel interior volume 431 that expands and contracts as the syringe plunger 440 is moved axially in the syringe barrel 430. Worth noting are the barrel port 436 that is aligned with the drainage port 426, the barrel grasping features 432, and the plunger grasping feature 442. The port body 420, fill port 424, and catheter port 422 are also shown.

Figure 15:
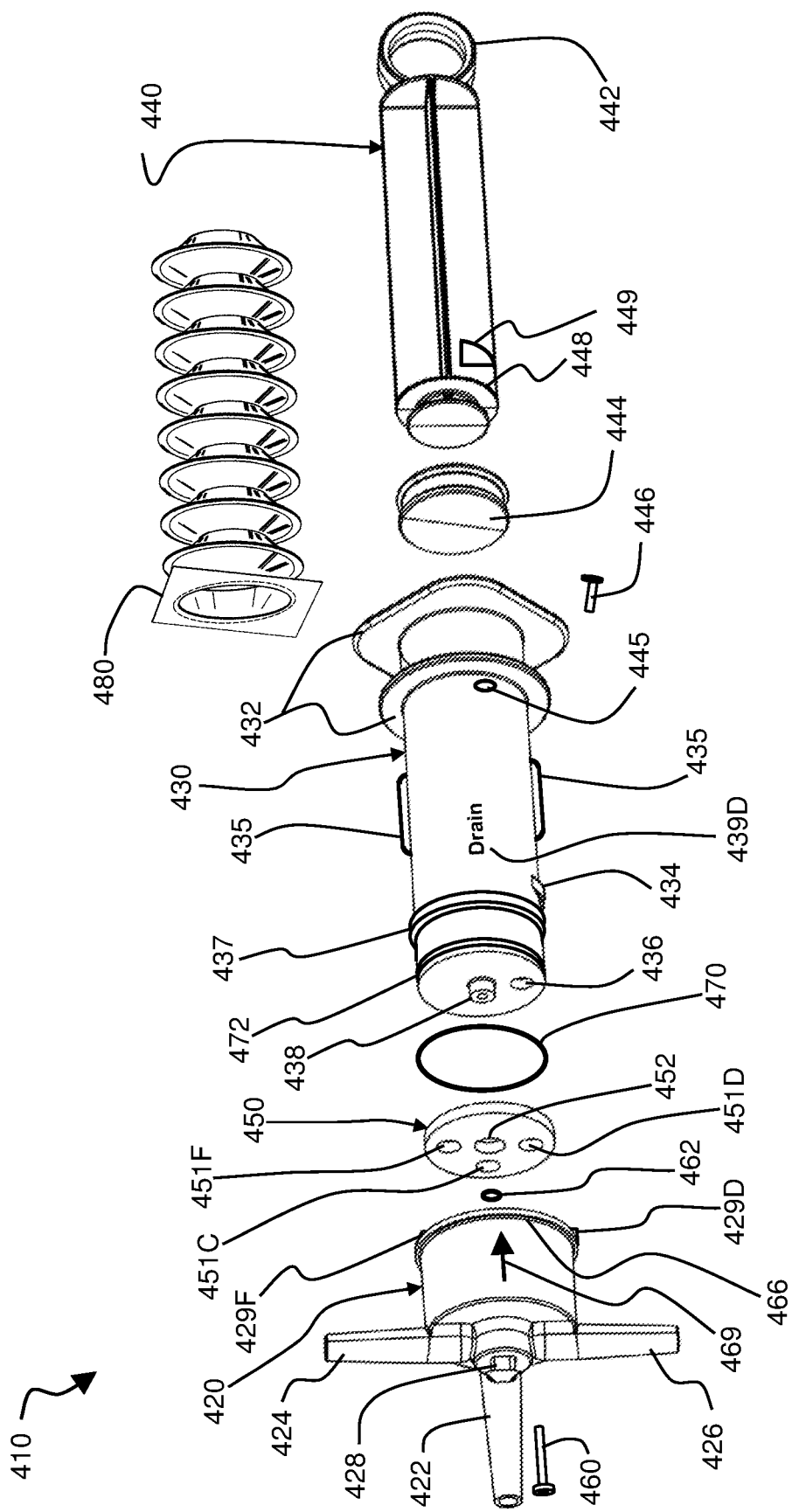
FIG. 15 is a detailed exploded view of the syringe of FIG. 13 and FIG. 14.

FIG. 15 is an exploded view of the three-axial-port syringe 410 that was shown in FIG. 4, FIG. 9, FIG. 13, and FIG. 14 and shows some further components and features as well. Some of the main components in this exploded view of the syringe 410 include:
(a) The port body 420 comprising the input port 424, catheter port 422, and drainage port 426;
(b) A gasket 450 that seals the port body 420 and barrel 430;
(c) A port body fastener 428 to secure the port body 420 to the barrel 430;
(d) The barrel 430, further comprising a barrel indexing feature 434, an axial barrel port (or aperture) 436, a cylindrical attachment boss 438, and the barrel grasping features 432;
(e) A plunger seal, shown at 444; and
(f) The plunger 440, which includes the plunger grasping feature 442.

The barrel 430 in FIG. 15 comprises a hollow cylinder with an open end and a closed end. The closed end of the barrel 430 is configured to fit inside the cup-shaped port body 420, with the gasket 450 sitting between the exterior of the closed end of the barrel and the circular bottom of the cup-shaped port body 420. The barrel port 436 is a circular axial aperture in the closed end of the cylindrical barrel 430 configured for transmission of fluid between the interior of the barrel and the ports (422, 424, and 426) in the port body that each have circular apertures in the circular bottom of the cup-shaped port body at one end of the ports (422, 424, and 426). The opposite ends of each of the three ports (422, 424, and 426) are configured for attachment to a catheter (for the catheter port 422), a fill line (for the fill port 424), and a drainage line (for the drainage port 426). Rotation of the barrel 430 relative to port body 420 allows for selective and exclusive transmission of fluid between the interior of the barrel 430 and one of the three ports the port body: the input (or fill) port 424; the catheter port 422; or the drainage port 426.

The gasket 450 in FIG. 15 is configured for rotational alignment with the port body 420 to seal the fluid connection between the ends of one of the three ports (422, 424, or 426) on the port body 420 and the barrel port 436. The gasket 450 would typically be made of a medical grade elastomer. In the configuration shown, the gasket 450 is a flat circular disk with three fluid flow apertures (451F, 451C, and 451D) surrounding a central mounting aperture 450. All four gasket apertures (451F, 451C, 451D, and 452) are circular. All four gasket apertures go through the gasket 450 in an axial direction (i.e. through the circular disk). The three fluid flow apertures (451F, 451C, and 451D) are equidistant from the central mounting aperture 452 and this distance is the same as the distance between the center of the barrel attachment boss 438 and the barrel port 436. In the configuration shown in FIG. 15, the three fluid flow apertures in the gasket (451F, 451C, and 451D) are spaced 90 degrees apart. When assembled, the three fluid flow apertures align with the respective circular apertures in the following configuration:

(a) The fill aperture 451F aligns with the barrel port 436 and the end of the fill port 424 for fluid transmission in an axial direction when the barrel is rotated into a first position;

(b) The catheter aperture 451C aligns with the barrel port 436 and the end of the catheter port 422 for fluid transmission in an axial direction when the barrel is rotated into a second position; and (c) The drainage aperture 451D aligns with the barrel port 436 and the end of the drainage port 426 for fluid transmission in an axial direction when the barrel is rotated into a third position.

When assembled, the barrel attachment boss 438 fits into the gasket central circular aperture 452. The port body fastener 460 attaches the port body 420 to the barrel 430 by going through a central aperture in the port body 428, through the gasket central circular aperture 452, and through the barrel attachment boss 438. A fastener O-ring 462 ensures that fluid cannot leak from the region surrounding the port body fastener 460. The barrel attachment boss 438 is a raised cylindrical section in the center of the circular closed end of the barrel 430 that facilitates the alignment of the barrel 430, port body 420, and gasket 450. The port body fastener 460 can be any mechanical fastener device, system or method capable of being understood by anyone skilled in the art. In FIG. 15 the port body fastener 460 has been shown as a machine screw. The port body fastener 460, port body 420, barrel 430, and gasket 450 are configured so that the port body 420 can be freely rotated about the axis of the barrel 430, but the port body 420 is prevented from moving axially relative to the barrel 430. The gasket 450 and port body 420 also comprise a rotational alignment feature configured to ensure that gasket 450 rotates with the port body 420 and not with the barrel 430, when the barrel 430 is rotated inside the port body 420.

Further referring to FIG. 15, the barrel indexing feature 434 is a raised area on the outside of the cylindrical barrel that is configured for assisting in the rotational alignment of the barrel port 436 with one of the three ports in the port body (422, 424, or 426) by aligning with port body indexing features (such as 429F and 429D) on the port body 420. The drainage indexing feature 429D is example of a such a feature that is visible in FIG. 15. When the drainage indexing feature (429D in FIG. 15) is aligned with the barrel indexing feature 434, the system is configured for exclusive transmission of fluid from the interior of the barrel to the drainage port 426. Similarly, when the catheter indexing feature (not visible) is aligned with the barrel indexing feature 434, the system is configured for exclusive transmission of fluid between the interior of the barrel and the catheter port 422. The same applies to the fill indexing feature (also not visible) and the fill or input fluid line.

The plunger 440 in FIG. 15 is configured for insertion into the open end of the hollow cylindrical barrel 430 and for axial travel inside the hollow cylindrical barrel 430 to increase and decrease the quantify of a fluid in a cylindrical barrel volume defined by the barrel hollow cylinder, the barrel closed end, and the sealed end of the plunger 444. The circular plunger seal 444 illustrated in FIG. 15 is an elastomeric cap on the end of the plunger 440. The plunger seal 444 is designed to help prevent fluid from escaping from the barrel 430 when the plunger 440 is pressed into the barrel 430 and to help prevent air from entering the barrel 430 when the plunger 440 is retracted from the barrel 430. The plunger grasping feature (or grip) 442 is designed to assist with manual grasping of the plunger and axial movement of the plunger inside of the barrel 430. This grip 442 is located on the end of the plunger that is opposite of the plunger seal 444.

FIG. 15 also illustrates that the barrel of the multi-port syringe can have an element, feature or features to restrict the travel (or axial movement) of the plunger in the barrel. This device, feature or features could be configured to prevent the plunger from exiting the barrel. This feature or features could be configured to lock the plunger in a partially extended position to allow for communication between the catheter and the drain ports for continuous gravity drainage. The plunger travel-limiting element, feature, or features could be mounted on the barrel, on the plunger, and/or on another component in the multi-port syringe. Plunger travel could be limited using a feature or features on more than one part of the syringe. In the embodiment shown in FIG. 15, plunger axial travel can be constrained by a plunger stop pin 446, that is designed to be inserted into a plunger stop pin hole 445 in the cylindrical wall of the barrel 430. When the plunger stop pin 446 is inserted into the plunger stop hole 445 and the plunger 440 is rotated so the plunger stop pin 446 is between a plunger end rib 448 and a plunger stop pin rib 449 on the plunger 440, axial travel of the plunger 440 in the barrel 430 is limited by the plunger end rib 448 and the plunger stop pin rib 449. Typically, the plunger stop pin 446 is permanently installed and locking the travel of the plunger 440 is accomplished by sliding the plunger past the stop pin in the slot next to the plunger stop in rib 449.

FIG. 15 also shows a barrel axial alignment feature 437. The barrel axial alignment feature 437 is a circular ring around the barrel hollow cylinder that provides for a tight fit between the port body 420 and the barrel 430 in a region close to the lip of the cup-shaped port body 420. The barrel axial alignment feature 437 improves the axial alignment of the barrel 430 in the port body 420. The barrel axial alignment feature 437 is near the port body rim (or lip) when the medical syringe system is assembled.

Another point of engagement between the port body and the barrel is a barrel O-ring seal 470 shown in FIG. 15. The barrel O-ring seal 470 is located between the cylindrical wall of the port body cup and the outside of the cylindrical body of the barrel 430 in a region close to the closed end of the barrel 430. In the embodiment shown in FIG. 15, the O-ring seal fits into a barrel O-ring groove 472 that is a circular groove in the cylindrical body of the barrel 430. The barrel O-ring seal 470 also improves the axial alignment of the barrel 430 in the port body 420. The barrel O-ring seal 470 is one of the seals that prevents the escape (or leakage) of fluids from the interior of the hollow cylindrical barrel 430 (i.e. preventing the leakage of fluid between the cup-shaped region of the port body 420 and the barrel 430).

Also shown in FIG. 15 is port body rotational position indicator 469. In the embodiment shown, the port body rotational position indicator 469 is an arrow located on the cylindrical wall of the cup-shaped port body 420, 90 degrees from the position of the fill port and opposite of the catheter port 422. This location for the port body rotational position indicator 469 was chosen so this indicator is on top of the port body 420 when the central axis of the syringe is horizontal and the syringe catheter port is down, the most natural ergonomic position for operating the multi-port syringe. The arrow on the port body rotational position indicator 469 points to a barrel rotational position indicator at 439D in FIG. 15. In the view of the embodiment shown in FIG. 15, the barrel rotational position indicator is the word "Drain" that is located on the cylindrical body of the barrel 430.

Embodiments of the syringe (410 in FIG. 4, FIG. 9, FIG. 13, FIG. 14, and FIG. 15 or 910 in FIG. 10 and FIG. 12) can be configured for attachment to a patient for an extended period of time when repeated intermittent manual irrigation as shown in FIG. 8 is needed over a prolonged hospitalization. In one embodiment, the syringe 410, could have one, or more, barrel attachment features, shown at 435 in FIG. 15. The barrel attachment feature(s) 435 could be located on the outside of the cylindrical barrel 430. The barrel attachment feature(s) 435 could be configured as loops with a slotted opening that accept a strap. The barrel attachment feature(s) 435 could be parallel bars on each side of the barrel 430 located 180 degrees of each other and would sit at 90 degrees from the front of the barrel when it is in the continuous gravity drain phase as noted by FIG. 27 and FIG. 28. The barrel attachment feature(s) 435 could be made of the same or similar material to the barrel 430. The barrel attachment feature(s) 435 could extend a few millimeters from the body of the barrel. The barrel attachment features(s) 435 could be a few centimeters in length and located between open end of the barrel and the rim of the port body. Therefore, once manual irrigation is no longer needed the multi-port syringe could be placed into continuous gravity drainage mode and then strapping the syringe to the patient by threading a strap through the barrel attachments feature(s) 435 taking the forward-facing strap extension and placing this strap through one barrel attachment feature 435, then around the body of the barrel 430 and then through the opposite positioned strap before being attached again to the leg strap that is wrapped around the patient's leg. The syringe could also be stabilized with only one barrel attachment feature 435 being strapped as well.

The barrel 430 could have a seal or cover at the open end of the barrel that attaches or wraps circumferentially around the plunger shaft. This prevents the introduction of outside contaminants into the system and reduces the risk of bodily fluids getting on the patient or user. In FIG. 15, a plunger cover 480 that comprises a bellows is shown as one example of such a seal or cover. One end of this plunger cover 480 could be attached to the barrel grasping feature 432. The other end of the plunger cover 480 could be attached to the plunger grasping feature 442. The plunger cover 480 could also be a flexible member, such as a balloon, that wraps around the entire exposed end of the plunger 440, including the grip 442.

Referring to FIG. 14 and FIG. 15, it can be seen that the port body 420 comprises a cylindrical cup, which consists of a circular bottom, a rim (or lip) 466, and a cylindrical wall 468 separating the circular bottom from the rim 466. Located on the rim 466 are a minimum of three port body rotational indexing features: one for the input or fill port 429F, one for the catheter port 429C, and one for the drainage port 429D. In the embodiment shown in FIG. 14 and FIG. 15, the port body indexing features (429F, 429D, and one not visible for the catheter port) protrude axially from the rim on a side of the rim opposite of the port body cylindrical wall 468. There are four circular axial apertures in the port body circular bottom: one for the input or fill port 424, one for the catheter port 422, one for the drainage port 426, and an aperture in the center of center port body circular bottom 428. The apertures for the fill, catheter, and drainage ports are designed to align with the barrel port 436 when the barrel is rotated to align with one of the port body rotational indexing features (429F, 429D, and indexing feature for catheter port) for exclusive fluid transmission between the interior of the barrel 430 and one of the ports (422, 424, or 426). The central port body circular bottom aperture 428 can be used for alignment with the barrel 430 when the syringe is assembled. The central port body circular bottom aperture 428 can also be used by a port body fastener 460 that connects the port body to the barrel 430.

5. Detachable Valving System for Standard Screw-On Syringe

Figure 16:
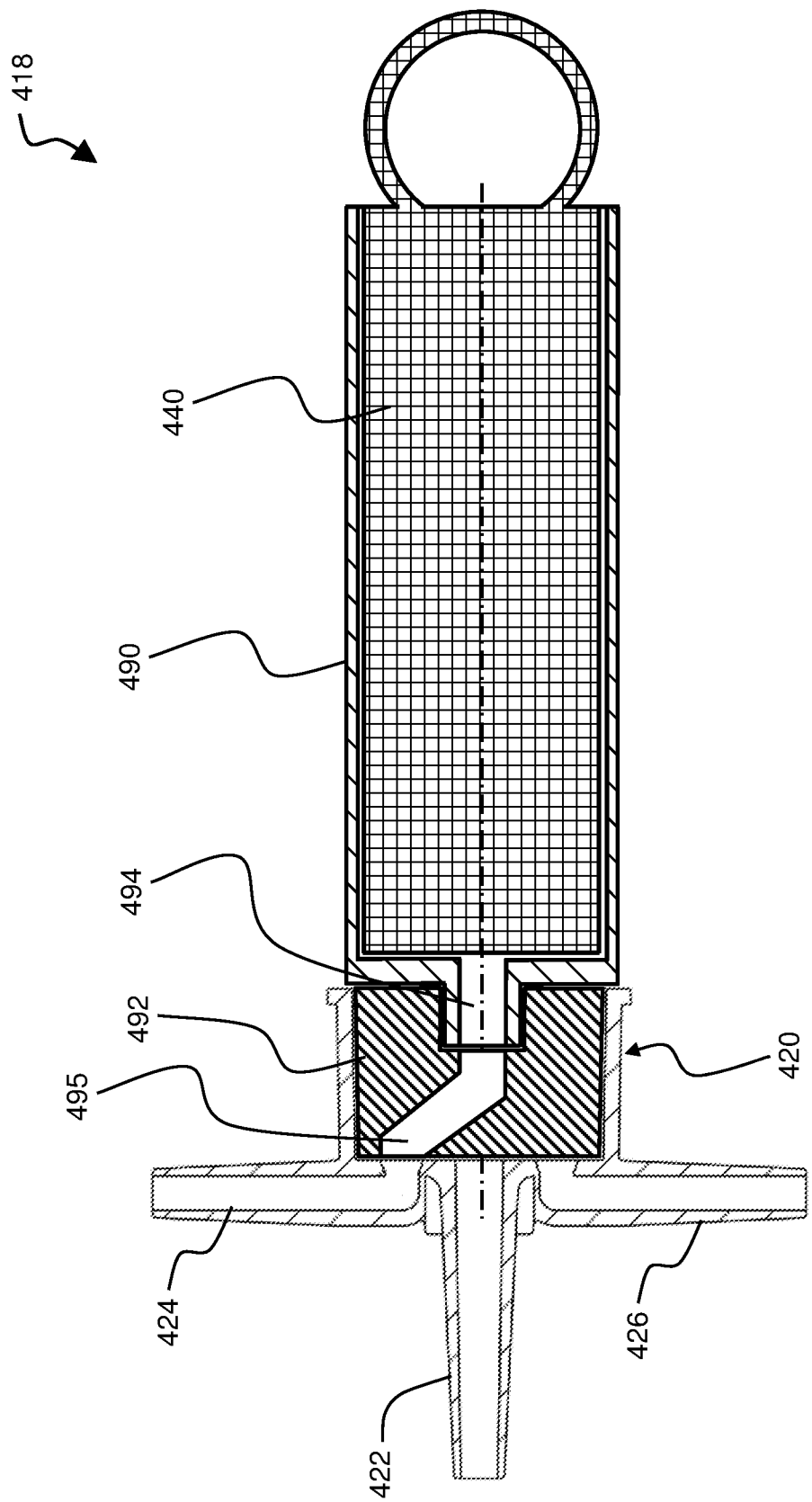
FIG. 16 is a section view of a three-axial-port syringe with a syringe barrel adapter.

FIG. 16 shows a section view of an alternate embodiment of a three-axial-port three-position syringe at 418. This is a side view that is similar to the cutaway that was shown in FIG. 14, but this alternate embodiment uses a central port syringe barrel 490 and a syringe barrel adapter 492 as a replacement for the syringe barrel 430 that was shown in FIG. 14. A central port syringe barrel 490 is a syringe barrel that has only one port and this port is located centrally. The syringe barrel adapter 492 can be designed to attach to the central port syringe barrel 490 using whatever tip adapter comes with the standard syringe barrel. For example, if the standard syringe barrel 490 has a luer lock tip, the syringe barrel adapter 492 could attach using a luer lock. The syringe barrel adapter 492 is configured to rotate with the standard syringe barrel 490 and adapt the central syringe port 494 of the central tip syringe barrel 490 to an eccentric axial syringe port 495 that can therefore selectively transmit fluid through the fill 424, catheter 422, or drain 426 ports of the port body 420 when the syringe port adapter 492 (which can be rotationally coupled to the standard syringe barrel 490) is rotated relative to the port body 420. In the embodiment shown in FIG. 16, the plunger 440 can be the same as what has been shown previously. It should be noted that it would also be possible to make configurations of the syringe barrel adapter 492 that would adapt to the ports of a syringe system that uses radial ports, such as that shown at 612 in FIG. 6A and FIG. 6B and/or a system that uses ports located on a cylindrical boss that goes into a cylindrical receptacle of a port body, such as that shown in FIG. 7A, FIG. 7B, and FIG. 7C.

6. Syringe with Three Radial Ports on a Cylindrical Boss of a Syringe Barrel FIG. 17A, FIG. 17B, FIG. 17C, and FIG. 18 provide multiple views of a three-radial-port on a cylindrical boss syringe 710 that is based on the configuration illustrated in FIG. 7A, FIG. 7B, and FIG. 7C. Referring to these illustrations in greater detail, the cylindrical boss port body is shown at 720, the cylindrical boss syringe barrel is shown at 730, and the plunger is shown at 440. The plunger 440 can be the same as what was shown and described with reference to FIG. 4 to FIG. 7C. FIG. 9-10, FIG. 12, FIG. and FIG. 14-16. The cylindrical boss port body 720 and cylindrical boss barrel 730 are basically the same as what was shown and described with reference to FIG. 7A to FIG. 7C. The entire three-radial-port on a cylindrical boss syringe 710 is a more complete syringe system than the alternate simple three-radial-port syringe shown at 712 in FIG. 7A to FIG. 7C. All of the functions and attributes shown and described for the syringe shown at 712 in FIG. 7A to FIG. 7C. can also be applied to the syringe shown at 710. The multi-port cylindrical boss syringe 710 can be substituted for the syringe shown at 410 in the systems illustrated in FIG. 4 and FIG. 9 and the method described in FIG. 8. Key elements of the three-port syringe shown at 710 can also be incorporated into the three-port continuous drainage syringe shown at 910 in FIG. 10 and FIG. 12 and the method described in FIG. 11.

Referring in greater detail to the cylindrical boss port body 720, this port body comprises a cylindrical boss 722, which comprises a first port 724, second port 726, and third port 728. Comparing these three cylindrical boss port body ports (724, 726, and 728) to the more simplified illustrations shown in FIG. 7A to FIG. 7C, it can be seen that these ports comprise radial inlets from the interior of the port body 720. The first port 724, which can be configured as the input port (or fill port), and third port 728, which can be configured as the drainage port (or drain port) have outlets that are also radial. The second port 726, which can be configured as a catheter port has an outlet that is axial. In this case, a radial direction is defined as a direction that is perpendicular to the axis of rotation of the barrel, as was shown at 569 in FIG. 7C and an axial direction is defined as a direction that is parallel to the axis of the rotation of the barrel. It is noteworthy that the outlets of these three comparable ports (424, 422, and 426 respectively) in FIG. 13 to FIG. 15 are also radial for the input port and drainage port and axial for the catheter port. The inlets for these three comparable ports (424, 422, and 426 respectively) in FIG. 13 to FIG. 15 are axial. Note that the views shown in FIG. 17A, FIG. 17B, and FIG. 17C show orientations of this multiport syringe 710 that are different from how it would typically be held. The orientation of this multi-port syringe 710 in FIG. 17A in normal use would be that the input port 724 would be at 9 o'clock, the catheter port 726 would be at 12 o'clock and the drainage port 728 would be at 3 o'clock. Thus, FIG. 17B would be rotated 90 degrees clockwise from how it is shown and FIG. 17C is a section view looking up from the bottom of this multi-port syringe 710. The views in FIG. 17A, FIG. 17B, and FIG. 17C were chosen to make it as easy as possible to see as many parts of this syringe system 710.

Figure 18:
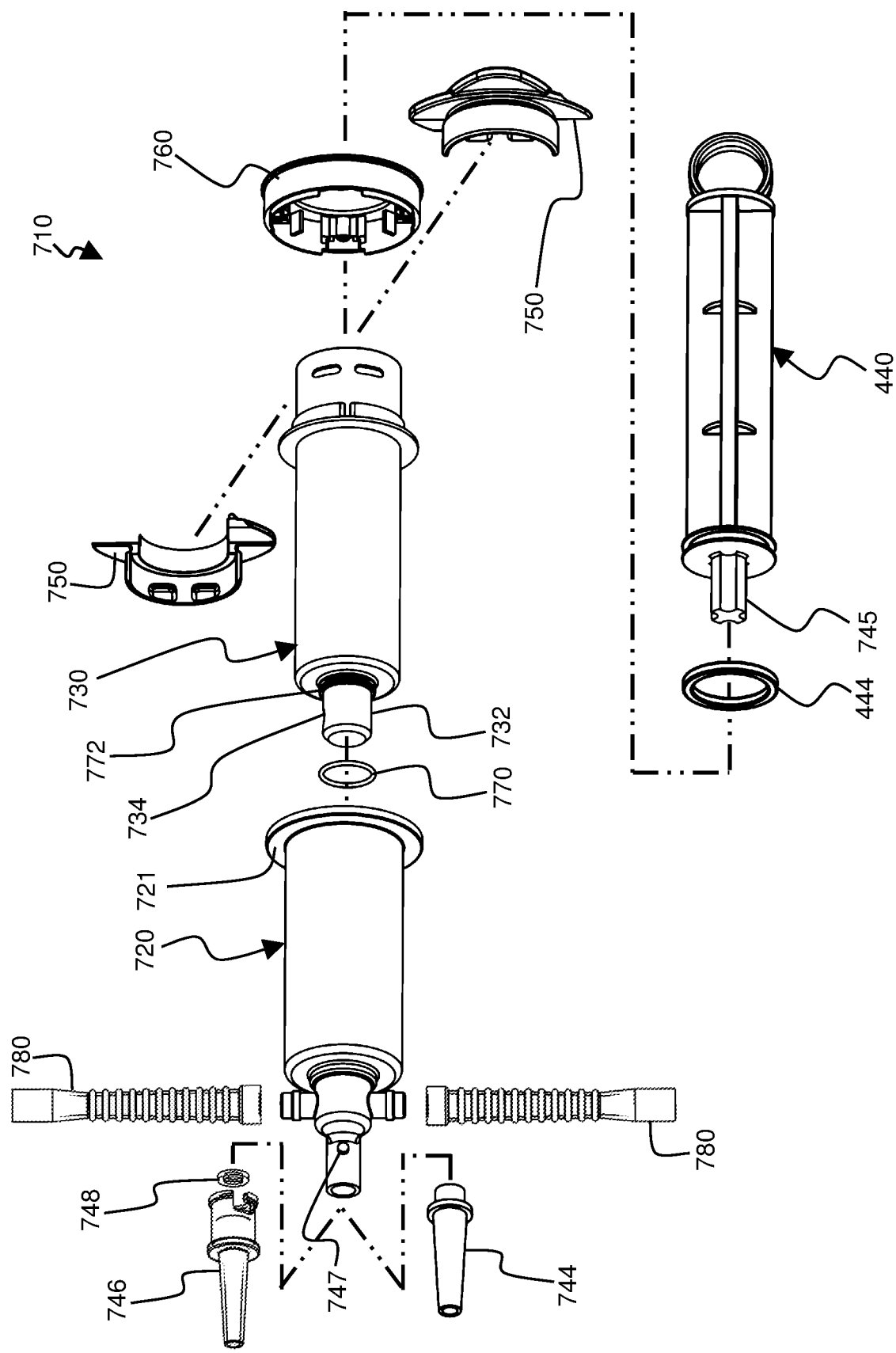
FIG. 18 shows an exploded view of the syringe of FIG. 17A that further comprises a detachable tip, and flexible port adapters for the fill and drain ports.

Referring in greater detail to the cylindrical boss syringe barrel 730, that can best be seen in FIG. 17C and FIG. 18 and was also shown and described in FIG. 7C, this syringe barrel 730 comprises a neck 732 which further comprises a radial port 734. The cylindrical boss or neck 732 and radial port 734 have all of the features and attributes that were described with reference to FIG. 7C.

FIG. 17A, FIG. 17B and FIG. 17C show a single circumferential port barb 740 on the input port 724 and drainage port 728. FIG. 20 shows the cylindrical boss port body 720 of FIG. 17A to FIG. 18 with multiple part-circular port barbs 742. Either of these types of port barbs can be used in embodiments of the invention, or the ports could have tapered tips, as shown at 422, 424, and 426 in FIG. 4, FIG. 9, FIG. 10, and FIG. 12 to FIG. 16. The ports could also have straight tips, with no barbs of any kind. The tips can be used for the attachment of fluid lines, such as the port adapters shown at 780 in FIG. 18. The ports could also have tip that is added, such as the permanent catheter tip shown at 744 in FIG. 18 or the detachable catheter tip shown at 746 in FIG. 18 and FIG. 19. A permanent tip, such as the permanent catheter tip 744, could be permanently attached to a port of the port body using any techniques capable of being understood by those skilled in the art, such as gluing, ultrasonic welding, spin welding, or a very tight press fit. A detachable tip, such as the detachable catheter tip 746 could be attached to a port of the port body using port bosses, such as the cylindrical port bosses shown at 747 in FIG. 17C, FIG. 18, FIG. 19, and FIG. 20. From these illustrations, it can be seen that this port has two cylindrical port bosses located opposite of one another on the exterior of the cylindrical catheter port. The detachable tip 746 could be sealed using a detachable tip gasket, shown at 748 in FIG. 18. The detachable tip 746 and detachable tip gasket 748 could be attached over a port in the port body 720 using a slot in the detachable tip that slips over the port bosses 747 and then the detachable tip 746 is twisted so the detachable tip 747 is retained by the port bosses 747. One advantage of using a detachable tip 746 for the for the catheter tip is that it facilitates substitution of a cystoscope for the catheter when a cystoscope is used for a bladder procedure.

Figure 19:
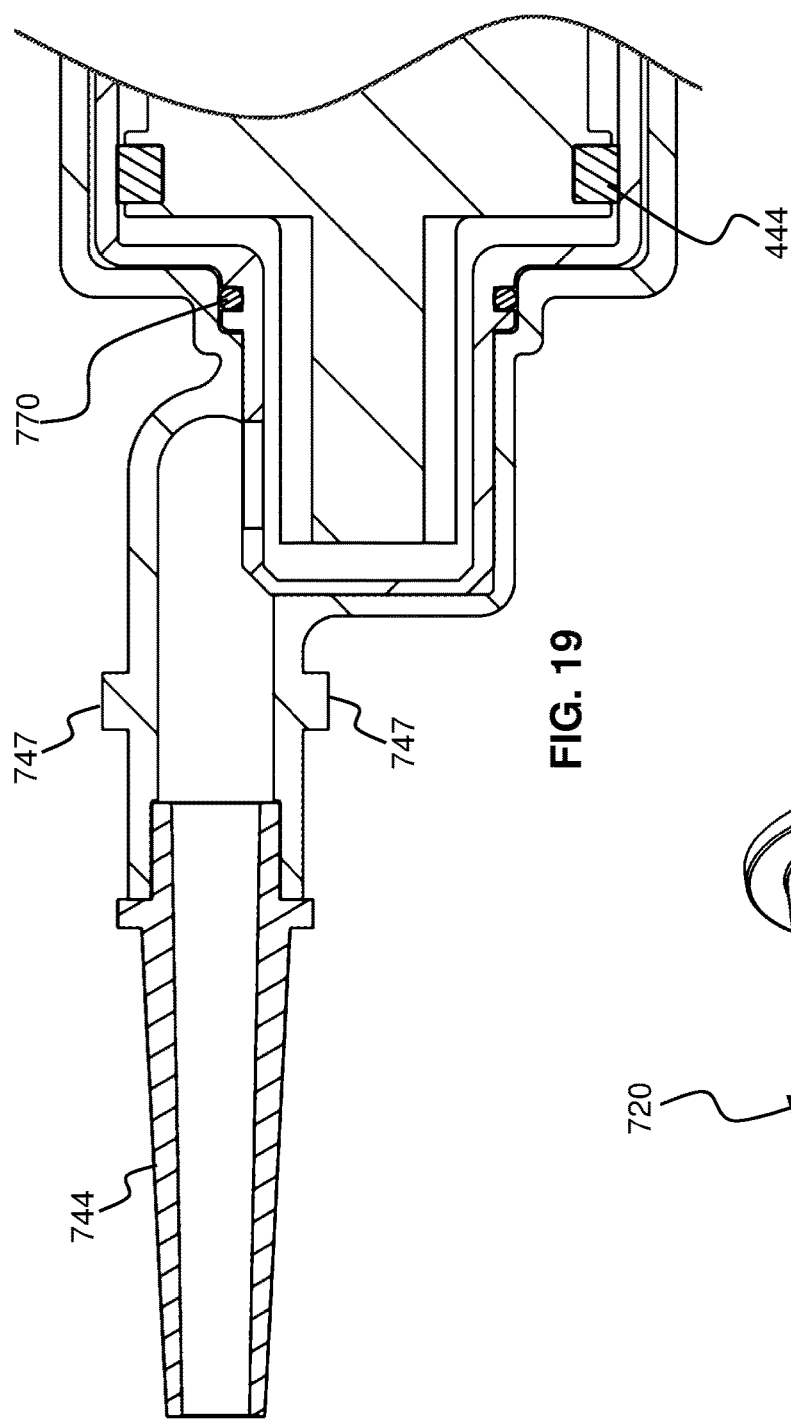
FIG. 19 is a detail of section C-C of FIG. 17A.
Figure 20:
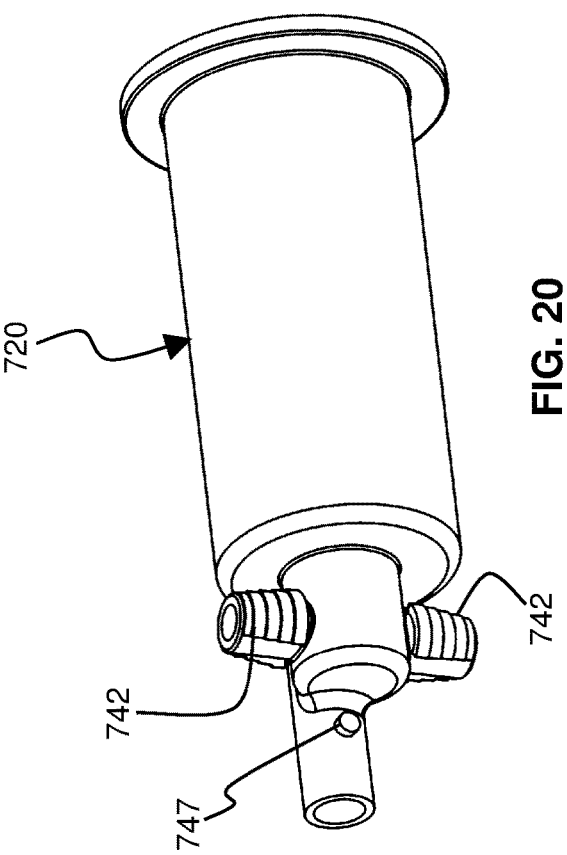
FIG. 20 shows an alternate port body with barbs on the fill and drain ports.

Referring to FIG. 17C, FIG. 18, and FIG. 19, there can be an O-ring 770 that is located on an O-ring groove 772 on the cylindrical boss 732 of the syringe barrel 730. This O-ring seals the cylindrical receptacle of the port body from the outside environment to prevent leakage of fluid to the outside environment. The plunger seal 444 can be an X-ring that fits into a groove of the plunger 440.

FIG. 17B, FIG. 17C and FIG. 18 show a two-piece plunger stop at 750. This plunger stop 750 is further detailed in FIG. 21A and FIG. 21B. Referring to the section details shown in FIG. 21A and FIG. 21B, the plunger stop system comprises two plunger stop halves 750 that are identical and interlock around the outside of the cylindrical syringe barrel 730. The syringe barrel 730 has at least one plunger stop aperture 752. In the embodiment shown, there are four plunger stop apertures 752 in the syringe barrel 730. The location and shapes of these plunger stop apertures 752 can also be seen clearly in FIG. 22A and FIG. 22B. The plunger stop apertures 752 are proximate to the open end of the syringe barrel 730 Each plunger stop 750 has two plunger stop pins 754 that go through the plunger stop apertures 752 into the open cylindrical center section of the syringe barrel 730 to prevent the plunger 440 from being accidentally removed from the syringe barrel 730. The plunger stop pins 754 also engage with ribs on the plunger shaft 443 to couple the rotation of the plunger 440 with the rotation of the syringe barrel 730.

Figure 22A:
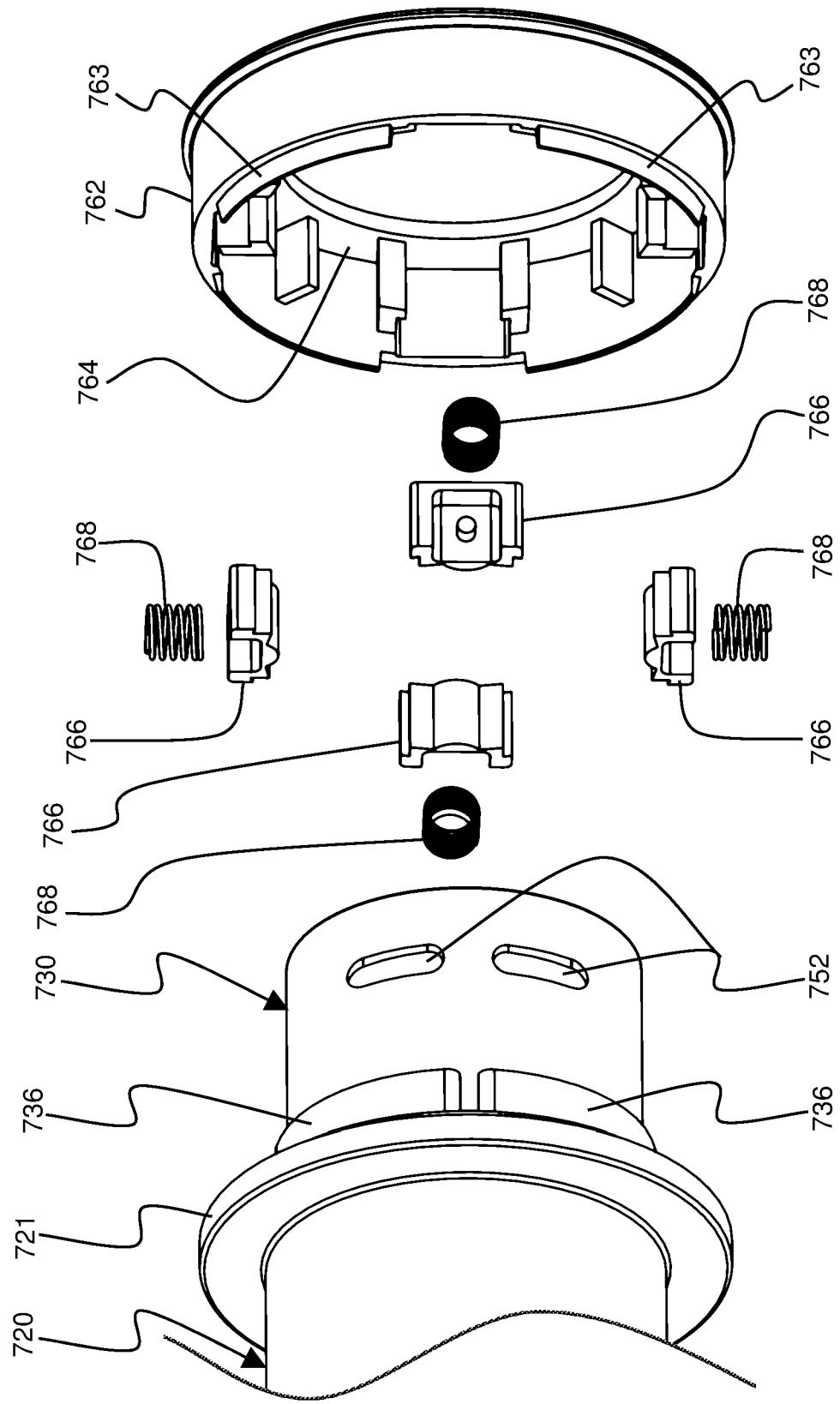
FIG. 22A and FIG. 22B are detailed exploded views of the retainer, port body, and syringe barrel that were shown in FIG. 18.
Figure 22B:
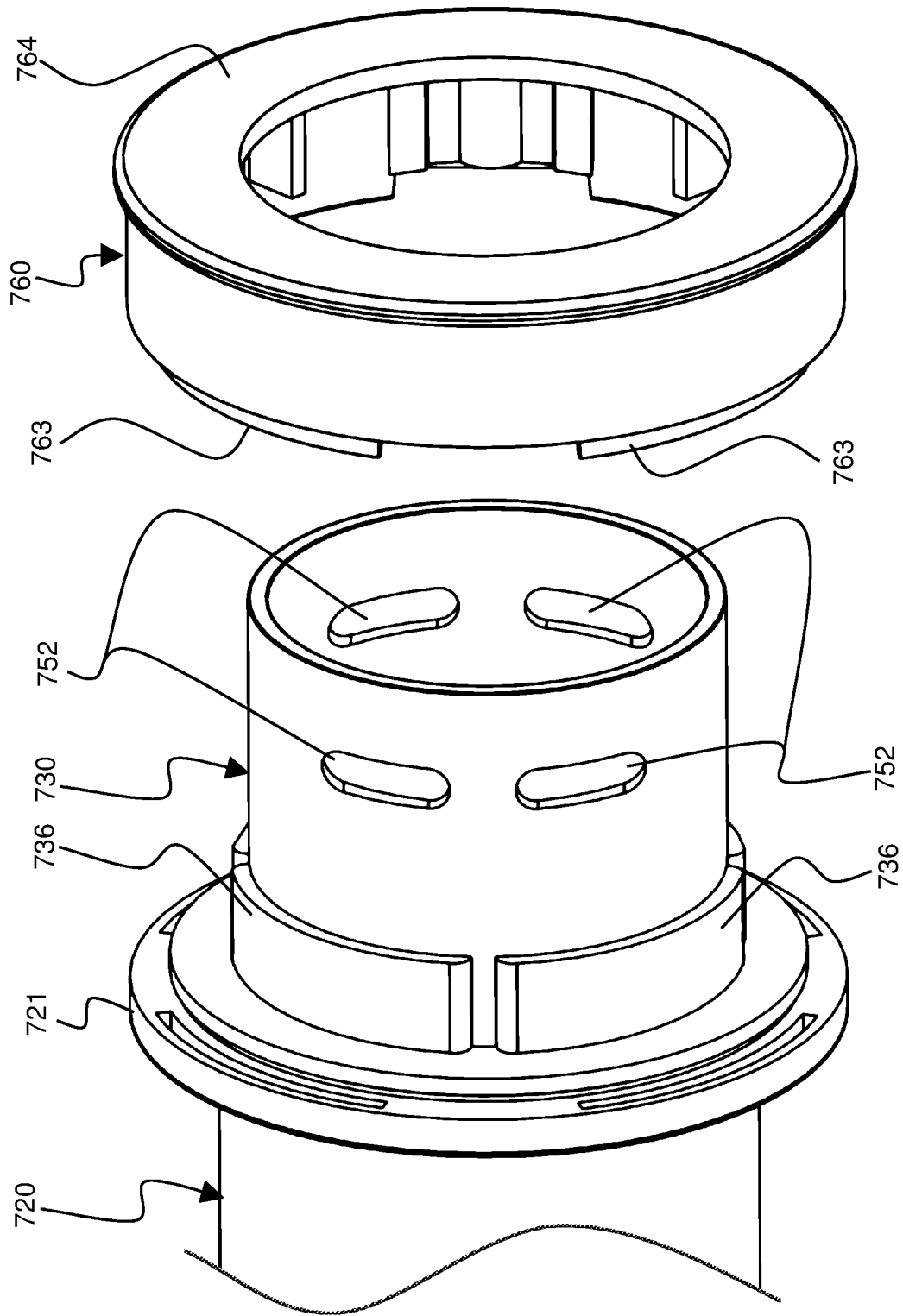

FIG. 17B, FIG. 17C and FIG. 18 show a barrel retainer assembly at 760. This barrel retainer assembly 760 is further detailed in FIG. 22A and FIG. 22B. Referring to these illustrations, the port body 720 comprises a protrusion in the form of a circumferential ring, shown at 721 and located at the open end of the port body cylindrical cavity. The syringe barrel 730 also comprises a protrusion in the form of one or more syringe barrel indexing ring segments, shown at 736, located proximate to the open end of the syringe barrel 730. In the embodiment shown, the barrel retainer assembly 760 comprises a barrel retainer ring 762 that comprises one or more barrel retainer ring tongues 763 that engage with grooves in the port body circumferential ring 721 to secure the barrel retainer ring assembly 760 to the port body circumferential ring 721. In one embodiment the barrel retainer ring tongues 763 are glued in the grooves of the port body circumferential ring 721. The attachment of the barrel retainer assembly 760 to the port body can be done using any attachment method known in the art such as mechanical fasteners, snap fits, or ultrasonic bonding. When assembled, the syringe barrel indexing ring segments 736 are captured inside the barrel retainer assembly 760 between an end wall 764 of the barrel retainer ring and the port body circumferential ring 721. As shown in FIG. 22A, the barrel retainer assembly 760 also comprises retainer assembly indexing blocks 766 and retainer assembly indexing block springs 768 that ride on the syringe barrel indexing ring segments to click into place when the syringe barrel 730 has been rotated to a indexed position in the port body 720 that corresponds to the off, fill, irrigate, or drain port positions shown in FIG. 8.

Figure 23E:
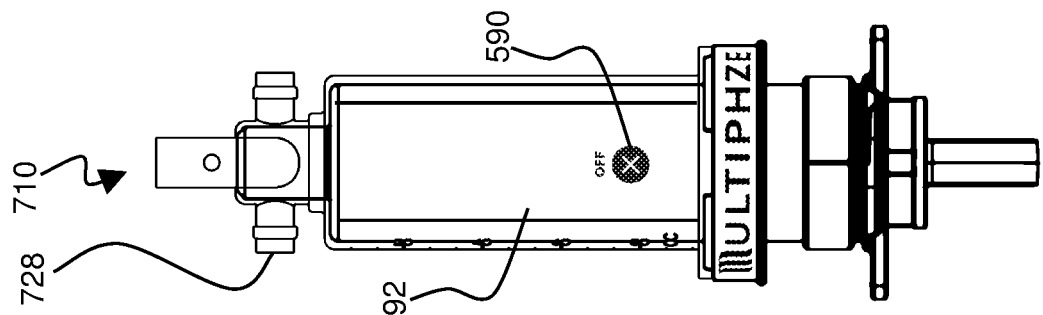
FIG. 23A to FIG. 23E show views of the labeling of the syringe of FIG. 17B.
Figure 23D:
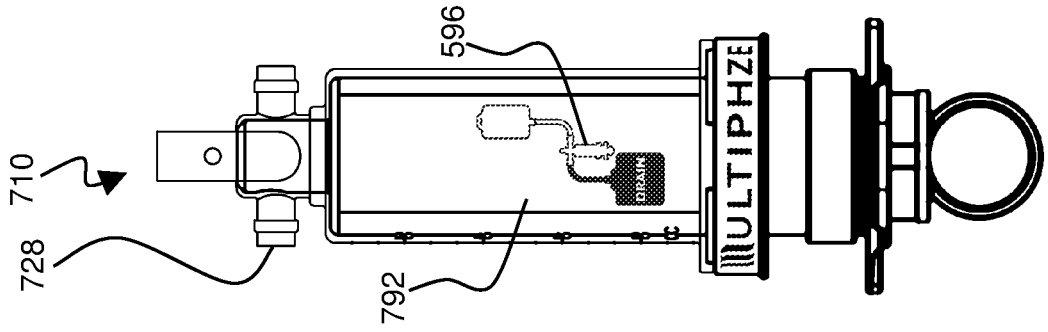
Figure 23C:
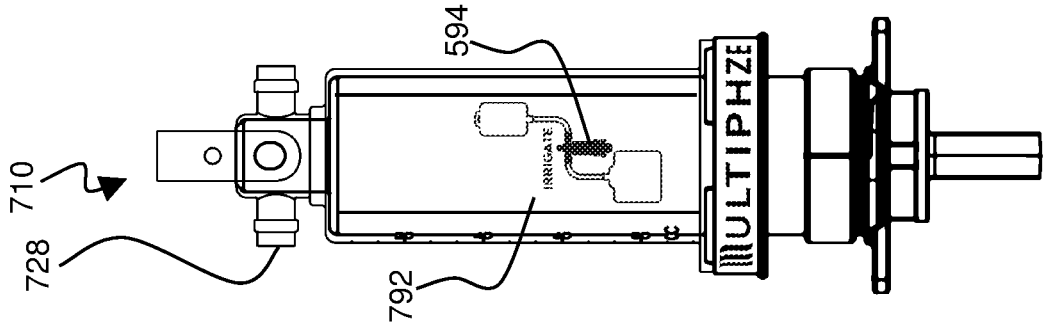
Figure 23B:
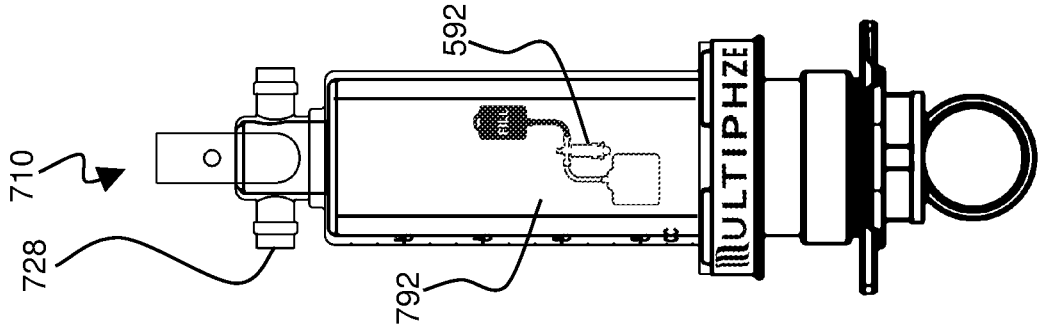

FIG. 23A to FIG. 23E show views of the labeling of the three-radial-port on a cylindrical box syringe 710 that was shown previously. FIG. 23B to FIG. 23E are views of the multiport syringe 710 in an orientation where the position of the syringe barrel is visible to the user. The difference between these views is that the syringe barrel and plunger have been rotated to various positions inside the port body. More specifically, the syringe barrel and plunger:

Have been rotated to the fill position in FIG. 23B;
Have been rotated to the irrigate position in FIG. 23C;
Have been rotated to the drain position in FIG. 23D; and
Have been rotated to the off position in FIG. 23E.

Figure 23A:
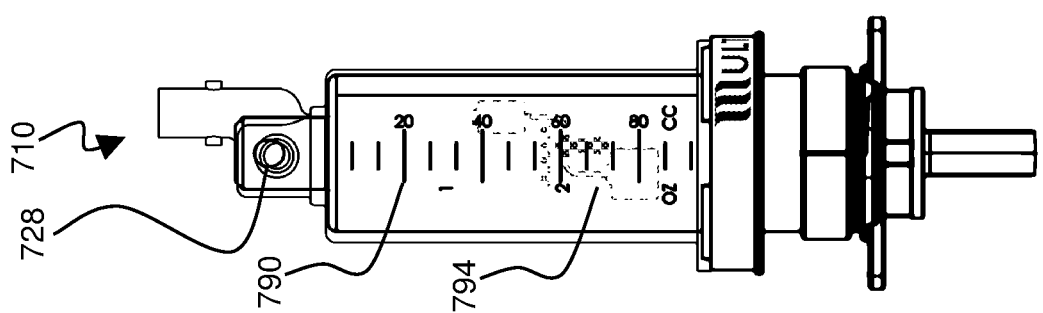

To help understand the orientation of the port body in these views, the drainage port 728 has been labeled in FIG. 23A to FIG. 23E. Thus, the entire assembly including the port body, syringe barrel, and plunger shown in FIG. 23A is shown rotated by 90 degrees from the FIG. 23B, so that the drainage port is facing the viewer, which illustrates a volumetric scale 790 on the port body in FIG. 23A that is barely visible on the left side of the port body in FIG. 23B to FIG. 23E. To ensure that the user knows the current rotational position of the syringe barrel in the port body, the port body can have:

The fill position indicator 592 visible when the syringe barrel and plunger have been rotated to the fill position (FIG. 23B);
The irrigate position indicator 594 visible when the syringe barrel and plunger have been rotated to the irrigate position (FIG. 23C);
The drain position indicator 596 visible when the syringe barrel and plunger have been rotated to the drain position (FIG. 23D); and
The off position indicator 590 visible when the syringe barrel and plunger have been rotated to the off position (FIG. 23E).

The location fill position, irrigate position, drain position, and off position indicators shown at 592, 594, 596 and 590 in FIG. 23B, FIG. 23C, FIG. 23C, and FIG. 23E can be made visible to the user by providing a clear window 792 in the port body, with the rest of the circumference of the port body being a non-clear region 794. The non-clear region could be translucent, opaque, or use any other technique for distinguishing it from the clear region (or clear window) 792.

Figure 24:
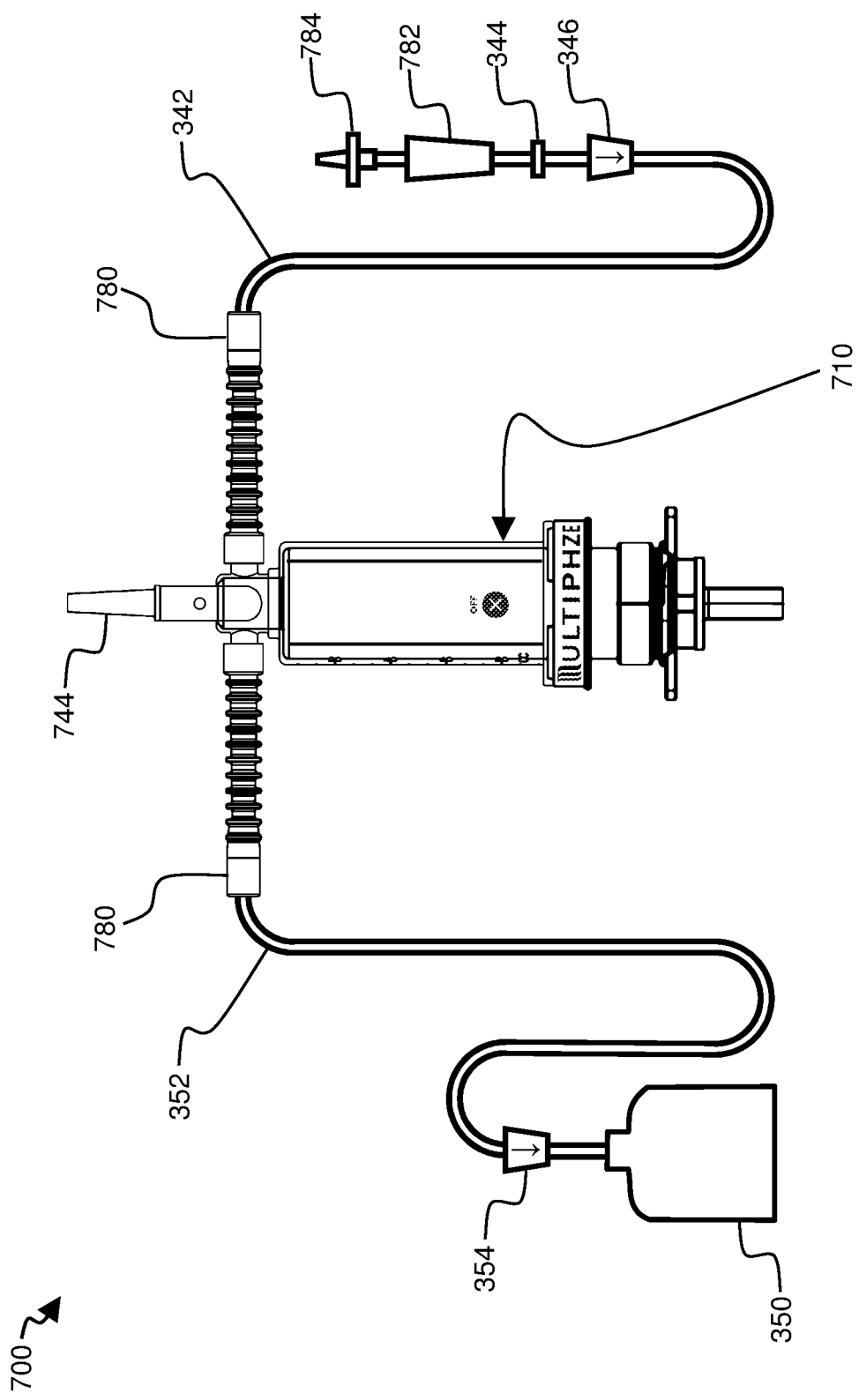
FIG. 24 shows a sterile kit incorporating the syringe of FIG. 17B.

FIG. 24 shows a sterile multi-port syringe kit 700 incorporating the three-radial-port on a cylindrical box syringe 710 of FIG. 17B, with the orientation of all system components to match the view shown in FIG. 23E. In addition to the syringe 710, the port adapters 780 (shown previously in FIG. 18), and the catheter tip 744 (shown previously in FIG. 18), this sterile syringe kit 700, also comprises the following components shown previously in FIG. 4: the input fluid line 342, the input check valve 346, the input line clamp valve 344, the drainage line 352, the drainage line check valve 354, and the drainage bag 350. In addition, the sterile multi-port syringe kit 700 can comprise a drip chamber assembly 782 and an input fluid bag connector 784. The input fluid bag connector 784 can be configured to connect to an input fluid source, of the type that was shown and described with reference to FIG. 4. The entire sterile multi-port syringe kit 700 can be packaged in a sterile pouch. Such a sterile kit 700 in a sterile pouch could be deployed in a manner that makes the entire bladder irrigation process much cleaner and easier than the prior art, and it can do this at a competitive cost. The sterile multi-port syringe kit 700 in a sterile pouch can be used as a single-use disposable assembly.

7. Alternative Syringe Port Configurations on the Syringe

Figure 25:
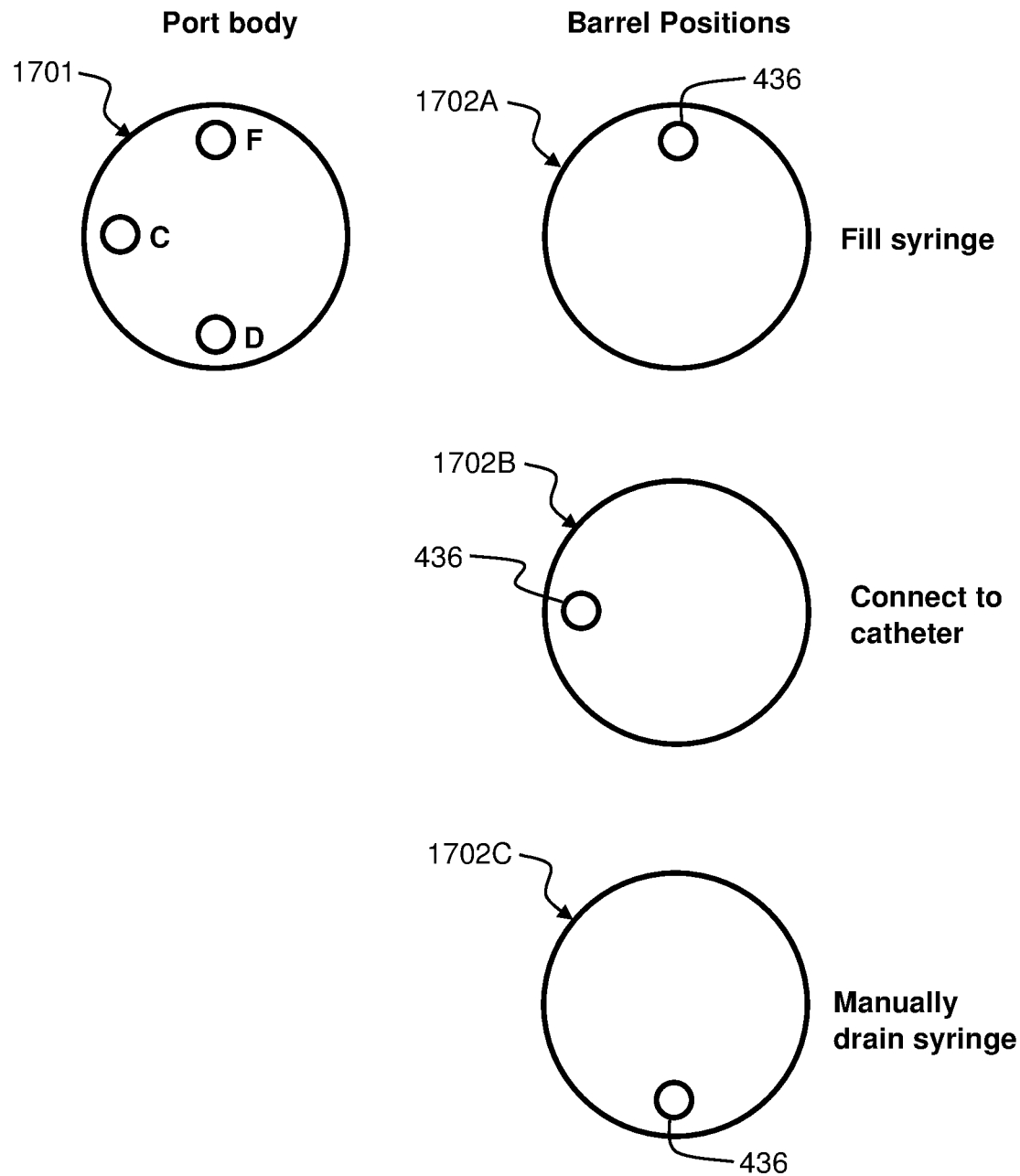
FIG. 25 shows how the rotation of the syringe barrel inside the port body of embodiments of the multi-port syringe allows the contents of the syringe barrel to be selectively connected to the fill, catheter, and drain ports of the port body.

FIG. 25 shows a schematic of how the rotation of the barrel inside the port body of a 3-position syringe can be used to allow the content of the barrel to be selectively connected to the fill (i.e. input or fill port or "F"), catheter (or "C"), and drainage (or "D") ports. The position of the port body is shown at 1701 and is assumed to be the same for all rotations of the barrel in the second column. The input or fill port "F" in FIG. 25 is a schematic representation of the location of the input or fill port shown at 424 in FIG. 4, at 552 in FIG. 5A to FIG. 5E, and at 424 in FIG. 9, and FIG. 13 to FIG. 16. The catheter port "C" in FIG. 25 is a schematic representation of the location of the catheter port shown at 422 in FIG. 4, at 554 in FIG. 5A to FIG. 5E, and at 422 in FIG. 9 and FIG. 13 to FIG. 16. The drainage port "D" in FIG. 25 is a schematic representation of the location of the drainage port shown at 426 in FIG. 4, at 556 in FIG. 5A to FIG. 5E, and at 426 in FIG. 9 and FIG. 13 to FIG. 16. Three rotational orientations of the barrel are shown at 1702A, 1702B, and 1702C in FIG. 25. In actual usage, the barrel would be located behind and aligned with the port body as was illustrated in FIG. 5A to FIG. 5E and FIG. 13 to FIG. 16. For clarity, the selectable positions of the barrel in FIG. 25 are shown in a column to the right of the port body so that the three selectable rotational positions can be understood more clearly. The barrel port shown at 436 in FIG. 25 is the same axial aperture in the end of the barrel that was shown in FIG. 5B to FIG. 5D, FIG. 5F, FIG. 14, and FIG. 15. From the schematic illustration in FIG. 25, one can see that:

(a) Having the opening in the barrel 1702A at the 12 o'clock position will allow fluid to flow between the barrel and the "F" (Fill) port. Thus, 1702A shows the barrel at a "Fill syringe" position.
(b) Having the opening of the barrel 1702B at the 9 o'clock position will allow fluid to flow between the barrel and the "C" (Catheter) port. Thus, 1702B shows the barrel at a "Connect to catheter" position.

(c) Having the opening of the barrel 1702C at the 6 o'clock position will allow fluid to flow between the barrel and the "D" (Drainage) port. Thus, 1702C shows the barrel at a "Manually drain syringe" position.

Although the embodiments illustrated in FIG. 4 to FIG. 5E, FIG. 9, and FIG. 13 to FIG. 16 show only a single axial barrel port 436 that interfaces with the port body to allow flow of a fluid an axial direction (i.e. the fluid flows parallel to the central axis of the cylindrical barrel), it should be understood that some or all of the ports in the port body could also interface with the syringe barrel in a radial configuration (i.e. flowing in a direction inwards or outwards from the central axis of the cylindrical barrel), such as the configurations shown in FIG. 6A to FIG. 7C and FIG. 17A to FIG. 20. There can also be differences in the amount of rotation of the syringe barrel relative to the port body that is needed to move from one selectable position (or phase) to another selectable position (or phase). The embodiments illustrated in FIG. 5A to FIG. 7C and FIG. 13A to FIG. 24 show a 90-degree (¼ circle) rotation for moving from one selectable port position to another. These rotations could be more or less than this and do not need to be an even fraction of a 360-degree circle.

Figure 26:
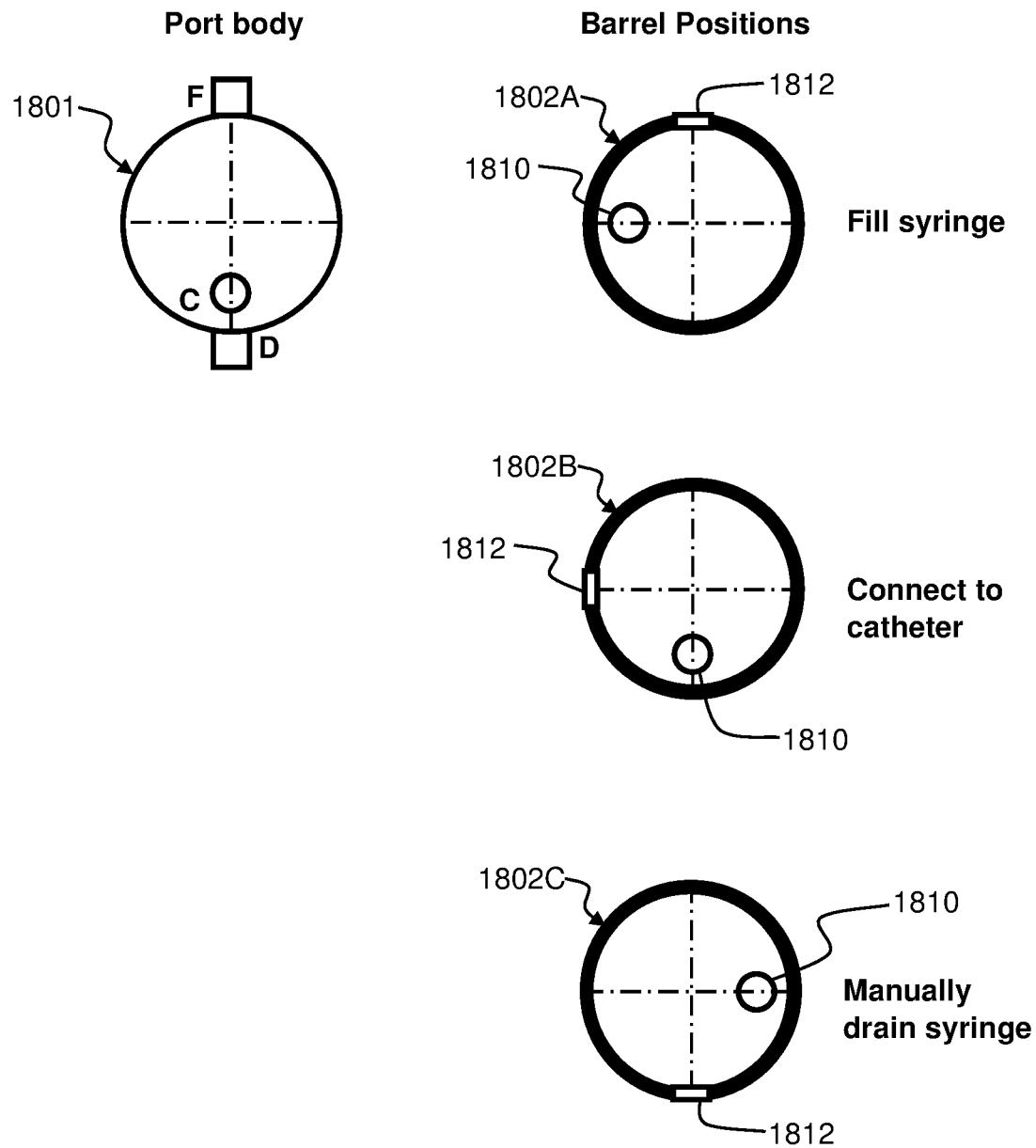
FIG. 26 shows an alternate port body and syringe barrel configuration for a 3-port 3-position syringe in which some ports are axial and some ports are radial.

FIG. 26 shows a schematic of an alternate embodiment of a port body 1801 and three positions of a barrel 1802A, 1802B, and 1802C for a 3-port syringe. The port body 1801 has one axial port that connects to the catheter and is labeled "C" and two radial ports: fill (i.e. input or fill port or "F"); and drainage (or "D"). The barrel has one axial aperture, shown at 1810 and one radial aperture, shown at 1812. The position of the port body 1801 is assumed to be the same for all rotations of the barrel, 1802A, 1802B, and 1802C in the second column. In actual usage, the barrel (1802A, 1802B, or 1802C) would be located behind and aligned with the port body. For clarity, the selectable positions of the barrel are shown in a column to the right of the port body so that the three selectable rotational positions can be understood more clearly. From this schematic illustration, one can see that:

(a) having the opening in the barrel 1802A at the 12 o'clock position will allow fluid to flow between the barrel and the "F" (Fill) port in a "Fill syringe" position;

(b) having the opening of the barrel 1802B at the 9 o'clock position will allow fluid to flow between the barrel and the "C" (Catheter) port in a "Connect to catheter" position; and (c) having the opening of the barrel 1802C at the 6 o'clock position will allow fluid to flow between the barrel and the "D" (Drainage) port in a "Manually drain syringe" position.

Figure 27:
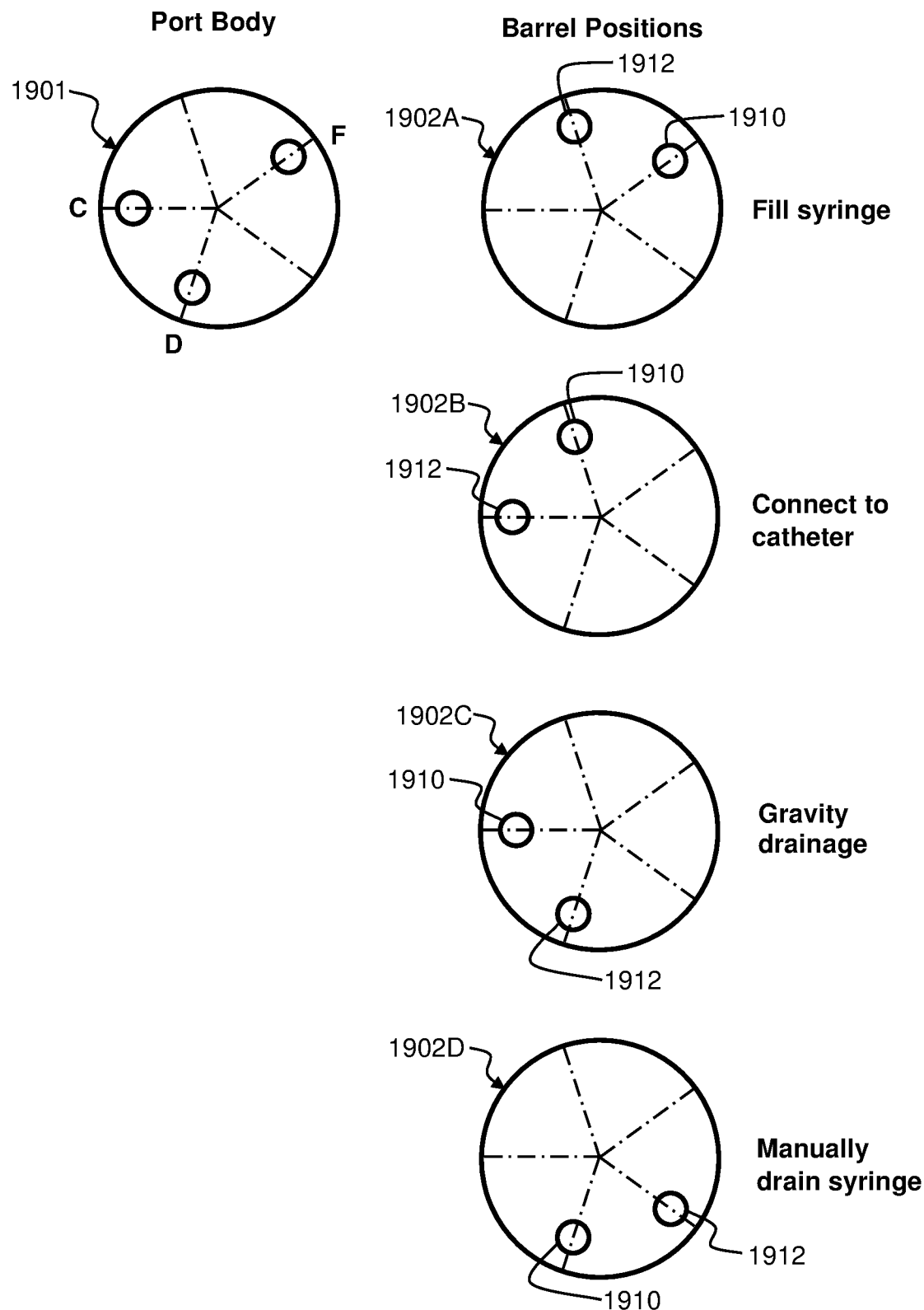
FIG. 27 shows a port body and syringe barrel configuration that provide selective connection to the fill, catheter, and drain ports, and for continuous bladder irrigation that can implement the system of FIG. 10 and FIG. 12.

FIG. 27 shows a schematic of another alternate configuration of a port body and barrel that has three ports (Fill or "F", Catheter or "C", and Drainage or "D") in the port body, shown at 1901. As was the case for the schematics shown in FIG. 25 and FIG. 26, the position of the port body 1901 is assumed to be the same for all rotations of the barrel in the second column. The barrel has a first axial aperture, shown at 1910 and a second axial aperture shown at 1912. Four rotational positions of the barrel are shown at 1902A, 1902B, 1902C, and 1902D. In actual usage, the barrel would be located behind and aligned with the port body as was illustrated in FIG. 5A to FIG. 5E and FIG. 13 to FIG. 16. For clarity, the selectable rotations of the barrel are shown in a column to the right of the port body so that the four possible selectable rotations can be understood more clearly. From this schematic illustration, one can see that only four of the five possible equally spaced (72-degree or $\frac{1}{5}^{th}$ of a 360-degree circle) rotations of the barrel are needed to provide the functions needed for a 4-phase (i.e. 4-position) syringe of the type illustrated at 910 and described with reference to FIG. 10, FIG. 11, and FIG. 12.

Further referring to FIG. 27, the sequence of the four needed selectable rotations, when the barrel is rotated counterclockwise, is:

Barrel in "Fill syringe" orientation 1902A with the first barrel axial aperture 1910 aligned with the "F" (input or fill port) of the port body;

Barrel in "Connect to catheter" orientation 1902B with the second barrel axial aperture 1912 aligned with the "C" (catheter) port of the port body;

Barrel in "Gravity drainage" orientation 1902C, when the Catheter ("C") port is aligned to the first barrel axial aperture 1910 and the Drainage ("D") port is aligned with the second barrel axial aperture 1912; and Barrel in "Manually drain syringe" orientation 1902D when the Drainage ("D") port is aligned with the first barrel axial aperture 1910.

The rotation sequence illustrated in FIG. 27 may not be as ideal as a sequence in the following order: "Fill syringe"; "Connect to catheter"; "Manual drainage"; and "Gravity drainage" because an operator would be using "Fill", "Connect", and "Manual Drainage" while doing manual irrigation and would not want to pass through an unused position as part of the process of going between these three positions. However, the configuration illustrated in FIG. 27 can be implemented using axial ports only. The construction of a syringe system with the functionality illustrated in FIG. 27, FIG. 10, FIG. 11 and FIG. 12 would therefore be similar to the 3-axial-port syringe illustrated and described with reference to FIG. 13 to FIG. 15. The primary differences would be:

(a) A different angular spacing of the Fill ("F"), Catheter ("C"), and drainage ("D") ports on the port body;

(b) Two axial apertures in the closed end of the barrel for the system of FIG. 27 instead of the one axial aperture in the closed end of the barrel for the system of FIG. 25;

(c) Rotations of 72 degrees instead of 90 degrees to go from one position to another; and (d) A total of 4 positions instead of 3.

Figure 28:
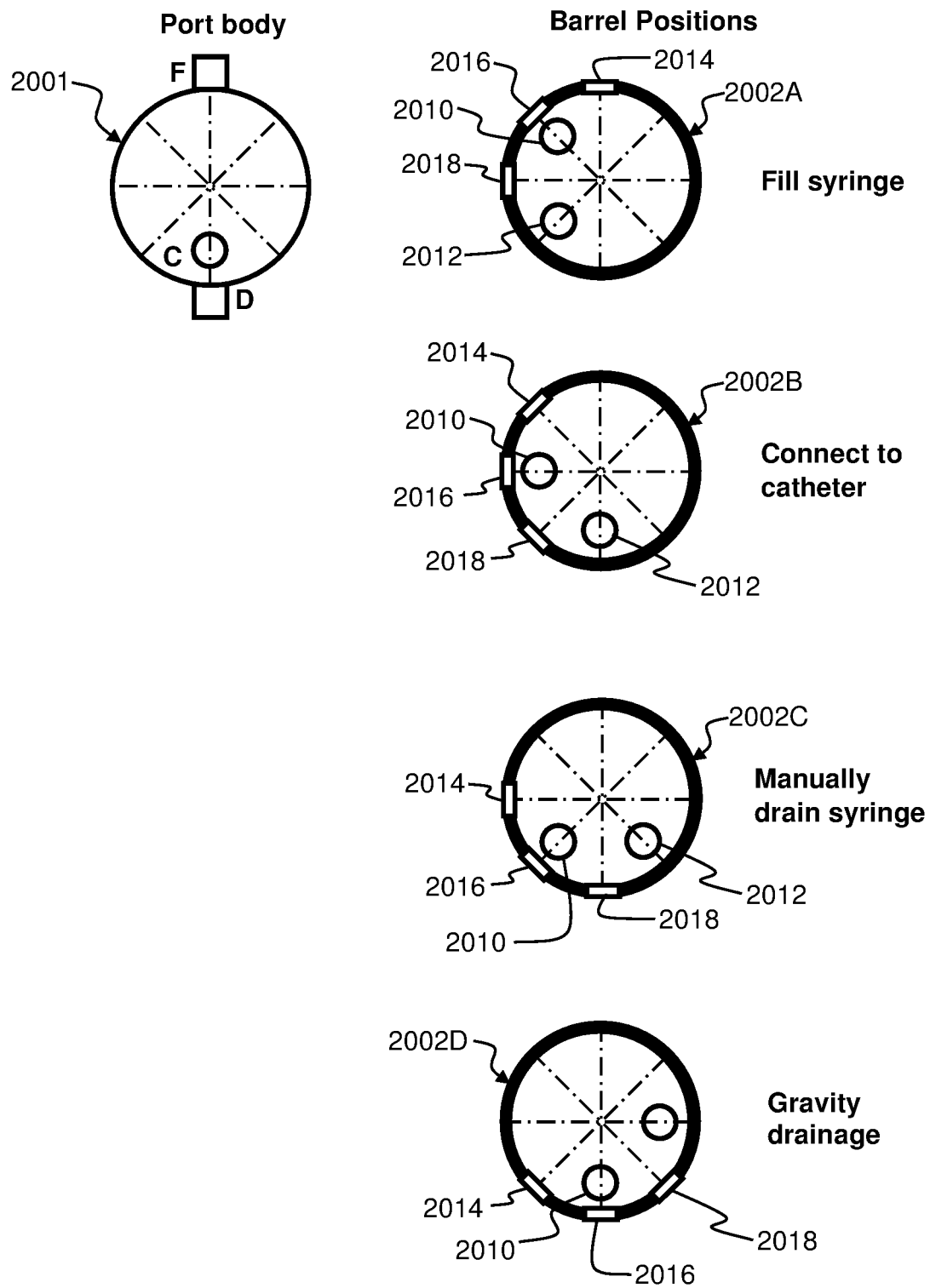
FIG. 28 shows another alternate port body and syringe barrel configuration in which two radial ports and one axial port provide selective connection to the fill, catheter, and drain ports, and continuous bladder irrigation to implement the system of FIG. 10.

FIG. 28 shows a schematic of yet another alternate configuration of a port body and barrel that has three ports (Fill or "F", Catheter or "C", and Drainage or "D") in the port body, shown at 2001. In the schematic shown in FIG. 28, the fill (or "F") port and the drainage (or "D") port are radial ports and the catheter (or "C") port is an axial port. As was the case for the schematics shown in FIG. 25, FIG. 26, and FIG. 27 the position of the port body 2001 is assumed to be the same for all rotations of the barrel in the second column. The barrel has a first barrel axial aperture, shown at 2010, a second barrel axial aperture shown at 2012, a first barrel radial aperture shown at 2014, a second barrel radial aperture shown at 2016, and a third barrel radial aperture shown at 2018. Four rotational positions of the barrel are shown at 2002A, 2002B, 2002C, and 2002D. In actual usage, the barrel would be located behind and aligned with the port body as was illustrated in FIGS. 10A to 16B. For clarity, the selectable rotations of the barrel are shown in a column to the right of the port body so that the four possible selectable rotations can be understood more clearly. From this schematic illustration, one can see that only four of the eight possible equally spaced (45-degree or ⅛th of a 360-degree circle) rotations of the barrel are needed to provide the functions needed for a 4-phase (i.e. 4-position) syringe of the type illustrated at 910 and described with reference to FIG. 10, FIG. 11, and FIG. 12. These barrel positions and the counter-clockwise sequence they occur in are:

(a) Barrel in "Fill syringe" orientation 2002A;
(b) Barrel in "Connect to catheter" orientation 2002B;
(c) Barrel in "Manually drain syringe" orientation 2002C; and
(d) Barrel in "Gravity drainage" orientation 2002D, when the Catheter ("C") port and the Drainage ("D") port in the port body 2001 are both connected to the interior of the barrel.

8. Additional Features and Fields of Use

The ports of the multi-port syringe can use any combination of any of the standard connections typically used for such medical applications, including but not limited to catheter tips, large and small luer locks, and various types of tubing. This tubing can also have external fasteners to prevent accidently dislodging of any part of the system from any other part or the system or from the catheter.

The multi-port syringe could be made in various volumetric sizes. The barrel of the multi-port syringe can have information to indicate syringe volumes as is illustrated by the numbers and lines along the length of the cylinder of the syringe barrel 430 in FIG. 4 and at 790 in FIG. 23A.

The multi-port syringe can be made of a medical grade plastic or a re-usable and sterilizable glass or polymer.

The syringe barrel, plunger piston shaft, and inner lining of the multi-port syringe, and/or any other component of the system can have an antimicrobial and/or bacteriostatic coating and/or any other treatment to reduce the spread of pathogens. This may help reduce the risk of infection to and from the patent and the user. In addition, a hydrostatic coating can be used on the inner lining of the syringe to facilitate maximum drainage of the fluid.

As previously noted with reference to FIG. 4, the catheter tip of the port body would be inserted into the irrigation port of the urinary catheter to initiate manual bladder irrigation. In this connection, the catheter tip typically fits and slips snugly inside the irrigation port and is typically a water tight connection. However, for various reasons including operator movement, high pressure irrigation or patient movement this connection can come apart and therefore contaminate the operator, the patient, the surrounding equipment and area. To help maintain this connection between the catheter tip and the irrigation port of the urinary catheter a fastener could be used to on the outside of this connection. This fastener could consist of three square walls fashioned together in an upside down "U" configuration extending longitudinally for a few centimeters. This fastener would resemble a square shaped cylinder without the bottom fourth wall. The fastener would also have a grip located on its top surface to allow its placement and removal from the connection. The grip would extend upwards a few centimeters with a convex direction facing the urinary catheter. This grip would extend from all three walls of upside down "U" configuration in a continuous fashion forming a concave circular shape. This grip would act as a single or second shield to prevent any splash from an accidental disconnection between the catheter tip and irrigation port of the urinary catheter. Using the grip, the fastener would be placed directly on the outside of the urinary catheter at the level of the irrigation port overlapping the established connection between the catheter tip and the irrigation port. This fastener would crimp down on the established connection to bolster this connection and further minimize risk of accidental dislodging of the multi-port syringe 410 and 910 from the urinary catheter 100. Once manual irrigation is no longer needed and the multi-port syringe is to be removed, the fastener would then be removed from the established connection using the upward facing grip and the catheter tip would then be extracted from the irrigation port of the urinary catheter. This fastener could be tethered to the port body with a short lanyard or as a separate piece.

The catheter tip of the port body could have a detachable tip adapter to be used with a cystoscope for irrigating through the cystoscope. Typically, a rigid cystoscope is used for examining the bladder 90 through same track the urinary catheter 100 travels through as depicted in FIG. 1, which can also be used in a woman. The cystoscope has three ports which include input and drain ports positioned at 90 degrees from the axial direction of the scope shaft along with a center lumen port which is located at the end of the scope in the axial direction and directly contiguous with the shaft of the scope. The center lumen port which is the largest port on the scope, is used for scope lens and instrument insertion. A bridging instrument, which typically has two ports is used to attach the lens and any instruments, to the central lumen port of the scope. The lens is clamped to the bridging instrument which then attaches the lens to the scope. The bridging instrument also provides a passage and guide for instruments to be passed through the shaft of the scope alongside the lens through its second port. During transurethral procedures, the user attaches a light source and camera to the lens and has irrigation running through the input port and empties the bladder through the drain port. When manual irrigation is needed during cystoscopy, the bridging piece along with the attached lens and any inserted instruments are detached from the scope at the center lumen port and a syringe is then attached with an adapter to allow for manual bladder irrigations to remove blood products, tissue material or any surgical debris. As described in FIG. 8, manual bladder irrigations can then be completed using the syringe as shown in FIG. 4 along with the cystoscope adapter in a similar fashion using the rigid scope in place of a urinary catheter 100. Once manual irrigation is complete the bridging piece can be reattached to the center lumen port along with the lens and instruments. Manual irrigation can then be repeated as needed through the procedure.

The syringe detailed in FIG. 15 could further include an additional port along the shaft of the barrel 430. This additional port could be an outlet that could be located externally on barrel wall between the external grasping features of the barrel 432 and the external indexing feature 434. This additional port (outlet) could be positioned 90 degrees to the axial length of the barrel and could have a stop cock to regulate transmission of fluid to and from the interior of the barrel to an external vessel. The external tip of the outlet could be adaptable for connection with a luer lock or any tubing source. This outlet could be used in either 3-port 3-position syringe FIG. 4 or in a 3-port 4-position syringe FIG. 12. This outlet could be functional once the seal of the plunger was extended passed the aperture of the outlet in barrel's shaft towards the open end of the barrel. This outlet could be used to obtain fluid samples from the interior of the barrel in addition to providing a second port for introducing fluid into the interior of the barrel. With the plunger locked in a partly extended position past the aperture of this outlet and towards the open end of the barrel, this outlet with the stop cock left in an open position can act as a continuous drainage port as well when combined with the alignment of barrel port (or aperture) 436 with the catheter port 422 of the port body 420. This outlet feature would provide a fourth phase or second fourth phase option of continuous gravity drainage for a 3-port 3-position syringe or 3-port 4-position syringe respectively.

The detachable port body could consist of a cylindrical cup comprising a circular bottom, a rim, and a cylindrical wall separating the circular bottom and the rim but this detachable port body could also be enclosed at the rim level. The top enclosure at the rim level could have a central aperture. As previously noted, and illustrated in FIG. 16 the detachable port body could have three circular axial apertures in the port body circular bottom: one for the input or fill port 424, one for the catheter port 422, and one for the drainage port 426. The detachable port body could contain a rotating gasket with a center conduit that would fill the enclosure space. This conduit could then travel between central aperture of the rim enclosure to communicate with the axial apertures at the bottom of the port body through the gasket. The gasket could be of medical grade material that could encase a conduit that could rotate with the conduit as one solid piece. The conduit could extend from the central aperture in the rim enclosure towards the bottom of the port body with an angle in its direction for alignments with the axial ports at the bottom of the port body. Therefore, based on rotation of the combined gasket-conduit combination, the tip of the conduit at the bottom of the port body could be in direct communication with the apertures for the fill, catheter, and drainage ports for exclusive fluid transmission between the conduit and one of the ports (422, 424, or 426). At the rim enclosure level, the conduit could extend outwards through the central aperture of the rim enclosure. This top tip of the conduit could have tip adaptable for attachment of a syringe such as a luer lock adapter, allowing any syringe to be attached to this detachable port body. The upward extending portion of the conduit that could extending from the rim enclosure and could also have a marker extending from the conduit shaft that could rotate with the conduit. This marker could be between the rim enclosure and the syringe attachment portion. The conduit marker could then rotate and align with extending markers on the outer portion of the rim enclosure to allow for locking of the conduit marker at each phase. Thus, when the conduit marker and rim enclosure extending features are aligned, the phase of the syringe could be noted and Fill, Drain and Catheter which could also match the position conduit tip at the bottom of the port body which could be in direct communication with the apertures for the fill, catheter, and drainage ports for exclusive fluid transmission between the conduit and one of the ports (422, 424, or 426) respectively. At this time manual irrigation can employed as discussed in FIG. 8 in a similar fashion with rotation of the syringe attached to the gasket-conduit combination.

One or more of the functions of the system could be implemented using an external valve or valves or an external clamp or clamps. One or more of the functions of the system could be implemented using a valve stopcock valve instead of being actuated through rotation of the barrel relative to the port body. The system could also be implemented by having a 3-port 3-position (i.e. 3-phase) syringe and implementing the fourth phase (continuous irrigation plus continuous drainage) as a bypass to the syringe through the use of one or more clamps or a valves, by for example using one or more 3-position stopcock valves and/or one or more 2-position stopcock valves and opening or closing the appropriate stopcock valves for each of the operations involved in the performance of manual irrigation and/or continuous gravity irrigation. In the 2-stopcock configuration, the input and drain would be on the same stopcock that had a 3-way valve that could rotate between fill, off, and drain.

Embodiments of the present invention are not limited to use in urinary applications. They can be used in any human or veterinary medical application, further examples of which include:

a. Gastric applications, such as with enteral feeding tubes.
   b. Automated applications in which the valves and pumping of fluids in the syringe are managed by an automated and/or computerized system.

A number of variations and modifications of the disclosed embodiments can also be used. While the principles of the disclosure have been described above in connection with specific apparatuses and methods, it is to be clearly understood that this description is made only by way of example and not as limitation on the scope of the disclosure.

What is claimed is:

1. A multi-port syringe system wherein:
the multi-port syringe system is configured for manually irrigating a bladder of a patient selected from the group of a human and an animal;
the multi-port syringe system comprises a port body, a syringe barrel, and a plunger;
the port body comprises:
   a port body cylindrical cavity;
   a first port, wherein the first port comprises an aperture through a wall of the port body cylindrical cavity configured for fluid transmission between the port body cylindrical cavity and a first medical device;
   a second port, wherein the second port comprises an aperture through a wall of the port body cylindrical cavity configured for fluid transmission between the port body cylindrical cavity and a second medical device; and
   a third port, wherein the third port comprises an aperture through a wall of the port body cylindrical cavity configured for fluid transmission between the port body cylindrical cavity and a third medical device;
the syringe barrel comprises:
   a cylindrical tube, comprising:
      a cylindrical tube interior configured for storing fluid;
      a syringe barrel central axis located at the center of the cylindrical tube interior;
      a cylindrical tube interior surface; and
      a cylindrical tube exterior surface;
   a syringe barrel closed end located on one end of the cylindrical tube; and
   a syringe barrel open end located at the opposite end of the cylindrical tube from the syringe barrel closed end;
   a syringe barrel portion comprising:
      the syringe barrel closed end; and
      at least part of the cylindrical tube exterior surface located closest to the syringe barrel closed end;
   a syringe barrel port, wherein:
      the syringe barrel port comprises a syringe barrel aperture located in the syringe barrel portion;
      the syringe barrel aperture is configured for fluid transmission into and out of the cylindrical tube interior; and
      the syringe barrel aperture is not located on the syringe barrel central axis;

the syringe barrel portion is configured for:
  nesting inside the port body cylindrical cavity; and
  rotating inside the port body cylindrical cavity about the syringe barrel central axis;
the plunger comprises:
  a plunger circular seal portion configured for:
    insertion into the syringe barrel open end;
    sealing against the cylindrical tube interior surface;
    axial movement inside the cylindrical tube interior to change the volume of fluid in the cylindrical tube interior;
  a plunger grasping feature configured for manual axial movement of the plunger along the barrel central axis; and
  a plunger shaft that connects the plunger seal portion to the plunger grasping feature; and
the multi-port syringe system is configured for:
  fluid transmission through the first port when the syringe barrel portion is in a first rotational position wherein:
    the first rotational position comprises:
      a rotation about the syringe barrel central axis;
      a rotation inside the port body cylindrical cavity; and
      an alignment of the syringe barrel port with the first port; and
    fluid transmission occurs in response to a manual axial movement of the plunger along the syringe barrel central axis;
  fluid transmission through the second port when the syringe barrel portion is in a second rotational position wherein:
    the second rotational position comprises:
      a rotation about the syringe barrel central axis;
      a rotation inside the port body cylindrical cavity; and
      an alignment of the syringe barrel port with the second port; and
    fluid transmission occurs in response to a manual axial movement of the plunger along the syringe barrel central axis;
  fluid transmission through the third port when the syringe barrel portion is in a third rotational position wherein:
    the third rotational position comprises:
      a rotation about the syringe barrel central axis;
      a rotation inside the port body cylindrical cavity; and
      an alignment of the syringe barrel port with the third port; and
    fluid transmission occurs in response to a manual axial movement of the plunger along the syringe barrel central axis.

2. The multi-port syringe system of claim 1 wherein:
the first port comprises an input port configured for connection to a fluid source;
the second port comprises a catheter port configured for fluid connection to a first lumen on a first end of a catheter;
the catheter further comprises a second lumen comprising a balloon configured for retention of a second end of the catheter in the bladder;
the third port comprises a drainage port configured for connection to a drainage fluid storage vessel;
the syringe barrel port comprises an aperture configured for radial fluid flow wherein radial fluid flow comprises flow into and out of the cylindrical tube interior in a direction perpendicular to the syringe barrel central axis;
the outlet of the input port is in a direction that is perpendicular to the syringe barrel central axis;
the outlet of the catheter port is in a direction that is parallel to the syringe barrel central axis; and
the outlet of the drainage port is in a direction that is perpendicular to the syringe barrel central axis.

3. The multi-port syringe system of claim 2 wherein:
the syringe barrel closed end further comprises a cylindrical boss wherein:
  the cylindrical boss is centered on the syringe barrel central axis;
  the cylindrical boss comprises the syringe barrel port; and
  the cylindrical boss fits into a cylindrical receptacle in the port body cylindrical cavity;
the first port, second port, and third port comprise apertures in the side walls of the cylindrical receptacle;
the syringe barrel further comprises a plunger stopper aperture located in the cylindrical tube proximate to the syringe barrel open end;
the multi-port syringe system further comprises a plunger stopper wherein the plunger stopper comprises a feature configured for:
  insertion through the plunger stopper aperture;
  prevention of accidental removal of the plunger from the syringe barrel; and
  rotationally coupling the plunger with the syringe barrel;
the syringe barrel further comprises a protrusion on the exterior of the cylindrical tube configured for retaining the syringe barrel portion inside the port body cylindrical cavity;
the multi-port syringe system further comprises a retainer wherein the retainer attaches to the port body and engages with the protrusion on the exterior of the cylindrical tube of the syringe barrel to retain the syringe barrel portion inside the cylindrical cavity;
the catheter port comprises two cylindrical bosses configured for attaching a removable catheter tip;
the port body comprises an optically clear region;
the syringe barrel comprises rotational position indication information; and
the rotational position information is configured to be viewed by a user through the optically clear region to determine if syringe barrel is in the first rotational position, the second rotational position, or the third rotational position.

4. The multi-port syringe system of claim 3 wherein:
the multi-port syringe system comprises a sterilized single-use disposable system in a sealed sterilized pouch;
the multi-port syringe system further comprises:
  a plunger cover wherein the plunger cover wraps around a plunger shaft;
  a splash shield located near the catheter port wherein the splash shield is configured for reducing an exposure of medical personnel to a content of the catheter if the port body should accidentally become disengaged from the catheter;
  a treatment that reduces a spread of pathogens;
  a fill port adapter attached to the input port;
  a fill fluid line attached to the fill port adapter;
  a check valve in the fill fluid line;
  a drip chamber in the fill fluid line;

a tapered fill fluid bag connector at the end of the fill fluid line that is opposite the end of the fill fluid line that is attached to the fill port adapter;
a drain port adapter attached to the drainage port;
a drain fluid line attached to the drain port adapter;
a check vale in the drain fluid line;
a drain bag attached to the end of the drain line that is opposite to the end of the drain line that is attached to the drain port adapter; and
a tapered tip attached to the catheter port wherein the tapered tip is configured for attachment to the catheter
an O-ring wherein the O-ring is located inside between the syringe barrel and the port body and the O-ring is configured to prevent the leakage of fluid from the syringe barrel port to the outside environment.

5. The multi-port syringe system of claim 1 wherein:
the syringe barrel port comprises an aperture configured for radial fluid flow wherein radial fluid flow comprises flow into and out of the cylindrical tube interior in a direction perpendicular to the syringe barrel central axis.

6. The multi-port syringe system of claim 1 wherein:
the syringe barrel closed end further comprises a cylindrical boss wherein:
 the cylindrical boss is centered on the syringe barrel central axis;
 the cylindrical boss comprises the syringe barrel port; and
 the cylindrical boss fits into a cylindrical receptacle in the port body cylindrical cavity; and
the first port, second port, and third port comprise apertures in the side walls of the cylindrical receptacle.

7. The multi-port syringe system of claim 1 wherein:
the syringe barrel further comprises a plunger stopper aperture located in the cylindrical tube proximate to the syringe barrel open end;
the multi-port syringe system further comprises a plunger stopper wherein the plunger stopper comprises a feature configured for:
 insertion through the plunger stopper aperture; and
 prevention of accidental removal of the plunger from the syringe barrel.

8. The multi-port syringe system of claim 7 wherein:
the plunger stopper feature configured for insertion through the plunger stopper aperture is further configured for rotationally coupling the plunger with the syringe barrel.

9. The multi-port syringe system of claim 1 wherein:
the syringe barrel further comprises a protrusion on the exterior of cylindrical tube configured for retaining the syringe barrel portion inside the port body cylindrical cavity.

10. The multi-port syringe system of claim 9 wherein:
the multi-port syringe system further comprises a retainer; and
the retainer attaches to the port body and engages with the protrusion on the exterior of the cylindrical tube of the syringe barrel to retain the syringe barrel portion inside the cylindrical cavity.

11. The multi-port syringe system of claim 1 wherein:
the first port comprises an input port configured for connection to a fluid source;
the second port comprises a catheter port configured for fluid connection to a first lumen on a first end of a catheter;
the catheter further comprises a second lumen comprising a balloon configured for retention of a second end of the catheter in the bladder;
the third port comprises a drainage port configured for connection to a drainage fluid storage vessel;
the outlet of the input port is in a direction that is perpendicular to the syringe barrel central axis;
the outlet of the catheter port is in a direction that is parallel to the syringe barrel central axis; and
the outlet of the drainage port is in a direction that is perpendicular to the syringe barrel central axis.

12. The multi-port syringe system of claim 1 wherein:
one of the port body ports is comprises a catheter port;
the catheter port comprises two cylindrical bosses configured for attaching a removable catheter tip.

13. The multi-port syringe system of claim 1 wherein:
the port body comprises an optically clear region;
the syringe barrel comprises rotational position indication information; and
the rotational position information is configured to be viewed by a user through the optically clear region to determine if the syringe barrel is in the first rotational position, the second rotational position, or the third rotational position.

14. The multi-port syringe system of claim 1 wherein:
the system further comprises an O-ring wherein:
 the O-ring is located inside between the syringe barrel and the port body; and
 the O-ring is configured to prevent the leakage of fluid from the syringe barrel port to the outside environment.

15. The multi-port syringe system of claim 1 wherein:
the multi-port syringe system comprises a sterilized single-use disposable system in a sealed sterilized pouch;
the first port comprises an input port configured for connection to a fluid source;
the second port comprises a catheter port configured for fluid connection to a first lumen on a first end of a catheter;
the catheter further comprises a second lumen comprising a balloon configured for retention of a second end of the catheter in the bladder;
the third port comprises a drainage port configured for connection to a drainage fluid storage vessel;
the multi-port syringe system further comprises:
 a fill port adapter attached to the input port;
 a fill fluid line attached to the fill port adapter;
 a check valve in the fill fluid line;
 a drip chamber in the fill fluid line;
 a tapered fill fluid bag connector at the end of the fill fluid line that is opposite the end of the fill fluid line that is attached to the fill port adapter;
 a drain port adapter attached to the drainage port;
 a drain fluid line attached to the drain port adapter;
 a check vale in the drain fluid line;
 a drain bag attached to the end of the drain line that is opposite to the end of the drain line that is attached to the drain port adapter; and
 a tapered tip attached to the catheter port wherein the tapered tip is configured for attachment to the catheter.

16. A syringe wherein:
the syringe is configured for moving fluid into and out of a human or animal bladder;
the syringe comprises a port body, which comprises a cylindrical cavity having three apertures;

the syringe comprises a cylindrical syringe barrel having an open end and a closed end, wherein:
  the closed end nests inside the cylindrical cavity;
    a portion of the syringe barrel that nests inside the cylindrical cavity comprises a syringe barrel port that can be selectively aligned with each of the three apertures of the cylindrical cavity through a rotation of the portion of the syringe barrel that nests inside the cylindrical cavity;
the syringe further comprises a plunger wherein the plunger:
  is configured to be manually moved axially inside the cylindrical syringe barrel to transfer fluid into and out of the cylindrical syringe barrel through the syringe barrel port and the selected aperture of the port body.

17. The syringe of claim 16 wherein:
the syringe barrel port comprises a radial port.

18. The multi-port syringe system of claim 1 wherein:
the closed end further comprises a cylindrical boss wherein:
  the cylindrical boss comprises the syringe barrel port; and
  the cylindrical boss fits into a cylindrical receptacle in the cylindrical cavity.

19. A method for manually moving fluid into and out of a bladder of a human or animal wherein:
the method comprises a syringe that comprises a port body, a syringe barrel, and a plunger;
the port body comprises a cylindrical cavity having three apertures;
the syringe barrel comprises a hollow cylinder with an open end and a closed end, wherein:
  the closed end nests inside the cylindrical cavity;
  the portion of the syringe barrel that nests inside the cylindrical cavity comprises a syringe barrel port;
the method comprises the steps of:
  rotating the syringe barrel inside the cylindrical cavity to selectively align the syringe barrel port with each of the three apertures of the cylindrical cavity;
  transferring fluid through the syringe barrel port and the selected aperture by manually moving the plunger axially in the hollow cylinder.

20. The method of manually moving fluid into and out of the bladder of a human or animal of claim 19, wherein:
the syringe barrel port comprises a radial port.

* * * * *